(12) United States Patent
Kiefer et al.

(10) Patent No.: US 8,906,625 B2
(45) Date of Patent: Dec. 9, 2014

(54) GENES INVOLVED IN ESTROGEN METABOLISM

(75) Inventors: Michael C. Kiefer, Clayton, CA (US); Joffre B. Baker, Montara, CA (US); James Hackett, San Jose, CA (US)

(73) Assignee: Genomic Health, Inc., Redwood City, CA (US)

( * ) Notice: Subject to any disclaimer, the term of this patent is extended or adjusted under 35 U.S.C. 154(b) by 333 days.

(21) Appl. No.: 12/971,874

(22) Filed: Dec. 17, 2010

(65) Prior Publication Data

US 2011/0275082 A1    Nov. 10, 2011

Related U.S. Application Data

(62) Division of application No. 11/731,196, filed on Mar. 30, 2007, now Pat. No. 7,888,019.

(60) Provisional application No. 60/789,187, filed on Apr. 3, 2006, provisional application No. 60/787,926, filed on Mar. 31, 2006.

(51) Int. Cl.
*C12Q 1/68* (2006.01)
*C12P 19/34* (2006.01)

(52) U.S. Cl.
CPC ........ *C12Q 1/6886* (2013.01); *C12Q 2600/118* (2013.01); *C12Q 2600/106* (2013.01)
USPC .......................... 435/6.12; 435/6.1; 435/6.11

(58) Field of Classification Search
None
See application file for complete search history.

(56) References Cited

U.S. PATENT DOCUMENTS

| | | |
|---|---|---|
| 2003/0198970 A1 | 10/2003 | Roberts et al. |
| 2003/0224374 A1 | 12/2003 | Dai et al. |
| 2004/0058340 A1 | 3/2004 | Dai et al. |
| 2004/0191817 A1 | 9/2004 | Scott et al. |
| 2005/0048542 A1 | 3/2005 | Baker et al. |
| 2005/0221398 A1 | 10/2005 | Jacquemier et al. |
| 2005/0266420 A1 | 12/2005 | Pusztai et al. |
| 2007/0031873 A1* | 2/2007 | Wang et al. ........... 435/6 |
| 2007/0099209 A1 | 5/2007 | Clarke et al. |
| 2007/0105133 A1 | 5/2007 | Clarke et al. |
| 2011/0123990 A1 | 5/2011 | Baker et al. |

FOREIGN PATENT DOCUMENTS

| | | |
|---|---|---|
| WO | WO9964626 A2 | 12/1999 |
| WO | WO9964627 A2 | 12/1999 |
| WO | WO02103320 A2 | 12/2002 |
| WO | WO 03/078662 | 9/2003 |
| WO | WO 2004/065583 | 8/2004 |
| WO | WO 2005/008213 | 1/2005 |
| WO | WO2005076005 A2 | 8/2005 |
| WO | WO2006010150 A2 | 1/2006 |
| WO | WO2007061876 A2 | 5/2007 |

OTHER PUBLICATIONS

Bieche et al., "Relationship between intratumoral expression of genes coding for xenobiotic-metabolizing enzymes and benefits from adjuvant tamoxifen in estrogen receptor alpha-positive postmenopausal breast carcinoma," Breast Cancer Research, 2004, vol. 6, No. 3, pp. R252-R263.*
Abruzzo et al., "Validation of oligonucleotide microarray data using microfluidic low-density arrays: a new statistical method to normalize real-time RT-PCR data," BioTechniques, 2005, vol. 38, pp. 785-792.*
Cronin et al., "Measurement of Gene Expression in Archival Paraffin-Embedded Tissues: Development and Performance of a 92-Gene Reverse Transcriptase-Polymerase Chain Reaction Assay," The American Journal of Pathology, 2004, vol. 164, printout pp. 1-3.*
Pusztai et al., "Gene Expression Profiles Obtained from Fine-Needle Aspirations of Breast Cancer Reliably Identify Routine Prognostic Markers and Reveal Large-Scale Molecular Differences between Estrogen-negative and Estrogen-postive Tumors," Clin. Cancer. Res., 2003, vol. 9, pp. 2406-2415.*
Yang et al., "Normalization for cDNA microarray data: a robust composite method addressing single and multiple slide systematic variation," Nucleic Acids Research, 2002, vol. 30 No. 4e15, pp. 1-10.*
GenBank Accession No. NM_000662, publicly available Mar. 24, 1999 [retrieved on-line Mar. 11, 2014; http://www.ncbi.nlm.nih.gov/sviewer/girevhist2.cgi?tool=portal&cmd=diff&db=nuccore&frst=574956987_4_107308639_Feb 26, 2014 01:24 AM_6_1&scnd=4505334_8_344126_Mar 24, 1999 05:16 PM_1_1&history_fmt=gb].*
Abba et al., "Gene expression signature of estrogen receptor a status in breast cancer" BMC Genomics (2005): 6:37.
Aulmann,et al., "Clonality of lobular carcinoma in situ (LCIS) and metachronous invasive breast cancer" Breast Cancer Res. Treat (2008): 107:331-335.
Baehner et al., "Quantitative gene expression analysis using Oncotype DX in ductal carcinoma in situ that is adjacent to invasive ductal carcinoma" Abstract #2066, (2008).
Bertucci et al., "Gene expression profiling of primary breast carcinomas using arrays of candidate genes" Human Molecular Genetics (2000): 9(20):2981-2991.
Burstein et al., "Ductal Carcinoma in Situ of the Breast" N England Journal of Medicine (2004): 350:14.
Bustin, S A., "Absolute quantification of mRNA using real-time reverse transcription polymerase chain reaction assays" J Mol Endocrinol. (2000): 25(2):169-193.
Callagy et al., "Bcl-2 is a prognostic marker in breast cancer independently of the Nottingham Prognostic Index" Clin. Cancer Res. (2006): 12(8):2468-2475.
Chan. Genomics and Proteomics, (2006): pp. 1-6.

(Continued)

*Primary Examiner* — Young J Kim
(74) *Attorney, Agent, or Firm* — Boziecevic, Field & Francis LLP

(57) ABSTRACT

The invention concerns genes that have been identified as being involved in estrogen metabolism, and are useful as diagnostic, prognostic and/or predictive markers in cancer. In particular, the invention concerns genes the tumor expression levels of which are useful in the diagnosis of cancers associated with estrogen metabolism, and/or in the prognosis of clinical outcome and/or prediction of drug response of such cancers.

19 Claims, 7 Drawing Sheets

(56) References Cited

OTHER PUBLICATIONS

Database Genescq [Online] (2001), "Human cDNA Sequence SEQ 10 No. 16674" XP002447836 retrieved from EBI Accession No. GSN: AAH17354 Database Accession No. AAH17354.

Ding et al., "Quantitative analysis of nucleic acids—the last few years of progress" J Biochem Mol Biol. (2004): 37(1):1-10.

Fisher et al., "Relative worth of estrogen or progesterone receptor and pathologic characteristics of differentiation as indicators of prognosis in node negative breast cancer patients. Findings from national surgical adjuvant breast and bowel project protocol B-06" J. Clin. Oncology (1988): 6(7):1076-1087.

Gasparini et al., "Expression of bcl-2 protein predicts efficacy of adjuvant treatments in operable node-positive breast cancer" Clinical Cancer Research (1995): 1(189-190):189-198.

Glinsky et al., "Microarray analysis identifies a death-from-cancer signature predicting therapy failure in patients with multiple types of cancer" J. Clin. Investigation (2005): 115(6):1503-1521.

Gupta et al., "The Clinical Behavior of Breast Carcinoma Is Probably Determined at the Preinvasive Stage (Ductal Carcinoma in Situ)" Cancer (1997): 80(9):1740-1745.

Kononen et al., "Tissue microarrays for high-throughput molecular profiling of tumor specimens" Nature Medicine (1998): 4(7):844-847.

Korkola et al., "Differentiation of Lobular versus Ductal Breast Carcinomas by Expression Microarray Analysis" Cancer Research (2003): 63:7167-7175.

Lah et al., "Cathepsin B, a prognostic indicator in lymph node-negative breast carcinoma patients: Comparison with cathespin D, cathespin L, and other clinical indicators" Clinical Cancer Research (2000): 6:578-584.

Linke et al., "A Multimarker Model to Predict Outcome in Tamoxifen-Treated Breast Cancer Patients" Clinical Cancer Research (2006): 12(4):1175-1183.

Ma et al., "Gene expression profiles of human breast cancer progression" PNAS (2003): 100(10):5974-5979.

Miyoshi et al., "Association of centrosomal kinase STK15/BTAK mRNA expression with chromosomal instability in human breast cancers" Int. J. Cancer (2001): 92:370-373.

Modlich et al., "Predictors of primary breast cancers responsiveness to preoperative Epirubicin/Cyclophosphamide-based chemotherapy: translation of microarray data into clinically useful predictive signatures" J. Translational Medicine (2005): 3:32.

Nakopoulou et al., "Stromelysin-3 protein expression in invasive breast cancer: Relation to proliferation, cell survival and patients' outcome" Modern Pathology (2002): 15(11):1154-1161.

Nessling et al., "Candidate genes in breast cancer revealed by microarray-based comparative genomic hybridization of archived tissue" Cancer Res. (2005): 65(2):439-447.

Nishidate et al., "Genome-wide gene-expression profiles of breast-cancer cells purified with laser microbeam microdissection: identification of genes associated with progression and metastasis" Int. J. Oncol. (2004): 25(4):797-819.

Paik et al., "A Multigene Assay to Predict Recurrence of Tamox!fen-Treated, Node-Negative Breast Cancer" New England Journal of Medicine (2004): 351(27):2817-2826.

Perou et al., "Molecular portraits of human breast tumours" Nature (2000): 406:747-752.

Reiner et al., "Immunocytochemical localization of estrogen and progesterone receptor and prognosis in human primary breast cancer" Cancer Research (1990): 50:7057-7061.

Rundle et al., "The association between glutathione S-transferase M1 genotype and polycyclic aromatic hydrocarbon-DNA adducts in breast tissue" Cancer Epidemiology, Biomarkers & Prevention (2000): 9:179-185.

Schmittgen et al. Int. J. Cancer (2003): 107:323-329.

Schnitt et al., "Benign Breast Disease and Breast Cancer Risk Morphology and Beyond" The American Journal of Surgical Pathology (2003): 27(6):836-841.

Shaaban et al., "Histopathologic Types of Benign Breast Lesions and the Risk of Breast Cancer" The American Journal of Surgical Pathology (2002): 26(4): 421-430.

Shen et al., "Prognostic meta-signature of breast cancer developed by two-stage mixture modeling of microarray data" BMC Genomics (2004): 5:94.

Simpson et al., "Molecular evolution of breast cancer" Journal of Pathology, (2005): 205:248-254.

Slamon et al., "Human breast cancer: Correlation of relapse and survival with amplification of the HER-2/neu oncogene" Science 235(4785):177-182, (1987).

Sorlie et al., "Gene expression patterns of breast carcinomas distinguish tumor subclasses with clinical implications" PNAS (2001): 98(19):10869-10874.

Span et al., "Survivin is an independent prognostic marker for risk stratification of breast cancer patients" Clinical Chemistry (2004): 50(11):1986-1993.

Stefano et al., "Expression levels and clinical-pathological correlations of HER2/neu in primary and metastatic human breast cancer" Ann. N.Y. Acad. Sci. (2004):1028:463-472.

Sternbergs's Diagnostic Surgical Pathology, Fourth edition, vol. 1, pp. 354-355, 2004.

Tanaka et al., "Centrosomal kinase AIK1 is overexpressed in invasive ductal carcinoma of the breast" Cancer Research (1999): 59:2041-2044.

Tanaka et al., "Expression of survivin and its relationship to loss of apoptosis in breast carcinomas" Clinical Cancer Research (2000): 6:127-134.

Turner et al., "BAG-1: A novel biomarker predicting long-term survival in early stage breast cancer" J. Clin. Oncol. (2001): 19(4):992-1000.

Urruticoechea et al., "Proliferation marker Ki-67 in early breast cancer" J. Clin. Oncology 23:7212-7220, (2005).

Van De Vijver et al., "A gene-expression signature as a predictor of survival in breast cancer" New Eng. J. Med. (2002): 347(25):1999-2009.

Van't Veer et al., "Gene expression profiling predicts clinical outcome of breast cancer" Nature (2002) 415:530-536.

Wellings et al., "An atlas of subgross pathology of the human breast with special reference to possible precancerous lesions" J. Nat'l Cancer Inst. (1975): 55(2):227-502.

Wellings et al., "On the origin and progression of ductal carcinoma in the human breast" J. Nat'l Cancer Inst. (1973): 50(5):1097-1419.

Chang et al., "Biologic Markers as Predictors of Clinical Outcome from Systemic Therapy for Primary Operable Breast Cancer," *J. Clin. Oncol.* 17:3058-3063 (1999).

Utsumi et al., "Steroid Sulfatase Expression is an Independent Predictor of Recurrence in Human Breast Cancer," *Cancer Res.* 59:377-381 (1999).

American Cancer Society, "Breast Cancer Overview," accessed from http://wvvw.cancer.org/acs/groups/cid/documents/webcontent/003037-pdf.pdf (Oct. 12, 2011).

Mayo Clinic Staff, "Recurrent Breast Cancer," accessed from http://kway.mayoclinic.com/health/recurrent-breast-cancer/DS01078 (May 24, 2011).

Reitsamer et al., "The Salzburg Concept of Intraoperative Radiotherapy for Breast Cancer: Results and Considerations," *Int. J. Cancer* 118:2882-2887 (2006).

\* cited by examiner

FIG. 1

SEQUENCE LISTING

```
<160> NUMBER OF SEQ ID NOS: 470

<210> SEQ ID NO 1
<211> LENGTH: 21
<212> TYPE: DNA
<213> ORGANISM: Artificial Sequence
<220> FEATURE:
<223> OTHER INFORMATION: AKR1C1.1
      Forward Primer

<400> SEQUENCE: 1
gtgtgtgaag ctgaatgatg g                                              21

<210> SEQ ID NO 2
<211> LENGTH: 18
<212> TYPE: DNA
<213> ORGANISM: Artificial Sequence
<220> FEATURE:
<223> OTHER INFORMATION: AKR1C1.1
      Reverse Primer

<400> SEQUENCE: 2
ctctgcaggc gcataggt                                                  18

<210> SEQ ID NO 3
<211> LENGTH: 24
<212> TYPE: DNA
<213> ORGANISM: Artificial Sequence
<220> FEATURE:
<223> OTHER INFORMATION: AKR1C1.1
      Probe

<400> SEQUENCE: 3
ccaaatccca ggacaggcat gaag                                           24

<210> SEQ ID NO 4
<211> LENGTH: 20
<212> TYPE: DNA
<213> ORGANISM: Artificial Sequence
<220> FEATURE:
<223> OTHER INFORMATION: AKR1C2.1
      Forward Primer

<400> SEQUENCE: 4
tgccagctca ttgctcttat                                                20

<210> SEQ ID NO 5
<211> LENGTH: 20
<212> TYPE: DNA
<213> ORGANISM: Artificial Sequence
<220> FEATURE:
<223> OTHER INFORMATION: AKR1C2.1
      Reverse Primer

<400> SEQUENCE: 5
tctgtcactg gcctggttag                                                20

<210> SEQ ID NO 6
<211> LENGTH: 26
<212> TYPE: DNA
<213> ORGANISM: Artificial Sequence
<220> FEATURE:
<223> OTHER INFORMATION: AKR1C2.1
      Probe

<400> SEQUENCE: 6
caaatgtttc ttcctccctc acaggc                                         26
```

```
<210> SEQ ID NO 7
<211> LENGTH: 23
<212> TYPE: DNA
<213> ORGANISM: Artificial Sequence
<220> FEATURE:
<223> OTHER INFORMATION: AKR1C3.1
      Forward Primer

<400> SEQUENCE: 7
gctttgcctg atgtctacca gaa                                              23

<210> SEQ ID NO 8
<211> LENGTH: 21
<212> TYPE: DNA
<213> ORGANISM: Artificial Sequence
<220> FEATURE:
<223> OTHER INFORMATION: AKR1C3.1
      Reverse Primer

<400> SEQUENCE: 8
gtccagtcac cggcatagag a                                                21

<210> SEQ ID NO 9
<211> LENGTH: 23
<212> TYPE: DNA
<213> ORGANISM: Artificial Sequence
<220> FEATURE:
<223> OTHER INFORMATION: AKR1C3.1
      Probe

<400> SEQUENCE: 9
tgcgtcacca tccacacaca ggg                                              23

<210> SEQ ID NO 10
<211> LENGTH: 20
<212> TYPE: DNA
<213> ORGANISM: Artificial Sequence
<220> FEATURE:
<223> OTHER INFORMATION: ATP5A1.1
      Forward Primer

<400> SEQUENCE: 10
gatgctgcca ctcaacaact                                                  20

<210> SEQ ID NO 11
<211> LENGTH: 20
<212> TYPE: DNA
<213> ORGANISM: Artificial Sequence
<220> FEATURE:
<223> OTHER INFORMATION: ATP5A1.1
      Reverse Primer

<400> SEQUENCE: 11
tgtccttgct tcagcaactc                                                  20

<210> SEQ ID NO 12
<211> LENGTH: 24
<212> TYPE: DNA
<213> ORGANISM: Artificial Sequence
<220> FEATURE:
<223> OTHER INFORMATION: ATP5A1.1
      Probe

<400> SEQUENCE: 12
agttagacgc acgccacgac tcaa                                             24
```

<210> SEQ ID NO 13
<211> LENGTH: 21
<212> TYPE: DNA
<213> ORGANISM: Artificial Sequence
<220> FEATURE:
<223> OTHER INFORMATION: B-actin.2
      Forward Primer

<400> SEQUENCE: 13
cagcagatgt ggatcagcaa g                                      21

<210> SEQ ID NO 14
<211> LENGTH: 18
<212> TYPE: DNA
<213> ORGANISM: Artificial Sequence
<220> FEATURE:
<223> OTHER INFORMATION: B-actin.2
      Reverse Primer

<400> SEQUENCE: 14
gcatttgcgg tggacgat                                          18

<210> SEQ ID NO 15
<211> LENGTH: 23
<212> TYPE: DNA
<213> ORGANISM: Artificial Sequence
<220> FEATURE:
<223> OTHER INFORMATION: B-actin.2
      Probe

<400> SEQUENCE: 15
aggagtatga cgagtccggc ccc                                    23

<210> SEQ ID NO 16
<211> LENGTH: 20
<212> TYPE: DNA
<213> ORGANISM: Artificial Sequence
<220> FEATURE:
<223> OTHER INFORMATION: Bcl2.1
      Probe

<400> SEQUENCE: 16
tgtacggccc cagcatgcgg                                        20

<210> SEQ ID NO 17
<211> LENGTH: 19
<212> TYPE: DNA
<213> ORGANISM: Artificial Sequence
<220> FEATURE:
<223> OTHER INFORMATION: Bcl2.1
      Forward Primer

<400> SEQUENCE: 17
ctgggatgcc tttgtggaa                                         19

<210> SEQ ID NO 18
<211> LENGTH: 22
<212> TYPE: DNA
<213> ORGANISM: Artificial Sequence
<220> FEATURE:
<223> OTHER INFORMATION: Bcl2.1
      Reverse Primer

<400> SEQUENCE: 18
cagagacagc caggagaaat ca                                     22

```
<210> SEQ ID NO 19
<211> LENGTH: 25
<212> TYPE: DNA
<213> ORGANISM: Artificial Sequence
<220> FEATURE:
<223> OTHER INFORMATION: Bcl2.2
      Forward Primer

<400> SEQUENCE: 19
cagatggacc tagtacccac tgaga                                              25

<210> SEQ ID NO 20
<211> LENGTH: 24
<212> TYPE: DNA
<213> ORGANISM: Artificial Sequence
<220> FEATURE:
<223> OTHER INFORMATION: Bcl2.2
      Reverse Primer

<400> SEQUENCE: 20
cctatgattt aagggcattt ttcc                                               24

<210> SEQ ID NO 21
<211> LENGTH: 22
<212> TYPE: DNA
<213> ORGANISM: Artificial Sequence
<220> FEATURE:
<223> OTHER INFORMATION: Bcl2.2
      Probe

<400> SEQUENCE: 21
ttccacgccg aaggacagcg at                                                 22

<210> SEQ ID NO 22
<211> LENGTH: 24
<212> TYPE: DNA
<213> ORGANISM: Artificial Sequence
<220> FEATURE:
<223> OTHER INFORMATION: Bcl2 intron 1 50kb.1
      Forward Primer

<400> SEQUENCE: 22
gcatcatttg ttgggtatgg agtt                                               24

<210> SEQ ID NO 23
<211> LENGTH: 25
<212> TYPE: DNA
<213> ORGANISM: Artificial Sequence
<220> FEATURE:
<223> OTHER INFORMATION: Bcl2 intron 1 50kb.1
      Reverse Primer

<400> SEQUENCE: 23
tctatggagg ccaatatttg attct                                              25

<210> SEQ ID NO 24
<211> LENGTH: 27
<212> TYPE: DNA
<213> ORGANISM: Artificial Sequence
<220> FEATURE:
<223> OTHER INFORMATION: Bcl2 intron 1 50kb.1
      Probe

<400> SEQUENCE: 24
agccagtgtc cctcaaccca acttctg                                            27

<210> SEQ ID NO 25
```

```
<211> LENGTH: 18
<212> TYPE: DNA
<213> ORGANISM: Artificial Sequence
<220> FEATURE:
<223> OTHER INFORMATION: Bcl2 intron 1 50kb.2
      Forward Primer

<400> SEQUENCE: 25
gggcagtggc ctgatgaa                                                    18

<210> SEQ ID NO 26
<211> LENGTH: 25
<212> TYPE: DNA
<213> ORGANISM: Artificial Sequence
<220> FEATURE:
<223> OTHER INFORMATION: Bcl2 intron 1 50kb.2
      Reverse Primer

<400> SEQUENCE: 26
atggcaaaac tgtgtctttc cttat                                            25

<210> SEQ ID NO 27
<211> LENGTH: 18
<212> TYPE: DNA
<213> ORGANISM: Artificial Sequence
<220> FEATURE:
<223> OTHER INFORMATION: Bcl2 intron 1 50kb.2
      Probe

<400> SEQUENCE: 27
cttttcttca ttttttgct                                                   18

<210> SEQ ID NO 28
<211> LENGTH: 26
<212> TYPE: DNA
<213> ORGANISM: Artificial Sequence
<220> FEATURE:
<223> OTHER INFORMATION: Bcl2 intron 1 100kb.1
      Forward Primer

<400> SEQUENCE: 28 gtcacttttta tctcacagca tcacaa                                          26

<210> SEQ ID NO 29
<211> LENGTH: 22
<212> TYPE: DNA
<213> ORGANISM: Artificial Sequence
<220> FEATURE:
<223> OTHER INFORMATION: Bcl2 intron 1 100kb.1
      Reverse Primer

<400> SEQUENCE: 29
gcattggatc ttggtgtctt ga                                               22

<210> SEQ ID NO 30
<211> LENGTH: 28
<212> TYPE: DNA
<213> ORGANISM: Artificial Sequence
<220> FEATURE:
<223> OTHER INFORMATION: Bcl2 intron 1 100kb.1
      Probe

<400> SEQUENCE: 30
aggaacatct gacagcactt gccaggtt                                         28

<210> SEQ ID NO 31
<211> LENGTH: 23
```

```
<212> TYPE: DNA
<213> ORGANISM: Artificial Sequence
<220> FEATURE:
<223> OTHER INFORMATION: Bcl2 intron 1 150kb.2
      Forward Primer

<400> SEQUENCE: 31
ggagaagtag ccagcccatt taa                                             23

<210> SEQ ID NO 32
<211> LENGTH: 18
<212> TYPE: DNA
<213> ORGANISM: Artificial Sequence
<220> FEATURE:
<223> OTHER INFORMATION: Bcl2 intron 1 150kb.2
      Reverse Primer

<400> SEQUENCE: 32
tgtccctggc gcgtttag                                                   18

<210> SEQ ID NO 33
<211> LENGTH: 20
<212> TYPE: DNA
<213> ORGANISM: Artificial Sequence
<220> FEATURE:
<223> OTHER INFORMATION: Bcl2 intron 1 150kb.2
      Probe

<400> SEQUENCE: 33
atgtcagcaa agattccagt                                                 20

<210> SEQ ID NO 34
<211> LENGTH: 21
<212> TYPE: DNA
<213> ORGANISM: Artificial Sequence
<220> FEATURE:
<223> OTHER INFORMATION: Bcl2 intron1 3'.1
      Forward Primer

<400> SEQUENCE: 34
ctagccaccc ccaagagaaa c                                               21

<210> SEQ ID NO 35
<211> LENGTH: 22
<212> TYPE: DNA
<213> ORGANISM: Artificial Sequence
<220> FEATURE:
<223> OTHER INFORMATION: Bcl2 intron1 3'.1
      Reverse Primer

<400> SEQUENCE: 35
tgccaacctc taaggtcaag gt                                              22

<210> SEQ ID NO 36
<211> LENGTH: 24
<212> TYPE: DNA
<213> ORGANISM: Artificial Sequence
<220> FEATURE:
<223> OTHER INFORMATION: Bcl2 intron1 3'.1
      Probe

<400> SEQUENCE: 36
cctgacagct ccctttcccc agga                                            24

<210> SEQ ID NO 37
<211> LENGTH: 21
<212> TYPE: DNA
```

```
<213> ORGANISM: Artificial Sequence
<220> FEATURE:
<223> OTHER INFORMATION: Bcl2-beta.1
      Forward Primer

<400> SEQUENCE: 37
tgggtaggtg cacttggtga t                                              21

<210> SEQ ID NO 38
<211> LENGTH: 18
<212> TYPE: DNA
<213> ORGANISM: Artificial Sequence
<220> FEATURE:
<223> OTHER INFORMATION: Bcl2-beta.1
      Reverse Primer

<400> SEQUENCE: 38
actccaaccc ccgcatct                                                  18

<210> SEQ ID NO 39
<211> LENGTH: 24
<212> TYPE: DNA
<213> ORGANISM: Artificial Sequence
<220> FEATURE:
<223> OTHER INFORMATION: Bcl2-beta.1
      Probe

<400> SEQUENCE: 39
acctgtggcc tcagcccaga ctca                                           24

<210> SEQ ID NO 40
<211> LENGTH: 22
<212> TYPE: DNA
<213> ORGANISM: Artificial Sequence
<220> FEATURE:
<223> OTHER INFORMATION: CAT.1
      Forward Primer

<400> SEQUENCE: 40
atccattcga tctcaccaag gt                                             22

<210> SEQ ID NO 41
<211> LENGTH: 23
<212> TYPE: DNA
<213> ORGANISM: Artificial Sequence
<220> FEATURE:
<223> OTHER INFORMATION: CAT.1
      Reverse Primer

<400> SEQUENCE: 41
tccggtttaa gaccagttta cca                                            23

<210> SEQ ID NO 42
<211> LENGTH: 28
<212> TYPE: DNA
<213> ORGANISM: Artificial Sequence
<220> FEATURE:
<223> OTHER INFORMATION: CAT.1
      Probe

<400> SEQUENCE: 42
tggcctcaca aggactaccc tctcatcc                                       28

<210> SEQ ID NO 43
<211> LENGTH: 18
<212> TYPE: DNA
<213> ORGANISM: Artificial Sequence
```

<220> FEATURE:
<223> OTHER INFORMATION: CD68.2
      Forward Primer

<400> SEQUENCE: 43
tggttcccag ccctgtgt                                                      18

<210> SEQ ID NO 44
<211> LENGTH: 19
<212> TYPE: DNA
<213> ORGANISM: Artificial Sequence
<220> FEATURE:
<223> OTHER INFORMATION: CD68.2
      Reverse Primer

<400> SEQUENCE: 44
ctcctccacc ctgggttgt                                                     19

<210> SEQ ID NO 45
<211> LENGTH: 28
<212> TYPE: DNA
<213> ORGANISM: Artificial Sequence
<220> FEATURE:
<223> OTHER INFORMATION: CD68.2
      Probe

<400> SEQUENCE: 45
ctccaagccc agattcagat tcgagtca                                           28

<210> SEQ ID NO 46
<211> LENGTH: 21
<212> TYPE: DNA
<213> ORGANISM: Artificial Sequence
<220> FEATURE:
<223> OTHER INFORMATION: CDH1.3
      Forward Primer

<400> SEQUENCE: 46
tgagtgtccc ccggtatctt c                                                  21

<210> SEQ ID NO 47
<211> LENGTH: 21
<212> TYPE: DNA
<213> ORGANISM: Artificial Sequence
<220> FEATURE:
<223> OTHER INFORMATION: CDH1.3
      Reverse Primer

<400> SEQUENCE: 47
cagccgcttt cagattttca t                                                  21

<210> SEQ ID NO 48
<211> LENGTH: 27
<212> TYPE: DNA
<213> ORGANISM: Artificial Sequence
<220> FEATURE:
<223> OTHER INFORMATION: CDH1.3
      Probe

<400> SEQUENCE: 48
tgccaatccc gatgaaattg gaaattt                                            27

<210> SEQ ID NO 49
<211> LENGTH: 21
<212> TYPE: DNA
<213> ORGANISM: Artificial Sequence
<220> FEATURE:

```
<223> OTHER INFORMATION: CEGP1.2
      Forward Primer

<400> SEQUENCE: 49
tgacaatcag cacacctgca t                                            21

<210> SEQ ID NO 50
<211> LENGTH: 23
<212> TYPE: DNA
<213> ORGANISM: Artificial Sequence
<220> FEATURE:
<223> OTHER INFORMATION: CEGP1.2
      Reverse Primer

<400> SEQUENCE: 50
tgtgactaca gccgtgatcc tta                                          23

<210> SEQ ID NO 51
<211> LENGTH: 20
<212> TYPE: DNA
<213> ORGANISM: Artificial Sequence
<220> FEATURE:
<223> OTHER INFORMATION: CEGP1.2
      Probe

<400> SEQUENCE: 51
caggccctct tccgagcggt                                              20

<210> SEQ ID NO 52
<211> LENGTH: 22
<212> TYPE: DNA
<213> ORGANISM: Artificial Sequence
<220> FEATURE:
<223> OTHER INFORMATION: CEGP1.6
      Forward Primer

<400> SEQUENCE: 52
gctgcatttt atgtccaaat gg                                           22

<210> SEQ ID NO 53
<211> LENGTH: 19
<212> TYPE: DNA
<213> ORGANISM: Artificial Sequence
<220> FEATURE:
<223> OTHER INFORMATION: CEGP1.6
      Forward Primer

<400> SEQUENCE: 53
tggtcttggg catggttca                                               19

<210> SEQ ID NO 54
<211> LENGTH: 20
<212> TYPE: DNA
<213> ORGANISM: Artificial Sequence
<220> FEATURE:
<223> OTHER INFORMATION: CEGP1.6
      Probe

<400> SEQUENCE: 54
atttgtcctt cctcattttg                                              20

<210> SEQ ID NO 55
<211> LENGTH: 19
<212> TYPE: DNA
<213> ORGANISM: Artificial Sequence
<220> FEATURE:
<223> OTHER INFORMATION: CEGP1 intron 4.1
```

Forward Primer

<400> SEQUENCE: 55
tccccttgcc tttggagaa					19

<210> SEQ ID NO 56
<211> LENGTH: 19
<212> TYPE: DNA
<213> ORGANISM: Artificial Sequence
<220> FEATURE:
<223> OTHER INFORMATION: CEGP1 intron 4.1
      Reverse Primer

<400> SEQUENCE: 56
aaaggcctgg aggcatcaa					19

<210> SEQ ID NO 57
<211> LENGTH: 13
<212> TYPE: DNA
<213> ORGANISM: Artificial Sequence
<220> FEATURE:
<223> OTHER INFORMATION: CEGP1 intron 4.1
      Probe

<400> SEQUENCE: 57
cagcccaaat cct					13

<210> SEQ ID NO 58
<211> LENGTH: 25
<212> TYPE: DNA
<213> ORGANISM: Artificial Sequence
<220> FEATURE:
<223> OTHER INFORMATION: CEGP1 intron 5.1
      Forward Primer

<400> SEQUENCE: 58
cttaatggtg tttagcacag atgca					25

<210> SEQ ID NO 59
<211> LENGTH: 20
<212> TYPE: DNA
<213> ORGANISM: Artificial Sequence
<220> FEATURE:
<223> OTHER INFORMATION: CEGP1 intron 5.1
      Reverse Primer

<400> SEQUENCE: 59
ccactgtagc atgcgaagca					20

<210> SEQ ID NO 60
<211> LENGTH: 16
<212> TYPE: DNA
<213> ORGANISM: Artificial Sequence
<220> FEATURE:
<223> OTHER INFORMATION: CEGP1 intron 5.1
      Probe

<400> SEQUENCE: 60
caaatgcaca ggaaac					16

<210> SEQ ID NO 61
<211> LENGTH: 21
<212> TYPE: DNA
<213> ORGANISM: Artificial Sequence
<220> FEATURE:
<223> OTHER INFORMATION: COMT.1
      Forward Primer

```
<400> SEQUENCE: 61
ccttatcggc tggaacgagt t                                        21

<210> SEQ ID NO 62
<211> LENGTH: 21
<212> TYPE: DNA
<213> ORGANISM: Artificial Sequence
<220> FEATURE:
<223> OTHER INFORMATION: COMT.1
      Reverse Primer

<400> SEQUENCE: 62
ctccttggtg tcacccatga g                                        21

<210> SEQ ID NO 63
<211> LENGTH: 21
<212> TYPE: DNA
<213> ORGANISM: Artificial Sequence
<220> FEATURE:
<223> OTHER INFORMATION: COMT.1
      Probe

<400> SEQUENCE: 63
cctgcagccc atccacaacc t                                        21

<210> SEQ ID NO 64
<211> LENGTH: 22
<212> TYPE: DNA
<213> ORGANISM: Artificial Sequence
<220> FEATURE:
<223> OTHER INFORMATION: COX8.1
      Forward Primer

<400> SEQUENCE: 64
cgttctgtcc ctcacactgt ga                                       22

<210> SEQ ID NO 65
<211> LENGTH: 24
<212> TYPE: DNA
<213> ORGANISM: Artificial Sequence
<220> FEATURE:
<223> OTHER INFORMATION: COX8.1
      Reverse Primer

<400> SEQUENCE: 65
caaatgcagt aacatgacca ggat                                     24

<210> SEQ ID NO 66
<211> LENGTH: 18
<212> TYPE: DNA
<213> ORGANISM: Artificial Sequence
<220> FEATURE:
<223> OTHER INFORMATION: COX8.1
      Probe

<400> SEQUENCE: 66
tgaccagccc caccggcc                                            18

<210> SEQ ID NO 67
<211> LENGTH: 20
<212> TYPE: DNA
<213> ORGANISM: Artificial Sequence
<220> FEATURE:
<223> OTHER INFORMATION: CRYZ.1
      Forward Primer
```

```
<400> SEQUENCE: 67
aagtcctgaa attgcgatca                                              20

<210> SEQ ID NO 68
<211> LENGTH: 20
<212> TYPE: DNA
<213> ORGANISM: Artificial Sequence
<220> FEATURE:
<223> OTHER INFORMATION: CRYZ.1
      Reverse Primer

<400> SEQUENCE: 68
cacatgcatg gaccttgatt                                              20

<210> SEQ ID NO 69
<211> LENGTH: 26
<212> TYPE: DNA
<213> ORGANISM: Artificial Sequence
<220> FEATURE:
<223> OTHER INFORMATION: CRYZ.1
      Probe

<400> SEQUENCE: 69
ccgattccaa aagaccatca ggttct                                       26

<210> SEQ ID NO 70
<211> LENGTH: 21
<212> TYPE: DNA
<213> ORGANISM: Artificial Sequence
<220> FEATURE:
<223> OTHER INFORMATION: CTSL2.1
      Forward Primer

<400> SEQUENCE: 70
tgtctcactg agcgagcaga a                                            21

<210> SEQ ID NO 71
<211> LENGTH: 19
<212> TYPE: DNA
<213> ORGANISM: Artificial Sequence
<220> FEATURE:
<223> OTHER INFORMATION: CTSL2.1
      Reverse Primer

<400> SEQUENCE: 71
accattgcag ccctgattg                                               19

<210> SEQ ID NO 72
<211> LENGTH: 24
<212> TYPE: DNA
<213> ORGANISM: Artificial Sequence
<220> FEATURE:
<223> OTHER INFORMATION: CTSL2.1
      Probe

<400> SEQUENCE: 72
cttgaggacg cgaacagtcc acca                                         24

<210> SEQ ID NO 73
<211> LENGTH: 20
<212> TYPE: DNA
<213> ORGANISM: Artificial Sequence
<220> FEATURE:
<223> OTHER INFORMATION: CTSL2.10
      Forward Primer

<400> SEQUENCE: 73
```

```
tcagaggctt gtttgctgag                                               20
```

<210> SEQ ID NO 74
<211> LENGTH: 20
<212> TYPE: DNA
<213> ORGANISM: Artificial Sequence
<220> FEATURE:
<223> OTHER INFORMATION: CTSL2.10
      Reverse Primer

<400> SEQUENCE: 74

```
aggacgagcg aaagattcat                                               20
```

<210> SEQ ID NO 75
<211> LENGTH: 22
<212> TYPE: DNA
<213> ORGANISM: Artificial Sequence
<220> FEATURE:
<223> OTHER INFORMATION: CTSL2.10
      Probe

<400> SEQUENCE: 75

```
cgacggctgc tggttttgaa ac                                            22
```

<210> SEQ ID NO 76
<211> LENGTH: 27
<212> TYPE: DNA
<213> ORGANISM: Artificial Sequence
<220> FEATURE:
<223> OTHER INFORMATION: CYP.1
      Forward Primer

<400> SEQUENCE: 76

```
tggacttcta gtgatgagaa agattga                                       27
```

<210> SEQ ID NO 77
<211> LENGTH: 22
<212> TYPE: DNA
<213> ORGANISM: Artificial Sequence
<220> FEATURE:
<223> OTHER INFORMATION: CYP.1
      Reverse Primer

<400> SEQUENCE: 77

```
cactgcgaga tcaccacagg ta                                            22
```

<210> SEQ ID NO 78
<211> LENGTH: 25
<212> TYPE: DNA
<213> ORGANISM: Artificial Sequence
<220> FEATURE:
<223> OTHER INFORMATION: CYP.1
      Probe

<400> SEQUENCE: 78

```
ttcccacagg ccccaacaat aagcc                                         25
```

<210> SEQ ID NO 79
<211> LENGTH: 20
<212> TYPE: DNA
<213> ORGANISM: Artificial Sequence
<220> FEATURE:
<223> OTHER INFORMATION: CYP17A1.1
      Forward Primer

<400> SEQUENCE: 79
ccggagtgac tctatcacca                                           20

<210> SEQ ID NO 80
<211> LENGTH: 19
<212> TYPE: DNA
<213> ORGANISM: Artificial Sequence
<220> FEATURE:
<223> OTHER INFORMATION: CYP17A1.1
      Reverse Primer

<400> SEQUENCE: 80
gccagcattg ccattatct                                            19

<210> SEQ ID NO 81
<211> LENGTH: 24
<212> TYPE: DNA
<213> ORGANISM: Artificial Sequence
<220> FEATURE:
<223> OTHER INFORMATION: CYP17A1.1
      Probe

<400> SEQUENCE: 81
tggacacact gatgcaagcc aaga                                      24

<210> SEQ ID NO 82
<211> LENGTH: 26
<212> TYPE: DNA
<213> ORGANISM: Artificial Sequence
<220> FEATURE:
<223> OTHER INFORMATION: CYP19A1.1
      Forward Primer

<400> SEQUENCE: 82
tccttatagg tactttcagc catttg                                    26

<210> SEQ ID NO 83
<211> LENGTH: 21
<212> TYPE: DNA
<213> ORGANISM: Artificial Sequence
<220> FEATURE:
<223> OTHER INFORMATION: CYP19A1.1
      Reverse Primer

<400> SEQUENCE: 83
caccatggcg atgtactttc c                                         21

<210> SEQ ID NO 84
<211> LENGTH: 19
<212> TYPE: DNA
<213> ORGANISM: Artificial Sequence
<220> FEATURE:
<223> OTHER INFORMATION: CYP19A1.1
      Probe

<400> SEQUENCE: 84
cacagccacg gggcccaaa                                            19

<210> SEQ ID NO 85
<211> LENGTH: 20
<212> TYPE: DNA
<213> ORGANISM: Artificial Sequence
<220> FEATURE:
<223> OTHER INFORMATION: CYP1A1.2
      Forward Primer

<400> SEQUENCE: 85
aataatttcg gggaggtggt                                           20

```
<210> SEQ ID NO 86
<211> LENGTH: 20
<212> TYPE: DNA
<213> ORGANISM: Artificial Sequence
<220> FEATURE:
<223> OTHER INFORMATION: CYP1A1.2
      Reverse Primer

<400> SEQUENCE: 86
ggttgggtag gtagcgaaga                                          20

<210> SEQ ID NO 87
<211> LENGTH: 24
<212> TYPE: DNA
<213> ORGANISM: Artificial Sequence
<220> FEATURE:
<223> OTHER INFORMATION: CYP1A1.2
      Probe

<400> SEQUENCE: 87
tggctctgga aacccagctg actt                                     24

<210> SEQ ID NO 88
<211> LENGTH: 22
<212> TYPE: DNA
<213> ORGANISM: Artificial Sequence
<220> FEATURE:
<223> OTHER INFORMATION: CYP1B1.3
      Forward Primer

<400> SEQUENCE: 88
ccagctttgt gcctgtcact at                                       22

<210> SEQ ID NO 89
<211> LENGTH: 20
<212> TYPE: DNA
<213> ORGANISM: Artificial Sequence
<220> FEATURE:
<223> OTHER INFORMATION: CYP1B1.3
      Reverse Primer

<400> SEQUENCE: 89
gggaatgtgg tagcccaaga                                          20

<210> SEQ ID NO 90
<211> LENGTH: 25
<212> TYPE: DNA
<213> ORGANISM: Artificial Sequence
<220> FEATURE:
<223> OTHER INFORMATION: CYP1B1.3
      Probe

<400> SEQUENCE: 90
ctcatgccac cactgccaac acctc                                    25

<210> SEQ ID NO 91
<211> LENGTH: 21
<212> TYPE: DNA
<213> ORGANISM: Artificial Sequence
<220> FEATURE:
<223> OTHER INFORMATION: CYP4Z1.1
      Forward Primer

<400> SEQUENCE: 91
gccttacacc acgatgtgca t                                        21
```

<210> SEQ ID NO 92
<211> LENGTH: 27
<212> TYPE: DNA
<213> ORGANISM: Artificial Sequence
<220> FEATURE:
<223> OTHER INFORMATION: CYP4Z1.1
      Reverse Primer

<400> SEQUENCE: 92
gtcgagtaac cgggatatgt ttactac                                27

<210> SEQ ID NO 93
<211> LENGTH: 25
<212> TYPE: DNA
<213> ORGANISM: Artificial Sequence
<220> FEATURE:
<223> OTHER INFORMATION: CYP4Z1.1
      Probe

<400> SEQUENCE: 93
aaggaatgcc tccgcctcta cgcac                                  25

<210> SEQ ID NO 94
<211> LENGTH: 20
<212> TYPE: DNA
<213> ORGANISM: Artificial Sequence
<220> FEATURE:
<223> OTHER INFORMATION: EPHX1.2
      Forward Primer

<400> SEQUENCE: 94
accgtaggct ctgctctgaa                                        20

<210> SEQ ID NO 95
<211> LENGTH: 20
<212> TYPE: DNA
<213> ORGANISM: Artificial Sequence
<220> FEATURE:
<223> OTHER INFORMATION: EPHX1.2
      Reverse Primer

<400> SEQUENCE: 95
tggtccaggt ggaaaacttc                                        20

<210> SEQ ID NO 96
<211> LENGTH: 20
<212> TYPE: DNA
<213> ORGANISM: Artificial Sequence
<220> FEATURE:
<223> OTHER INFORMATION: EPHX1.2
      Probe

<400> SEQUENCE: 96
aggcagccag acccacagga                                        20

<210> SEQ ID NO 97
<211> LENGTH: 19
<212> TYPE: DNA
<213> ORGANISM: Artificial Sequence
<220> FEATURE:
<223> OTHER INFORMATION: EstR1.1
      Forward Primer

<400> SEQUENCE: 97
cgtggtgccc ctctatgac                                         19

```
<210> SEQ ID NO 98
<211> LENGTH: 19
<212> TYPE: DNA
<213> ORGANISM: Artificial Sequence
<220> FEATURE:
<223> OTHER INFORMATION: EstR1.1
      Reverse Primer

<400> SEQUENCE: 98
ggctagtggg cgcatgtag                                                    19

<210> SEQ ID NO 99
<211> LENGTH: 19
<212> TYPE: DNA
<213> ORGANISM: Artificial Sequence
<220> FEATURE:
<223> OTHER INFORMATION: EstR1.1
      Probe

<400> SEQUENCE: 99
ctggagatgc tggacgccc                                                    19

<210> SEQ ID NO 100
<211> LENGTH: 19
<212> TYPE: DNA
<213> ORGANISM: Artificial Sequence
<220> FEATURE:
<223> OTHER INFORMATION: FOXM1.1
      Forward Primer

<400> SEQUENCE: 100
ccaccccgag caaatctgt                                                    19

<210> SEQ ID NO 101
<211> LENGTH: 22
<212> TYPE: DNA
<213> ORGANISM: Artificial Sequence
<220> FEATURE:
<223> OTHER INFORMATION: FOXM1.1
      Reverse Primer

<400> SEQUENCE: 101
aaatccagtc ccctactttt gg                                                22

<210> SEQ ID NO 102
<211> LENGTH: 23
<212> TYPE: DNA
<213> ORGANISM: Artificial Sequence
<220> FEATURE:
<223> OTHER INFORMATION: FOXM1.1
      Probe

<400> SEQUENCE: 102
cctgaatcct ggaggctcac gcc                                               23

<210> SEQ ID NO 103
<211> LENGTH: 20
<212> TYPE: DNA
<213> ORGANISM: Artificial Sequence
<220> FEATURE:
<223> OTHER INFORMATION: FOXM1.3
      Forward Primer

<400> SEQUENCE: 103
tgcccagatg tgcgctatta                                                   20

<210> SEQ ID NO 104
```

```
<211> LENGTH: 21
<212> TYPE: DNA
<213> ORGANISM: Artificial Sequence
<220> FEATURE:
<223> OTHER INFORMATION: FOXM1.3
      Reverse Primer

<400> SEQUENCE: 104
tcaatgccag tctccctggt a                                             21

<210> SEQ ID NO 105
<211> LENGTH: 20
<212> TYPE: DNA
<213> ORGANISM: Artificial Sequence
<220> FEATURE:
<223> OTHER INFORMATION: FOXM1.3
      Probe

<400> SEQUENCE: 105
atgtttctct gataatgtcc                                               20

<210> SEQ ID NO 106
<211> LENGTH: 24
<212> TYPE: DNA
<213> ORGANISM: Artificial Sequence
<220> FEATURE:
<223> OTHER INFORMATION: FOXM1 intron 5.1
      Forward Primer

<400> SEQUENCE: 106
tggacagaga caagatgtga tgtg                                          24

<210> SEQ ID NO 107
<211> LENGTH: 22
<212> TYPE: DNA
<213> ORGANISM: Artificial Sequence
<220> FEATURE:
<223> OTHER INFORMATION: FOXM1 intron 5.1
      Reverse Primer

<400> SEQUENCE: 107
gctggcacct agacaaaaca tg                                            22

<210> SEQ ID NO 108
<211> LENGTH: 15
<212> TYPE: DNA
<213> ORGANISM: Artificial Sequence
<220> FEATURE:
<223> OTHER INFORMATION: FOXM1 intron 5.1
      Probe

<400> SEQUENCE: 108
ccatagggac ccttc                                                    15

<210> SEQ ID NO 109
<211> LENGTH: 25
<212> TYPE: DNA
<213> ORGANISM: Artificial Sequence
<220> FEATURE:
<223> OTHER INFORMATION: FOXM1 intron 7.1
      Forward Primer

<400> SEQUENCE: 109
ggtgtcctat tttcctctga agaga                                         25

<210> SEQ ID NO 110
<211> LENGTH: 21
```

```
<212> TYPE: DNA
<213> ORGANISM: Artificial Sequence
<220> FEATURE:
<223> OTHER INFORMATION: FOXM1 intron 7.1
      Reverse Primer

<400> SEQUENCE: 110
tgcaagctga aggtccaaca t                                              21

<210> SEQ ID NO 111
<211> LENGTH: 15
<212> TYPE: DNA
<213> ORGANISM: Artificial Sequence
<220> FEATURE:
<223> OTHER INFORMATION: FOXM1 intron 7.1
      Probe

<400> SEQUENCE: 111
ttctggccaa ttaag                                                     15

<210> SEQ ID NO 112
<211> LENGTH: 20
<212> TYPE: DNA
<213> ORGANISM: Artificial Sequence
<220> FEATURE:
<223> OTHER INFORMATION: GAPDH.1
      Forward Primer

<400> SEQUENCE: 112
attccaccca tggcaaattc                                                20

<210> SEQ ID NO 113
<211> LENGTH: 22
<212> TYPE: DNA
<213> ORGANISM: Artificial Sequence
<220> FEATURE:
<223> OTHER INFORMATION: GAPDH.1
      Reverse Primer

<400> SEQUENCE: 113
gatgggattt ccattgatga ca                                             22

<210> SEQ ID NO 114
<211> LENGTH: 22
<212> TYPE: DNA
<213> ORGANISM: Artificial Sequence
<220> FEATURE:
<223> OTHER INFORMATION: GAPDH.1
      Probe

<400> SEQUENCE: 114
ccgttctcag ccttgacggt gc                                             22

<210> SEQ ID NO 115
<211> LENGTH: 20
<212> TYPE: DNA
<213> ORGANISM: Artificial Sequence
<220> FEATURE:
<223> OTHER INFORMATION: GCLC.3
      Forward Primer

<400> SEQUENCE: 115
ctgttgcagg aaggcattga                                                20

<210> SEQ ID NO 116
<211> LENGTH: 28
<212> TYPE: DNA
```

```
<213> ORGANISM: Artificial Sequence
<220> FEATURE:
<223> OTHER INFORMATION: GCLC.3
      Reverse Primer

<400> SEQUENCE: 116
gtcagtgggt ctctaataaa gagatgag                                    28

<210> SEQ ID NO 117
<211> LENGTH: 21
<212> TYPE: DNA
<213> ORGANISM: Artificial Sequence
<220> FEATURE:
<223> OTHER INFORMATION: GCLC.3
      Probe

<400> SEQUENCE: 117
catctcctgg cccagcatgt t                                           21

<210> SEQ ID NO 118
<211> LENGTH: 30
<212> TYPE: DNA
<213> ORGANISM: Artificial Sequence
<220> FEATURE:
<223> OTHER INFORMATION: GCLM.2
      Forward Primer

<400> SEQUENCE: 118
tgtagaatca aactcttcat catcaactag                                  30

<210> SEQ ID NO 119
<211> LENGTH: 22
<212> TYPE: DNA
<213> ORGANISM: Artificial Sequence
<220> FEATURE:
<223> OTHER INFORMATION: GCLM.2
      Reverse Primer

<400> SEQUENCE: 119
cacagaatcc agctgtgcaa ct                                          22

<210> SEQ ID NO 120
<211> LENGTH: 26
<212> TYPE: DNA
<213> ORGANISM: Artificial Sequence
<220> FEATURE:
<223> OTHER INFORMATION: GCLM.2
      Probe

<400> SEQUENCE: 120
tgcagttgac atggcctgtt cagtcc                                      26

<210> SEQ ID NO 121
<211> LENGTH: 18
<212> TYPE: DNA
<213> ORGANISM: Artificial Sequence
<220> FEATURE:
<223> OTHER INFORMATION: GPX1.2
      Forward Primer

<400> SEQUENCE: 121
gcttatgacc gaccccaa                                               18

<210> SEQ ID NO 122
<211> LENGTH: 20
<212> TYPE: DNA
<213> ORGANISM: Artificial Sequence
```

```
<220> FEATURE:
<223> OTHER INFORMATION: GPX1.2
      Reverse Primer

<400> SEQUENCE: 122
aaagttccag gcaacatcgt                                               20

<210> SEQ ID NO 123
<211> LENGTH: 24
<212> TYPE: DNA
<213> ORGANISM: Artificial Sequence
<220> FEATURE:
<223> OTHER INFORMATION: GPX1.2
      Probe

<400> SEQUENCE: 123
ctcatcacct ggtctccggt gtgt                                          24

<210> SEQ ID NO 124
<211> LENGTH: 24
<212> TYPE: DNA
<213> ORGANISM: Artificial Sequence
<220> FEATURE:
<223> OTHER INFORMATION: GPX2.2
      Forward Primer

<400> SEQUENCE: 124
cacacagatc tcctactcca tcca                                          24

<210> SEQ ID NO 125
<211> LENGTH: 21
<212> TYPE: DNA
<213> ORGANISM: Artificial Sequence
<220> FEATURE:
<223> OTHER INFORMATION: GPX2.2
      Reverse Primer

<400> SEQUENCE: 125
ggtccagcag tgtctcctga a                                             21

<210> SEQ ID NO 126
<211> LENGTH: 26
<212> TYPE: DNA
<213> ORGANISM: Artificial Sequence
<220> FEATURE:
<223> OTHER INFORMATION: GPX2.2
      Probe

<400> SEQUENCE: 126
catgctgcat cctaaggctc ctcagg                                        26

<210> SEQ ID NO 127
<211> LENGTH: 20
<212> TYPE: DNA
<213> ORGANISM: Artificial Sequence
<220> FEATURE:
<223> OTHER INFORMATION: GSTM1.1
      Reverse Primer

<400> SEQUENCE: 127
ggcccagctt gaattttca                                                20

<210> SEQ ID NO 128
<211> LENGTH: 27
<212> TYPE: DNA
<213> ORGANISM: Artificial Sequence
<220> FEATURE:
```

<223> OTHER INFORMATION: GSTM1.1
    Forward Primer

<400> SEQUENCE: 128
aagctatgag gaaaagaagt acacgat                                              27

<210> SEQ ID NO 129
<211> LENGTH: 30
<212> TYPE: DNA
<213> ORGANISM: Artificial Sequence
<220> FEATURE:
<223> OTHER INFORMATION: GSTM1.1
    Probe

<400> SEQUENCE: 129
tcagccactg gcttctgtca taatcaggag                                           30

<210> SEQ ID NO 130
<211> LENGTH: 20
<212> TYPE: DNA
<213> ORGANISM: Artificial Sequence
<220> FEATURE:
<223> OTHER INFORMATION: GSTM1 var2.1
    Forward Primer

<400> SEQUENCE: 130
ccatggtttg caggaaacaa                                                      20

<210> SEQ ID NO 131
<211> LENGTH: 22
<212> TYPE: DNA
<213> ORGANISM: Artificial Sequence
<220> FEATURE:
<223> OTHER INFORMATION: GSTM1 var2.1
    Reverse Primer

<400> SEQUENCE: 131
agaacacagg tcttgggagg aa                                                   22

<210> SEQ ID NO 132
<211> LENGTH: 25
<212> TYPE: DNA
<213> ORGANISM: Artificial Sequence
<220> FEATURE:
<223> OTHER INFORMATION: GSTM1 var2.1
    Probe

<400> SEQUENCE: 132
atctctgcct acatgaagtc cagcc                                                25

<210> SEQ ID NO 133
<211> LENGTH: 23
<212> TYPE: DNA
<213> ORGANISM: Artificial Sequence
<220> FEATURE:
<223> OTHER INFORMATION: GSTM1 intron 1.1
    Forward Primer

<400> SEQUENCE: 133
aacgggtacg tgcagtgtaa act                                                  23

<210> SEQ ID NO 134
<211> LENGTH: 19
<212> TYPE: DNA
<213> ORGANISM: Artificial Sequence
<220> FEATURE:
<223> OTHER INFORMATION: GSTM1 intron 1.1

Reverse Primer

<400> SEQUENCE: 134
gcaggtcgcg tcagagatg                                        19

<210> SEQ ID NO 135
<211> LENGTH: 26
<212> TYPE: DNA
<213> ORGANISM: Artificial Sequence
<220> FEATURE:
<223> OTHER INFORMATION: GSTM1 intron 1.1
      Probe

<400> SEQUENCE: 135
ccctgacttt gtctgcacca gggaag                                26

<210> SEQ ID NO 136
<211> LENGTH: 20
<212> TYPE: DNA
<213> ORGANISM: Artificial Sequence
<220> FEATURE:
<223> OTHER INFORMATION: GSTM1 intron 3.1
      Forward Primer

<400> SEQUENCE: 136
tctgtgtcca cctgcattcg                                       20

<210> SEQ ID NO 137
<211> LENGTH: 20
<212> TYPE: DNA
<213> ORGANISM: Artificial Sequence
<220> FEATURE:
<223> OTHER INFORMATION: GSTM1 intron 3.1
      Reverse Primer

<400> SEQUENCE: 137
ctgctcatgg caggactgaa                                       20

<210> SEQ ID NO 138
<211> LENGTH: 19
<212> TYPE: DNA
<213> ORGANISM: Artificial Sequence
<220> FEATURE:
<223> OTHER INFORMATION: GSTM1 intron 3.1
      Probe

<400> SEQUENCE: 138
tcatgtgaca gtattctta                                        19

<210> SEQ ID NO 139
<211> LENGTH: 22
<212> TYPE: DNA
<213> ORGANISM: Artificial Sequence
<220> FEATURE:
<223> OTHER INFORMATION: GSTM1 intron 5.1
      Forward Primer

<400> SEQUENCE: 139
cgactccaat gtcatgtcaa ca                                    22

<210> SEQ ID NO 140
<211> LENGTH: 18
<212> TYPE: DNA
<213> ORGANISM: Artificial Sequence
<220> FEATURE:
<223> OTHER INFORMATION: GSTM1 intron 5.1
      Reverse Primer

```
<400> SEQUENCE: 140 acccctgggat gcctggat                                                18

<210> SEQ ID NO 141
<211> LENGTH: 28
<212> TYPE: DNA
<213> ORGANISM: Artificial Sequence
<220> FEATURE:
<223> OTHER INFORMATION: GSTM1 intron 5.1
      Probe

<400> SEQUENCE: 141
agaggcaatt cccaccaacc ttaggaca                                      28

<210> SEQ ID NO 142
<211> LENGTH: 20
<212> TYPE: DNA
<213> ORGANISM: Artificial Sequence
<220> FEATURE:
<223> OTHER INFORMATION: GSTM1 intron 5.2
      Forward Primer

<400> SEQUENCE: 142
ggcaattccc accaacctta                                               20

<210> SEQ ID NO 143
<211> LENGTH: 29
<212> TYPE: DNA
<213> ORGANISM: Artificial Sequence
<220> FEATURE:
<223> OTHER INFORMATION: GSTM1 intron 5.2
      Reverse Primer

<400> SEQUENCE: 143
aaactttacc atacaggaac tgaatttct                                     29

<210> SEQ ID NO 144
<211> LENGTH: 22
<212> TYPE: DNA
<213> ORGANISM: Artificial Sequence
<220> FEATURE:
<223> OTHER INFORMATION: GSTM1 intron 5.2
      Probe

<400> SEQUENCE: 144
acacgatcca ggcatcccag gg                                            22

<210> SEQ ID NO 145
<211> LENGTH: 18
<212> TYPE: DNA
<213> ORGANISM: Artificial Sequence
<220> FEATURE:
<223> OTHER INFORMATION: GSTM1 intron 5.3
      Forward Primer

<400> SEQUENCE: 145
atggcaccct cgaattgc                                                 18

<210> SEQ ID NO 146
<211> LENGTH: 22
<212> TYPE: DNA
<213> ORGANISM: Artificial Sequence
<220> FEATURE:
<223> OTHER INFORMATION: GSTM1 intron 5.3
      Reverse Primer
```

```
<400> SEQUENCE: 146
tgcatgtcaa tgacagcact ca                                            22

<210> SEQ ID NO 147
<211> LENGTH: 19
<212> TYPE: DNA
<213> ORGANISM: Artificial Sequence
<220> FEATURE:
<223> OTHER INFORMATION: GSTM1 intron 5.3
      Probe

<400> SEQUENCE: 147
tcttctcctc aacagtttt                                                19

<210> SEQ ID NO 148
<211> LENGTH: 19
<212> TYPE: DNA
<213> ORGANISM: Artificial Sequence
<220> FEATURE:
<223> OTHER INFORMATION: GSTM1 intron 7.2
      Forward Primer

<400> SEQUENCE: 148
gcctccctgt ggaaaagga                                                19

<210> SEQ ID NO 149
<211> LENGTH: 18
<212> TYPE: DNA
<213> ORGANISM: Artificial Sequence
<220> FEATURE:
<223> OTHER INFORMATION: GSTM1 intron 7.2
      Reverse Primer

<400> SEQUENCE: 149
tcacaccagg ccctgtca                                                 18

<210> SEQ ID NO 150
<211> LENGTH: 19
<212> TYPE: DNA
<213> ORGANISM: Artificial Sequence
<220> FEATURE:
<223> OTHER INFORMATION: GSTM1 intron 7.2
      Probe

<400> SEQUENCE: 150
tccttgactg cacaaacag                                                19

<210> SEQ ID NO 151
<211> LENGTH: 21
<212> TYPE: DNA
<213> ORGANISM: Artificial Sequence
<220> FEATURE:
<223> OTHER INFORMATION: GSTM2 gene.1
      Forward Primer

<400> SEQUENCE: 151
gcaggaacga gaggaggaga t                                             21

<210> SEQ ID NO 152
<211> LENGTH: 20
<212> TYPE: DNA
<213> ORGANISM: Artificial Sequence
<220> FEATURE:
<223> OTHER INFORMATION: GSTM2 gene.1
      Reverse Primer

<400> SEQUENCE: 152
```
cagctcgggt cagagatgga                                               20

<210> SEQ ID NO 153
<211> LENGTH: 26
<212> TYPE: DNA
<213> ORGANISM: Artificial Sequence
<220> FEATURE:
<223> OTHER INFORMATION: GSTM2 gene.1
      Probe

<400> SEQUENCE: 153
ctccccttgt gcagagtcgt cacaaa                                        26

<210> SEQ ID NO 154
<211> LENGTH: 19
<212> TYPE: DNA
<213> ORGANISM: Artificial Sequence
<220> FEATURE:
<223> OTHER INFORMATION: GSTM2 gene.4
      Forward Primer

<400> SEQUENCE: 154
ctgggctgtg aggctgaga                                                19

<210> SEQ ID NO 155
<211> LENGTH: 21
<212> TYPE: DNA
<213> ORGANISM: Artificial Sequence
<220> FEATURE:
<223> OTHER INFORMATION: GSTM2 gene.4
      Reverse Primer

<400> SEQUENCE: 155
gcgaatctgc tccttttctg a                                             21

<210> SEQ ID NO 156
<211> LENGTH: 27
<212> TYPE: DNA
<213> ORGANISM: Artificial Sequence
<220> FEATURE:
<223> OTHER INFORMATION: GSTM2 gene.4
      Probe

<400> SEQUENCE: 156
cccgcctacc ctcgtaaagc agattca                                       27

<210> SEQ ID NO 157
<211> LENGTH: 21
<212> TYPE: DNA
<213> ORGANISM: Artificial Sequence
<220> FEATURE:
<223> OTHER INFORMATION: GSTM3.2
      Forward Primer

<400> SEQUENCE: 157
caatgccatc ttgcgctaca t                                             21

<210> SEQ ID NO 158
<211> LENGTH: 25
<212> TYPE: DNA
<213> ORGANISM: Artificial Sequence
<220> FEATURE:
<223> OTHER INFORMATION: GSTM3.2
      Reverse Primer

<400> SEQUENCE: 158
gtccactcga atcttttctt cttca                                          25

<210> SEQ ID NO 159
<211> LENGTH: 27
<212> TYPE: DNA
<213> ORGANISM: Artificial Sequence
<220> FEATURE:
<223> OTHER INFORMATION: GSTM3.2
      Probe

<400> SEQUENCE: 159
ctcgcaagca caacatgtgt ggtgaga                                        27

<210> SEQ ID NO 160
<211> LENGTH: 24
<212> TYPE: DNA
<213> ORGANISM: Artificial Sequence
<220> FEATURE:
<223> OTHER INFORMATION: GSTM3.5
      Forward Primer

<400> SEQUENCE: 160
ccagaagcca aggatctctc tagt                                           24

<210> SEQ ID NO 161
<211> LENGTH: 25
<212> TYPE: DNA
<213> ORGANISM: Artificial Sequence
<220> FEATURE:
<223> OTHER INFORMATION: GSTM3.5
      Reverse Primer

<400> SEQUENCE: 161
tattcctcct gacatcactg ggtat                                          25

<210> SEQ ID NO 162
<211> LENGTH: 23
<212> TYPE: DNA
<213> ORGANISM: Artificial Sequence
<220> FEATURE:
<223> OTHER INFORMATION: GSTM3.5
      Probe

<400> SEQUENCE: 162
tgccatttgg gccctctgac cat                                            23

<210> SEQ ID NO 163
<211> LENGTH: 23
<212> TYPE: DNA
<213> ORGANISM: Artificial Sequence
<220> FEATURE:
<223> OTHER INFORMATION: GSTM3.6
      Forward Primer

<400> SEQUENCE: 163
tcacagtttc cctagtcctc gaa                                            23

<210> SEQ ID NO 164
<211> LENGTH: 22
<212> TYPE: DNA
<213> ORGANISM: Artificial Sequence
<220> FEATURE:
<223> OTHER INFORMATION: GSTM3.6
      Reverse Primer

<400> SEQUENCE: 164
cgaatatccc agtacccgag aa                                             22

```
<210> SEQ ID NO 165
<211> LENGTH: 23
<212> TYPE: DNA
<213> ORGANISM: Artificial Sequence
<220> FEATURE:
<223> OTHER INFORMATION: GSTM3.6
      Probe

<400> SEQUENCE: 165
cccgtcacca tgtcgtgcga gtc                                              23

<210> SEQ ID NO 166
<211> LENGTH: 19
<212> TYPE: DNA
<213> ORGANISM: Artificial Sequence
<220> FEATURE:
<223> OTHER INFORMATION: GSTM4.1
      Forward Primer

<400> SEQUENCE: 166
cggaccttgc tccctgaac                                                   19

<210> SEQ ID NO 167
<211> LENGTH: 18
<212> TYPE: DNA
<213> ORGANISM: Artificial Sequence
<220> FEATURE:
<223> OTHER INFORMATION: GSTM4.1
      Reverse Primer

<400> SEQUENCE: 167
cggagcaggt tgctggat                                                    18

<210> SEQ ID NO 168
<211> LENGTH: 25
<212> TYPE: DNA
<213> ORGANISM: Artificial Sequence
<220> FEATURE:
<223> OTHER INFORMATION: GSTM4.1
      Probe

<400> SEQUENCE: 168
agtaagatcc accgccacct ccgag                                            25

<210> SEQ ID NO 169
<211> LENGTH: 20
<212> TYPE: DNA
<213> ORGANISM: Artificial Sequence
<220> FEATURE:
<223> OTHER INFORMATION: GSTM5.1
      Forward Primer

<400> SEQUENCE: 169
tccctgaggc tcccttgact                                                  20

<210> SEQ ID NO 170
<211> LENGTH: 22
<212> TYPE: DNA
<213> ORGANISM: Artificial Sequence
<220> FEATURE:
<223> OTHER INFORMATION: GSTM5.1
      Reverse Primer

<400> SEQUENCE: 170
ggctgtggac aacagaagac aa                                               22
```

<210> SEQ ID NO 171
<211> LENGTH: 25
<212> TYPE: DNA
<213> ORGANISM: Artificial Sequence
<220> FEATURE:
<223> OTHER INFORMATION: GSTM5.1
      Probe

<400> SEQUENCE: 171
ccacccacaa ttcgagcaca gtcct                                          25

<210> SEQ ID NO 172
<211> LENGTH: 21
<212> TYPE: DNA
<213> ORGANISM: Artificial Sequence
<220> FEATURE:
<223> OTHER INFORMATION: GSTM5.2
      Forward Primer

<400> SEQUENCE: 172
gaaaggtgct ctgtgccaag t                                              21

<210> SEQ ID NO 173
<211> LENGTH: 21
<212> TYPE: DNA
<213> ORGANISM: Artificial Sequence
<220> FEATURE:
<223> OTHER INFORMATION: GSTM5.2
      Reverse Primer

<400> SEQUENCE: 173
cctagcccct ctttgaacca t                                              21

<210> SEQ ID NO 174
<211> LENGTH: 27
<212> TYPE: DNA
<213> ORGANISM: Artificial Sequence
<220> FEATURE:
<223> OTHER INFORMATION: GSTM5.2
      Probe

<400> SEQUENCE: 174
attcgcgctc ctgtaggccg tctagaa                                        27

<210> SEQ ID NO 175
<211> LENGTH: 20
<212> TYPE: DNA
<213> ORGANISM: Artificial Sequence
<220> FEATURE:
<223> OTHER INFORMATION: GSTp.3
      Forward Primer

<400> SEQUENCE: 175
gagaccctgc tgtcccagaa                                                20

<210> SEQ ID NO 176
<211> LENGTH: 23
<212> TYPE: DNA
<213> ORGANISM: Artificial Sequence
<220> FEATURE:
<223> OTHER INFORMATION: GSTp.3
      Reverse Primer

<400> SEQUENCE: 176
ggttgtagtc agcgaaggag atc                                            23

```
<210> SEQ ID NO 177
<211> LENGTH: 26
<212> TYPE: DNA
<213> ORGANISM: Artificial Sequence
<220> FEATURE:
<223> OTHER INFORMATION: GSTp.3
      Probe

<400> SEQUENCE: 177
tcccacaatg aaggtcttgc ctccct                                          26

<210> SEQ ID NO 178
<211> LENGTH: 19
<212> TYPE: DNA
<213> ORGANISM: Artificial Sequence
<220> FEATURE:
<223> OTHER INFORMATION: GSTT1.3
      Forward Primer

<400> SEQUENCE: 178
caccatcccc accctgtct                                                  19

<210> SEQ ID NO 179
<211> LENGTH: 21
<212> TYPE: DNA
<213> ORGANISM: Artificial Sequence
<220> FEATURE:
<223> OTHER INFORMATION: GSTT1.3
      Reverse Primer

<400> SEQUENCE: 179
ggcctcagtg tgcatcattc t                                               21

<210> SEQ ID NO 180
<211> LENGTH: 23
<212> TYPE: DNA
<213> ORGANISM: Artificial Sequence
<220> FEATURE:
<223> OTHER INFORMATION: GSTT1.3
      Probe

<400> SEQUENCE: 180
cacagccgcc tgaaagccac aat                                             23

<210> SEQ ID NO 181
<211> LENGTH: 20
<212> TYPE: DNA
<213> ORGANISM: Artificial Sequence
<220> FEATURE:
<223> OTHER INFORMATION: GUS.1
      Forward Primer

<400> SEQUENCE: 181
cccactcagt agccaagtca                                                 20

<210> SEQ ID NO 182
<211> LENGTH: 20
<212> TYPE: DNA
<213> ORGANISM: Artificial Sequence
<220> FEATURE:
<223> OTHER INFORMATION: GUS.1
      Reverse Primer

<400> SEQUENCE: 182
cacgcaggtg gtatcagtct                                                 20

<210> SEQ ID NO 183
```

```
<211> LENGTH: 27
<212> TYPE: DNA
<213> ORGANISM: Artificial Sequence
<220> FEATURE:
<223> OTHER INFORMATION: GUS.1
      Probe

<400> SEQUENCE: 183
tcaagtaaac gggctgtttt ccaaaca                                       27

<210> SEQ ID NO 184
<211> LENGTH: 21
<212> TYPE: DNA
<213> ORGANISM: Artificial Sequence
<220> FEATURE:
<223> OTHER INFORMATION: HOXB13.1
      Forward Primer

<400> SEQUENCE: 184
cgtgccttat ggttactttg g                                             21

<210> SEQ ID NO 185
<211> LENGTH: 18
<212> TYPE: DNA
<213> ORGANISM: Artificial Sequence
<220> FEATURE:
<223> OTHER INFORMATION: HOXB13.1
      Reverse Primer

<400> SEQUENCE: 185
cacagggttt cagcgagc                                                 18

<210> SEQ ID NO 186
<211> LENGTH: 24
<212> TYPE: DNA
<213> ORGANISM: Artificial Sequence
<220> FEATURE:
<223> OTHER INFORMATION: HOXB13.1
      Probe

<400> SEQUENCE: 186
acactcggca ggagtagtac ccgc                                          24

<210> SEQ ID NO 187
<211> LENGTH: 18
<212> TYPE: DNA
<213> ORGANISM: Artificial Sequence
<220> FEATURE:
<223> OTHER INFORMATION: HSD17B1.1
      Forward Primer

<400> SEQUENCE: 187
ctggaccgca cggacatc                                                 18

<210> SEQ ID NO 188
<211> LENGTH: 18
<212> TYPE: DNA
<213> ORGANISM: Artificial Sequence
<220> FEATURE:
<223> OTHER INFORMATION: HSD17B1.1
      Reverse Primer

<400> SEQUENCE: 188
cgcctcgcga aagacttg                                                 18

<210> SEQ ID NO 189
<211> LENGTH: 25
```

```
<212> TYPE: DNA
<213> ORGANISM: Artificial Sequence
<220> FEATURE:
<223> OTHER INFORMATION: HSD17B1.1
      Probe

<400> SEQUENCE: 189
accgcttcta ccaataccte gccca                                          25

<210> SEQ ID NO 190
<211> LENGTH: 20
<212> TYPE: DNA
<213> ORGANISM: Artificial Sequence
<220> FEATURE:
<223> OTHER INFORMATION: HSD17B2.1
      Forward Primer

<400> SEQUENCE: 190
gctttccaag tggggaatta                                                20

<210> SEQ ID NO 191
<211> LENGTH: 20
<212> TYPE: DNA
<213> ORGANISM: Artificial Sequence
<220> FEATURE:
<223> OTHER INFORMATION: HSD17B2.1
      Reverse Primer

<400> SEQUENCE: 191
tgcctgcgat atttgttagg                                                20

<210> SEQ ID NO 192
<211> LENGTH: 24
<212> TYPE: DNA
<213> ORGANISM: Artificial Sequence
<220> FEATURE:
<223> OTHER INFORMATION: HSD17B2.1
      Probe

<400> SEQUENCE: 192
agttgcttcc atccaacctg gagg                                           24

<210> SEQ ID NO 193
<211> LENGTH: 20
<212> TYPE: DNA
<213> ORGANISM: Artificial Sequence
<220> FEATURE:
<223> OTHER INFORMATION: HSD17B4.1
      Forward Primer

<400> SEQUENCE: 193
ttgtcctttg gctttgtcac                                                20

<210> SEQ ID NO 194
<211> LENGTH: 19
<212> TYPE: DNA
<213> ORGANISM: Artificial Sequence
<220> FEATURE:
<223> OTHER INFORMATION: HSD17B4.1
      Reverse Primer

<400> SEQUENCE: 194
caatccatcc tgctccaac                                                 19

<210> SEQ ID NO 195
<211> LENGTH: 25
<212> TYPE: DNA
```

```
<213> ORGANISM: Artificial Sequence
<220> FEATURE:
<223> OTHER INFORMATION: HSD17B4.1
      Probe

<400> SEQUENCE: 195
caaacaagcc accattctcc tcaca                                            25

<210> SEQ ID NO 196
<211> LENGTH: 20
<212> TYPE: DNA
<213> ORGANISM: Artificial Sequence
<220> FEATURE:
<223> OTHER INFORMATION: IL17RB.2
      Forward Primer

<400> SEQUENCE: 196
accctctggt ggtaaatgga                                                  20

<210> SEQ ID NO 197
<211> LENGTH: 20
<212> TYPE: DNA
<213> ORGANISM: Artificial Sequence
<220> FEATURE:
<223> OTHER INFORMATION: IL17RB.2
      Reverse Primer

<400> SEQUENCE: 197
ggccccaatg aaatagactg                                                  20

<210> SEQ ID NO 198
<211> LENGTH: 24
<212> TYPE: DNA
<213> ORGANISM: Artificial Sequence
<220> FEATURE:
<223> OTHER INFORMATION: IL17RB.2
      Probe

<400> SEQUENCE: 198
tcggcttccc tgtagagctg aaca                                             24

<210> SEQ ID NO 199
<211> LENGTH: 20
<212> TYPE: DNA
<213> ORGANISM: Artificial Sequence
<220> FEATURE:
<223> OTHER INFORMATION: IMMT.1
      Forward Primer

<400> SEQUENCE: 199
ctgcctatgc cagactcaga                                                  20

<210> SEQ ID NO 200
<211> LENGTH: 20
<212> TYPE: DNA
<213> ORGANISM: Artificial Sequence
<220> FEATURE:
<223> OTHER INFORMATION: IMMT.1
      Reverse Primer

<400> SEQUENCE: 200
gcttttctgg cttcctcttc                                                  20

<210> SEQ ID NO 201
<211> LENGTH: 24
<212> TYPE: DNA
<213> ORGANISM: Artificial Sequence
```

<220> FEATURE:
<223> OTHER INFORMATION: IMMT.1
       Probe

<400> SEQUENCE: 201
caactgcatg gctctgaaca gcct                                              24

<210> SEQ ID NO 202
<211> LENGTH: 19
<212> TYPE: DNA
<213> ORGANISM: Artificial Sequence
<220> FEATURE:
<223> OTHER INFORMATION: Ki-67.2
       Forward Primer

<400> SEQUENCE: 202
cggactttgg gtgcgactt                                                    19

<210> SEQ ID NO 203
<211> LENGTH: 24
<212> TYPE: DNA
<213> ORGANISM: Artificial Sequence
<220> FEATURE:
<223> OTHER INFORMATION: Ki-67.2
       Reverse Primer

<400> SEQUENCE: 203
ttacaactct tccactggga cgat                                              24

<210> SEQ ID NO 204
<211> LENGTH: 23
<212> TYPE: DNA
<213> ORGANISM: Artificial Sequence
<220> FEATURE:
<223> OTHER INFORMATION: Ki-67.2
       Probe

<400> SEQUENCE: 204
ccacttgtcg aaccaccgct cgt                                               23

<210> SEQ ID NO 205
<211> LENGTH: 20
<212> TYPE: DNA
<213> ORGANISM: Artificial Sequence
<220> FEATURE:
<223> OTHER INFORMATION: LIPA.1
       Forward Primer

<400> SEQUENCE: 205
ccagttgtct tcctgcaaca                                                   20

<210> SEQ ID NO 206
<211> LENGTH: 20
<212> TYPE: DNA
<213> ORGANISM: Artificial Sequence
<220> FEATURE:
<223> OTHER INFORMATION: LIPA.1
       Reverse Primer

<400> SEQUENCE: 206
ctgttggcaa ggtttgtgac                                                   20

<210> SEQ ID NO 207
<211> LENGTH: 28
<212> TYPE: DNA
<213> ORGANISM: Artificial Sequence
<220> FEATURE:

<223> OTHER INFORMATION: LIPA.1
       Probe

<400> SEQUENCE: 207
ccagttacta gaatctgcca gcaagcca                                          28

<210> SEQ ID NO 208
<211> LENGTH: 20
<212> TYPE: DNA
<213> ORGANISM: Artificial Sequence
<220> FEATURE:
<223> OTHER INFORMATION: MDH2.1
       Forward Primer

<400> SEQUENCE: 208
ccaacacctt tgttgcagag                                                   20

<210> SEQ ID NO 209
<211> LENGTH: 20
<212> TYPE: DNA
<213> ORGANISM: Artificial Sequence
<220> FEATURE:
<223> OTHER INFORMATION: MDH2.1
       Reverse Primer

<400> SEQUENCE: 209
caatgacagg gacgttgact                                                   20

<210> SEQ ID NO 210
<211> LENGTH: 23
<212> TYPE: DNA
<213> ORGANISM: Artificial Sequence
<220> FEATURE:
<223> OTHER INFORMATION: MDH2.1
       Probe

<400> SEQUENCE: 210
cgagctggat ccaaccctt cag                                                23

<210> SEQ ID NO 211
<211> LENGTH: 21
<212> TYPE: DNA
<213> ORGANISM: Artificial Sequence
<220> FEATURE:
<223> OTHER INFORMATION: mGST1.2
       Forward Primer

<400> SEQUENCE: 211
acggatctac cacaccattg c                                                 21

<210> SEQ ID NO 212
<211> LENGTH: 26
<212> TYPE: DNA
<213> ORGANISM: Artificial Sequence
<220> FEATURE:
<223> OTHER INFORMATION: mGST1.2
       Reverse Primer

<400> SEQUENCE: 212
tccatatcca acaaaaaaac tcaaag                                            26

<210> SEQ ID NO 213
<211> LENGTH: 22
<212> TYPE: DNA
<213> ORGANISM: Artificial Sequence
<220> FEATURE:
<223> OTHER INFORMATION: mGST1.2

Probe

<400> SEQUENCE: 213
tttgacaccc cttccccagc ca                                           22

<210> SEQ ID NO 214
<211> LENGTH: 21
<212> TYPE: DNA
<213> ORGANISM: Artificial Sequence
<220> FEATURE:
<223> OTHER INFORMATION: MGST3.1
      Forward Primer

<400> SEQUENCE: 214
agctgttgga ggtgtttacc a                                            21

<210> SEQ ID NO 215
<211> LENGTH: 18
<212> TYPE: DNA
<213> ORGANISM: Artificial Sequence
<220> FEATURE:
<223> OTHER INFORMATION: MGST3.1
      Reverse Primer

<400> SEQUENCE: 215
tcgtccaaca atccaggc                                                18

<210> SEQ ID NO 216
<211> LENGTH: 24
<212> TYPE: DNA
<213> ORGANISM: Artificial Sequence
<220> FEATURE:
<223> OTHER INFORMATION: MGST3.1
      Probe

<400> SEQUENCE: 216
aagcccaggc cagaagctat acgc                                         24

<210> SEQ ID NO 217
<211> LENGTH: 20
<212> TYPE: DNA
<213> ORGANISM: Artificial Sequence
<220> FEATURE:
<223> OTHER INFORMATION: MMTV-like env.3
      Forward Primer

<400> SEQUENCE: 217
ccatacgtgc tgctacctgt                                              20

<210> SEQ ID NO 218
<211> LENGTH: 21
<212> TYPE: DNA
<213> ORGANISM: Artificial Sequence
<220> FEATURE:
<223> OTHER INFORMATION: MMTV-like env.3
      Reverse Primer

<400> SEQUENCE: 218
cctaaaggtt tgaatggcag a                                            21

<210> SEQ ID NO 219
<211> LENGTH: 29
<212> TYPE: DNA
<213> ORGANISM: Artificial Sequence
<220> FEATURE:
<223> OTHER INFORMATION: MMTV-like env.3
      Probe

<400> SEQUENCE: 219
tcatcaaacc atggttcatc accaatatc                                          29

<210> SEQ ID NO 220
<211> LENGTH: 24
<212> TYPE: DNA
<213> ORGANISM: Artificial Sequence
<220> FEATURE:
<223> OTHER INFORMATION: MPV17.1
      Forward Primer

<400> SEQUENCE: 220
ccaatgtgtt gctgttatct ggaa                                               24

<210> SEQ ID NO 221
<211> LENGTH: 22
<212> TYPE: DNA
<213> ORGANISM: Artificial Sequence
<220> FEATURE:
<223> OTHER INFORMATION: MPV17.1
      Reverse Primer

<400> SEQUENCE: 221
atggagtgag gcaggcttag ag                                                 22

<210> SEQ ID NO 222
<211> LENGTH: 26
<212> TYPE: DNA
<213> ORGANISM: Artificial Sequence
<220> FEATURE:
<223> OTHER INFORMATION: MPV17.1
      Probe

<400> SEQUENCE: 222
tcctacctgt cctggaaggc acatcg                                             26

<210> SEQ ID NO 223
<211> LENGTH: 22
<212> TYPE: DNA
<213> ORGANISM: Artificial Sequence
<220> FEATURE:
<223> OTHER INFORMATION: MPV.1
      Forward Primer

<400> SEQUENCE: 223
acgagaacga gggcatctat gt                                                 22

<210> SEQ ID NO 224
<211> LENGTH: 22
<212> TYPE: DNA
<213> ORGANISM: Artificial Sequence
<220> FEATURE:
<223> OTHER INFORMATION: MPV.1
      Reverse Primer

<400> SEQUENCE: 224
gcatgtaggt gcttccaatc ac                                                 22

<210> SEQ ID NO 225
<211> LENGTH: 25
<212> TYPE: DNA
<213> ORGANISM: Artificial Sequence
<220> FEATURE:
<223> OTHER INFORMATION: MPV.1
      Probe

```
<400> SEQUENCE: 225
cgcacctttc cggtcttgac atcct                                          25

<210> SEQ ID NO 226
<211> LENGTH: 20
<212> TYPE: DNA
<213> ORGANISM: Artificial Sequence
<220> FEATURE:
<223> OTHER INFORMATION: NAT1.1
      Forward Primer

<400> SEQUENCE: 226
tggttttgag accacgatgt                                                20

<210> SEQ ID NO 227
<211> LENGTH: 20
<212> TYPE: DNA
<213> ORGANISM: Artificial Sequence
<220> FEATURE:
<223> OTHER INFORMATION: NAT1.1
      Reverse Primer

<400> SEQUENCE: 227
tgaatcatgc cagtgctgta                                                20

<210> SEQ ID NO 228
<211> LENGTH: 26
<212> TYPE: DNA
<213> ORGANISM: Artificial Sequence
<220> FEATURE:
<223> OTHER INFORMATION: NAT1.1
      Probe

<400> SEQUENCE: 228
tggagtgctg taaacatacc ctccca                                         26

<210> SEQ ID NO 229
<211> LENGTH: 25
<212> TYPE: DNA
<213> ORGANISM: Artificial Sequence
<220> FEATURE:
<223> OTHER INFORMATION: NAT2.1
      Forward Primer

<400> SEQUENCE: 229
taactgacat tcttgagcac cagat                                          25

<210> SEQ ID NO 230
<211> LENGTH: 18
<212> TYPE: DNA
<213> ORGANISM: Artificial Sequence
<220> FEATURE:
<223> OTHER INFORMATION: NAT2.1
      Reverse Primer

<400> SEQUENCE: 230
atggcttgcc cacaatgc                                                  18

<210> SEQ ID NO 231
<211> LENGTH: 28
<212> TYPE: DNA
<213> ORGANISM: Artificial Sequence
<220> FEATURE:
<223> OTHER INFORMATION: NAT2.1
      Probe

<400> SEQUENCE: 231
```
cgggctgttc cctttgagaa ccttaaca                                          28

<210> SEQ ID NO 232
<211> LENGTH: 20
<212> TYPE: DNA
<213> ORGANISM: Artificial Sequence
<220> FEATURE:
<223> OTHER INFORMATION: NCOA2.1
      Forward Primer

<400> SEQUENCE: 232
agtgacctcc gtgcctacgt                                                   20

<210> SEQ ID NO 233
<211> LENGTH: 20
<212> TYPE: DNA
<213> ORGANISM: Artificial Sequence
<220> FEATURE:
<223> OTHER INFORMATION: NCOA2.1
      Reverse Primer

<400> SEQUENCE: 233
ctcccctcag agcaggatca                                                   20

<210> SEQ ID NO 234
<211> LENGTH: 21
<212> TYPE: DNA
<213> ORGANISM: Artificial Sequence
<220> FEATURE:
<223> OTHER INFORMATION: NCOA2.1
      Probe

<400> SEQUENCE: 234
cctccatggg tcccgagcag g                                                 21

<210> SEQ ID NO 235
<211> LENGTH: 19
<212> TYPE: DNA
<213> ORGANISM: Artificial Sequence
<220> FEATURE:
<223> OTHER INFORMATION: NDUFA7.1
      Forward Primer

<400> SEQUENCE: 235
gcagctacgc taccaggag                                                    19

<210> SEQ ID NO 236
<211> LENGTH: 20
<212> TYPE: DNA
<213> ORGANISM: Artificial Sequence
<220> FEATURE:
<223> OTHER INFORMATION: NDUFA7.1
      Reverse Primer

<400> SEQUENCE: 236
ggagagcttg tggctaggac                                                   20

<210> SEQ ID NO 237
<211> LENGTH: 24
<212> TYPE: DNA
<213> ORGANISM: Artificial Sequence
<220> FEATURE:
<223> OTHER INFORMATION: NDUFA7.1
      Probe

<400> SEQUENCE: 237
tctccaagcg aactcagcct cctc                                          24

<210> SEQ ID NO 238
<211> LENGTH: 18
<212> TYPE: DNA
<213> ORGANISM: Artificial Sequence
<220> FEATURE:
<223> OTHER INFORMATION: NQO1.1
      Forward Primer

<400> SEQUENCE: 238
cagcagacgc ccgaattc                                                 18

<210> SEQ ID NO 239
<211> LENGTH: 24
<212> TYPE: DNA
<213> ORGANISM: Artificial Sequence
<220> FEATURE:
<223> OTHER INFORMATION: NQO1.1
      Reverse Primer

<400> SEQUENCE: 239
tggtgtctca tcccaaatat tctc                                          24

<210> SEQ ID NO 240
<211> LENGTH: 27
<212> TYPE: DNA
<213> ORGANISM: Artificial Sequence
<220> FEATURE:
<223> OTHER INFORMATION: NQO1.1
      Probe

<400> SEQUENCE: 240
aggcgtttct tccatccttc caggatt                                       27

<210> SEQ ID NO 241
<211> LENGTH: 19
<212> TYPE: DNA
<213> ORGANISM: Artificial Sequence
<220> FEATURE:
<223> OTHER INFORMATION: NQO2.1
      Forward Primer

<400> SEQUENCE: 241
agcgctcctt tccgtaacc                                                19

<210> SEQ ID NO 242
<211> LENGTH: 24
<212> TYPE: DNA
<213> ORGANISM: Artificial Sequence
<220> FEATURE:
<223> OTHER INFORMATION: NQO2.1
      Reverse Primer

<400> SEQUENCE: 242
tccattgact cctgtcttcg tgta                                          24

<210> SEQ ID NO 243
<211> LENGTH: 19
<212> TYPE: DNA
<213> ORGANISM: Artificial Sequence
<220> FEATURE:
<223> OTHER INFORMATION: NQO2.1
      Probe

<400> SEQUENCE: 243
atctcggccg tgcctcccg                                                19

-continued

<210> SEQ ID NO 244
<211> LENGTH: 20
<212> TYPE: DNA
<213> ORGANISM: Artificial Sequence
<220> FEATURE:
<223> OTHER INFORMATION: P53.2
     Forward Primer

<400> SEQUENCE: 244
ctttgaaccc ttgcttgcaa                                              20

<210> SEQ ID NO 245
<211> LENGTH: 18
<212> TYPE: DNA
<213> ORGANISM: Artificial Sequence
<220> FEATURE:
<223> OTHER INFORMATION: P53.2
     Reverse Primer

<400> SEQUENCE: 245
cccgggacaa agcaaatg                                                18

<210> SEQ ID NO 246
<211> LENGTH: 25
<212> TYPE: DNA
<213> ORGANISM: Artificial Sequence
<220> FEATURE:
<223> OTHER INFORMATION: P53.2
     Probe

<400> SEQUENCE: 246
aagtcctggg tgcttctgac gcaca                                        25

<210> SEQ ID NO 247
<211> LENGTH: 19
<212> TYPE: DNA
<213> ORGANISM: Artificial Sequence
<220> FEATURE:
<223> OTHER INFORMATION: PAI1.3
     Forward Primer

<400> SEQUENCE: 247
ccgcaacgtg gttttctca                                               19

<210> SEQ ID NO 248
<211> LENGTH: 21
<212> TYPE: DNA
<213> ORGANISM: Artificial Sequence
<220> FEATURE:
<223> OTHER INFORMATION: PAI1.3
     Reverse Primer

<400> SEQUENCE: 248
tgctgggttt ctcctcctgt t                                            21

<210> SEQ ID NO 249
<211> LENGTH: 22
<212> TYPE: DNA
<213> ORGANISM: Artificial Sequence
<220> FEATURE:
<223> OTHER INFORMATION: PAI1.3
     Probe

<400> SEQUENCE: 249
ctcggtgttg gccatgctcc ag                                           22

<210> SEQ ID NO 250
<211> LENGTH: 20
<212> TYPE: DNA
<213> ORGANISM: Artificial Sequence
<220> FEATURE:
<223> OTHER INFORMATION: PR.6
      Forward Primer

<400> SEQUENCE: 250
gcatcaggct gtcattatgg                                                    20

<210> SEQ ID NO 251
<211> LENGTH: 20
<212> TYPE: DNA
<213> ORGANISM: Artificial Sequence
<220> FEATURE:
<223> OTHER INFORMATION: PR.6
      Reverse Primer

<400> SEQUENCE: 251
agtagttgtg ctgcccttcc                                                    20

<210> SEQ ID NO 252
<211> LENGTH: 28
<212> TYPE: DNA
<213> ORGANISM: Artificial Sequence
<220> FEATURE:
<223> OTHER INFORMATION: PR.6
      Probe

<400> SEQUENCE: 252
tgtccttacc tgtgggagct gtaaggtc                                           28

<210> SEQ ID NO 253
<211> LENGTH: 20
<212> TYPE: DNA
<213> ORGANISM: Artificial Sequence
<220> FEATURE:
<223> OTHER INFORMATION: PR.12
      Forward Primer

<400> SEQUENCE: 253
gttccatccc aaagaacctg                                                    20

<210> SEQ ID NO 254
<211> LENGTH: 21
<212> TYPE: DNA
<213> ORGANISM: Artificial Sequence
<220> FEATURE:
<223> OTHER INFORMATION: PR.12
      Reverse Primer

<400> SEQUENCE: 254
gaaactctgg agttggcatt t                                                  21

<210> SEQ ID NO 255
<211> LENGTH: 28
<212> TYPE: DNA
<213> ORGANISM: Artificial Sequence
<220> FEATURE:
<223> OTHER INFORMATION: PR.12
      Probe

<400> SEQUENCE: 255
ccacccgtta ttctgaatgc tactctca                                           28

```
<210> SEQ ID NO 256
<211> LENGTH: 23
<212> TYPE: DNA
<213> ORGANISM: Artificial Sequence
<220> FEATURE:
<223> OTHER INFORMATION: PRAME.3
      Forward Primer

<400> SEQUENCE: 256
tctccatatc tgccttgcag agt                                              23

<210> SEQ ID NO 257
<211> LENGTH: 19
<212> TYPE: DNA
<213> ORGANISM: Artificial Sequence
<220> FEATURE:
<223> OTHER INFORMATION: PRAME.3
      Reverse Primer

<400> SEQUENCE: 257
gcacgtgggt cagattgct                                                   19

<210> SEQ ID NO 258
<211> LENGTH: 22
<212> TYPE: DNA
<213> ORGANISM: Artificial Sequence
<220> FEATURE:
<223> OTHER INFORMATION: PRAME.3
      Probe

<400> SEQUENCE: 258
tcctgcagca cctcatcggg ct                                               22

<210> SEQ ID NO 259
<211> LENGTH: 21
<212> TYPE: DNA
<213> ORGANISM: Artificial Sequence
<220> FEATURE:
<223> OTHER INFORMATION: PRAME.4
      Forward Primer

<400> SEQUENCE: 259
ccactgctcc cagcttacaa c                                                21

<210> SEQ ID NO 260
<211> LENGTH: 22
<212> TYPE: DNA
<213> ORGANISM: Artificial Sequence
<220> FEATURE:
<223> OTHER INFORMATION: PRAME.4
      Reverse Primer

<400> SEQUENCE: 260
ctgcaaggca gatatggaga tg                                               22

<210> SEQ ID NO 261
<211> LENGTH: 19
<212> TYPE: DNA
<213> ORGANISM: Artificial Sequence
<220> FEATURE:
<223> OTHER INFORMATION: PRAME.4
      Probe

<400> SEQUENCE: 261
aattcccgta gaagcttaa                                                   19

<210> SEQ ID NO 262
```

```
<211> LENGTH: 25
<212> TYPE: DNA
<213> ORGANISM: Artificial Sequence
<220> FEATURE:
<223> OTHER INFORMATION: PRAME intron 5.1
      Forward Primer

<400> SEQUENCE: 262
atcaggcaca gagatagagg tgact                                        25

<210> SEQ ID NO 263
<211> LENGTH: 21
<212> TYPE: DNA
<213> ORGANISM: Artificial Sequence
<220> FEATURE:
<223> OTHER INFORMATION: PRAME intron 5.1
      Reverse Primer

<400> SEQUENCE: 263
tctttcaact cgggcttcct t                                            21

<210> SEQ ID NO 264
<211> LENGTH: 14
<212> TYPE: DNA
<213> ORGANISM: Artificial Sequence
<220> FEATURE:
<223> OTHER INFORMATION: PRAME intron 5.1
      Probe

<400> SEQUENCE: 264
cccaggcagt ggca                                                    14

<210> SEQ ID NO 265
<211> LENGTH: 20
<212> TYPE: DNA
<213> ORGANISM: Artificial Sequence
<220> FEATURE:
<223> OTHER INFORMATION: PRDX2.1
      Forward Primer

<400> SEQUENCE: 265
ggtgtccttc gccagatcac                                              20

<210> SEQ ID NO 266
<211> LENGTH: 18
<212> TYPE: DNA
<213> ORGANISM: Artificial Sequence
<220> FEATURE:
<223> OTHER INFORMATION: PRDX2.1
      Reverse Primer

<400> SEQUENCE: 266
cagccgcaga gcctcatc                                                18

<210> SEQ ID NO 267
<211> LENGTH: 26
<212> TYPE: DNA
<213> ORGANISM: Artificial Sequence
<220> FEATURE:
<223> OTHER INFORMATION: PRDX2.1
      Probe

<400> SEQUENCE: 267
ttaatgattt gcctgtggga cgctcc                                       26

<210> SEQ ID NO 268
<211> LENGTH: 20
```

```
<212> TYPE: DNA
<213> ORGANISM: Artificial Sequence
<220> FEATURE:
<223> OTHER INFORMATION: PRDX3.1
      Forward Primer

<400> SEQUENCE: 268
tgaccccaat ggagtcatca                                               20

<210> SEQ ID NO 269
<211> LENGTH: 19
<212> TYPE: DNA
<213> ORGANISM: Artificial Sequence
<220> FEATURE:
<223> OTHER INFORMATION: PRDX3.1
      Reverse Primer

<400> SEQUENCE: 269
ccaagcggag ggtttcttc                                                19

<210> SEQ ID NO 270
<211> LENGTH: 27
<212> TYPE: DNA
<213> ORGANISM: Artificial Sequence
<220> FEATURE:
<223> OTHER INFORMATION: PRDX3.1
      Probe

<400> SEQUENCE: 270
catttgagcg tcaacgatct cccagtg                                       27

<210> SEQ ID NO 271
<211> LENGTH: 22
<212> TYPE: DNA
<213> ORGANISM: Artificial Sequence
<220> FEATURE:
<223> OTHER INFORMATION: PRDX4.1
      Forward Primer

<400> SEQUENCE: 271
ttacccattt ggcctggatt aa                                            22

<210> SEQ ID NO 272
<211> LENGTH: 25
<212> TYPE: DNA
<213> ORGANISM: Artificial Sequence
<220> FEATURE:
<223> OTHER INFORMATION: PRDX4.1
      Reverse Primer

<400> SEQUENCE: 272
ctgaaagaag tggaatcctt attgg                                         25

<210> SEQ ID NO 273
<211> LENGTH: 26
<212> TYPE: DNA
<213> ORGANISM: Artificial Sequence
<220> FEATURE:
<223> OTHER INFORMATION: PRDX4.1
      Probe

<400> SEQUENCE: 273
ccaagtcctc cttgtcttcg aggggt                                        26

<210> SEQ ID NO 274
<211> LENGTH: 20
<212> TYPE: DNA
```

```
<213> ORGANISM: Artificial Sequence
<220> FEATURE:
<223> OTHER INFORMATION: PRDX6.1
      Forward Primer

<400> SEQUENCE: 274
ctgtgagcca gaggatgtca                                              20

<210> SEQ ID NO 275
<211> LENGTH: 20
<212> TYPE: DNA
<213> ORGANISM: Artificial Sequence
<220> FEATURE:
<223> OTHER INFORMATION: PRDX6.1
      Reverse Primer

<400> SEQUENCE: 275
tgtgatgaca ccaggatgtg                                              20

<210> SEQ ID NO 276
<211> LENGTH: 24
<212> TYPE: DNA
<213> ORGANISM: Artificial Sequence
<220> FEATURE:
<223> OTHER INFORMATION: PRDX6.1
      Probe

<400> SEQUENCE: 276
ctgccaattg tgttttcctg cagc                                         24

<210> SEQ ID NO 277
<211> LENGTH: 24
<212> TYPE: DNA
<213> ORGANISM: Artificial Sequence
<220> FEATURE:
<223> OTHER INFORMATION: RPLPO.2
      Forward Primer

<400> SEQUENCE: 277
ccattctatc atcaacgggt acaa                                         24

<210> SEQ ID NO 278
<211> LENGTH: 23
<212> TYPE: DNA
<213> ORGANISM: Artificial Sequence
<220> FEATURE:
<223> OTHER INFORMATION: RPLPO.2
      Reverse Primer

<400> SEQUENCE: 278
tcagcaagtg ggaaggtgta atc                                          23

<210> SEQ ID NO 279
<211> LENGTH: 25
<212> TYPE: DNA
<213> ORGANISM: Artificial Sequence
<220> FEATURE:
<223> OTHER INFORMATION: RPLPO.2
      Probe

<400> SEQUENCE: 279
tctccacaga caaggccagg actcg                                        25

<210> SEQ ID NO 280
<211> LENGTH: 20
<212> TYPE: DNA
<213> ORGANISM: Artificial Sequence
```

```
<220> FEATURE:
<223> OTHER INFORMATION: SC5DL.1
      Forward Primer

<400> SEQUENCE: 280
cgcctacata aacctcacca                                                20

<210> SEQ ID NO 281
<211> LENGTH: 21
<212> TYPE: DNA
<213> ORGANISM: Artificial Sequence
<220> FEATURE:
<223> OTHER INFORMATION: SC5DL.1
      Reverse Primer

<400> SEQUENCE: 281
ccatcaatag ggtgaaaagc a                                              21

<210> SEQ ID NO 282
<211> LENGTH: 29
<212> TYPE: DNA
<213> ORGANISM: Artificial Sequence
<220> FEATURE:
<223> OTHER INFORMATION: SC5DL.1
      Probe

<400> SEQUENCE: 282
tggaagattc ctactccatt tgcaagtca                                      29

<210> SEQ ID NO 283
<211> LENGTH: 20
<212> TYPE: DNA
<213> ORGANISM: Artificial Sequence
<220> FEATURE:
<223> OTHER INFORMATION: SOD1.1
      Forward Primer

<400> SEQUENCE: 283
tgaagagagg catgttggag                                                20

<210> SEQ ID NO 284
<211> LENGTH: 20
<212> TYPE: DNA
<213> ORGANISM: Artificial Sequence
<220> FEATURE:
<223> OTHER INFORMATION: SOD1.1
      Reverse Primer

<400> SEQUENCE: 284
aatagacaca tcggccacac                                                20

<210> SEQ ID NO 285
<211> LENGTH: 24
<212> TYPE: DNA
<213> ORGANISM: Artificial Sequence
<220> FEATURE:
<223> OTHER INFORMATION: SOD1.1
      Probe

<400> SEQUENCE: 285
tttgtcagca gtcacattgc ccaa                                           24

<210> SEQ ID NO 286
<211> LENGTH: 21
<212> TYPE: DNA
<213> ORGANISM: Artificial Sequence
<220> FEATURE:
```

```
<223> OTHER INFORMATION: SOD2.1
      Forward Primer

<400> SEQUENCE: 286
gcttgtccaa atcaggatcc a                                              21

<210> SEQ ID NO 287
<211> LENGTH: 19
<212> TYPE: DNA
<213> ORGANISM: Artificial Sequence
<220> FEATURE:
<223> OTHER INFORMATION: SOD2.1
      Reverse Primer

<400> SEQUENCE: 287
agcgtgctcc cacacatca                                                 19

<210> SEQ ID NO 288
<211> LENGTH: 27
<212> TYPE: DNA
<213> ORGANISM: Artificial Sequence
<220> FEATURE:
<223> OTHER INFORMATION: SOD2.1
      Probe

<400> SEQUENCE: 288
aacaacaggc cttattccac tgctggg                                        27

<210> SEQ ID NO 289
<211> LENGTH: 20
<212> TYPE: DNA
<213> ORGANISM: Artificial Sequence
<220> FEATURE:
<223> OTHER INFORMATION: SOD3.1
      Forward Primer

<400> SEQUENCE: 289
ccataagccc tgagactccc                                                20

<210> SEQ ID NO 290
<211> LENGTH: 19
<212> TYPE: DNA
<213> ORGANISM: Artificial Sequence
<220> FEATURE:
<223> OTHER INFORMATION: SOD3.1
      Reverse Primer

<400> SEQUENCE: 290
taggaggaac ctgaaggcg                                                 19

<210> SEQ ID NO 291
<211> LENGTH: 24
<212> TYPE: DNA
<213> ORGANISM: Artificial Sequence
<220> FEATURE:
<223> OTHER INFORMATION: SOD3.1
      Probe

<400> SEQUENCE: 291
ttgacctgac gatcttcccc cttc                                           24

<210> SEQ ID NO 292
<211> LENGTH: 20
<212> TYPE: DNA
<213> ORGANISM: Artificial Sequence
<220> FEATURE:
<223> OTHER INFORMATION: SRD5A2.1
```

Forward Primer

<400> SEQUENCE: 292
gtaggtctcc tggcgttctg                                                  20

<210> SEQ ID NO 293
<211> LENGTH: 21
<212> TYPE: DNA
<213> ORGANISM: Artificial Sequence
<220> FEATURE:
<223> OTHER INFORMATION: SRD5A2.1
      Reverse Primer

<400> SEQUENCE: 293
tccctggaag ggtaggagta a                                                21

<210> SEQ ID NO 294
<211> LENGTH: 24
<212> TYPE: DNA
<213> ORGANISM: Artificial Sequence
<220> FEATURE:
<223> OTHER INFORMATION: SRD5A2.1
      Probe

<400> SEQUENCE: 294
agacaccact cagaatcccc aggc                                             24

<210> SEQ ID NO 295
<211> LENGTH: 20
<212> TYPE: DNA
<213> ORGANISM: Artificial Sequence
<220> FEATURE:
<223> OTHER INFORMATION: STK15.2
      Forward Primer

<400> SEQUENCE: 295
catcttccag gaggaccact                                                  20

<210> SEQ ID NO 296
<211> LENGTH: 20
<212> TYPE: DNA
<213> ORGANISM: Artificial Sequence
<220> FEATURE:
<223> OTHER INFORMATION: STK15.2
      Reverse Primer

<400> SEQUENCE: 296
tccgaccttc aatcatttca                                                  20

<210> SEQ ID NO 297
<211> LENGTH: 24
<212> TYPE: DNA
<213> ORGANISM: Artificial Sequence
<220> FEATURE:
<223> OTHER INFORMATION: STK15.2
      Probe

<400> SEQUENCE: 297
ctctgtggca ccctggacta cctg                                             24

<210> SEQ ID NO 298
<211> LENGTH: 20
<212> TYPE: DNA
<213> ORGANISM: Artificial Sequence
<220> FEATURE:
<223> OTHER INFORMATION: STK15.8
      Forward Primer

```
<400> SEQUENCE: 298
gccccctgaa atgattgaag                                               20

<210> SEQ ID NO 299
<211> LENGTH: 20
<212> TYPE: DNA
<213> ORGANISM: Artificial Sequence
<220> FEATURE:
<223> OTHER INFORMATION: STK15.8
      Reverse Primer

<400> SEQUENCE: 299
tccaaggctc cagagatcca                                               20

<210> SEQ ID NO 300
<211> LENGTH: 18
<212> TYPE: DNA
<213> ORGANISM: Artificial Sequence
<220> FEATURE:
<223> OTHER INFORMATION: STK15.8
      Probe

<400> SEQUENCE: 300
ttctcatcat gcatccga                                                 18

<210> SEQ ID NO 301
<211> LENGTH: 26
<212> TYPE: DNA
<213> ORGANISM: Artificial Sequence
<220> FEATURE:
<223> OTHER INFORMATION: STK15 intron 2.1
      Forward Primer

<400> SEQUENCE: 301
cattcacatt tataaaccca catgga                                        26

<210> SEQ ID NO 302
<211> LENGTH: 23
<212> TYPE: DNA
<213> ORGANISM: Artificial Sequence
<220> FEATURE:
<223> OTHER INFORMATION: STK15 intron 2.1
      Reverse Primer

<400> SEQUENCE: 302
aatccaaagt aaaggcggaa aga                                           23

<210> SEQ ID NO 303
<211> LENGTH: 16
<212> TYPE: DNA
<213> ORGANISM: Artificial Sequence
<220> FEATURE:
<223> OTHER INFORMATION: STK15 intron 2.1
      Probe

<400> SEQUENCE: 303
tggtcttgtc gggaat                                                   16

<210> SEQ ID NO 304
<211> LENGTH: 20
<212> TYPE: DNA
<213> ORGANISM: Artificial Sequence
<220> FEATURE:
<223> OTHER INFORMATION: STK15 intron 4.1
      Forward Primer
```

<400> SEQUENCE: 304
gcgaggaatg aacccacaga                                            20

<210> SEQ ID NO 305
<211> LENGTH: 25
<212> TYPE: DNA
<213> ORGANISM: Artificial Sequence
<220> FEATURE:
<223> OTHER INFORMATION: STK15 intron 4.1
      Reverse Primer

<400> SEQUENCE: 305
gcatgagaac cagtggattt agact                                      25

<210> SEQ ID NO 306
<211> LENGTH: 16
<212> TYPE: DNA
<213> ORGANISM: Artificial Sequence
<220> FEATURE:
<223> OTHER INFORMATION: STK15 intron 4.1
      Probe

<400> SEQUENCE: 306
cgctaaaagc aaaaga                                                16

<210> SEQ ID NO 307
<211> LENGTH: 19
<212> TYPE: DNA
<213> ORGANISM: Artificial Sequence
<220> FEATURE:
<223> OTHER INFORMATION: SULT1E1.1
      Forward Primer

<400> SEQUENCE: 307
atggtggctg gtcatccaa                                             19

<210> SEQ ID NO 308
<211> LENGTH: 24
<212> TYPE: DNA
<213> ORGANISM: Artificial Sequence
<220> FEATURE:
<223> OTHER INFORMATION: SULT1E1.1
      Reverse Primer

<400> SEQUENCE: 308
ataaggaacc tgtccttgca tgaa                                       24

<210> SEQ ID NO 309
<211> LENGTH: 30
<212> TYPE: DNA
<213> ORGANISM: Artificial Sequence
<220> FEATURE:
<223> OTHER INFORMATION: SULT1E1.1
      Probe

<400> SEQUENCE: 309
ttctccacaa actctggaaa ggatccagga                                 30

<210> SEQ ID NO 310
<211> LENGTH: 19
<212> TYPE: DNA
<213> ORGANISM: Artificial Sequence
<220> FEATURE:
<223> OTHER INFORMATION: SULT4A1.1
      Forward Primer

<400> SEQUENCE: 310
cacctgccct accgctttc                                                19

<210> SEQ ID NO 311
<211> LENGTH: 21
<212> TYPE: DNA
<213> ORGANISM: Artificial Sequence
<220> FEATURE:
<223> OTHER INFORMATION: SULT4A1.1
      Reverse Primer

<400> SEQUENCE: 311
gggttgcgag ccatatagat g                                             21

<210> SEQ ID NO 312
<211> LENGTH: 27
<212> TYPE: DNA
<213> ORGANISM: Artificial Sequence
<220> FEATURE:
<223> OTHER INFORMATION: SULT4A1.1
      Probe

<400> SEQUENCE: 312
cctctgacct ccacaatgga gactcca                                       27

<210> SEQ ID NO 313
<211> LENGTH: 20
<212> TYPE: DNA
<213> ORGANISM: Artificial Sequence
<220> FEATURE:
<223> OTHER INFORMATION: SURV.2
      Forward Primer

<400> SEQUENCE: 313
tgttttgatt cccgggctta                                               20

<210> SEQ ID NO 314
<211> LENGTH: 24
<212> TYPE: DNA
<213> ORGANISM: Artificial Sequence
<220> FEATURE:
<223> OTHER INFORMATION: SURV.2
      Reverse Primer

<400> SEQUENCE: 314
caaagctgtc agctctagca aaag                                          24

<210> SEQ ID NO 315
<211> LENGTH: 28
<212> TYPE: DNA
<213> ORGANISM: Artificial Sequence
<220> FEATURE:
<223> OTHER INFORMATION: SURV.2
      Probe

<400> SEQUENCE: 315
tgccttcttc ctccctcact tctcacct                                      28

<210> SEQ ID NO 316
<211> LENGTH: 19
<212> TYPE: DNA
<213> ORGANISM: Artificial Sequence
<220> FEATURE:
<223> OTHER INFORMATION: TBP.1
      Forward Primer

<400> SEQUENCE: 316
gcccgaaacg ccgaatata                                                19

<210> SEQ ID NO 317
<211> LENGTH: 23
<212> TYPE: DNA
<213> ORGANISM: Artificial Sequence
<220> FEATURE:
<223> OTHER INFORMATION: TBP.1
      Reverse Primer

<400> SEQUENCE: 317
cgtggctctc ttatcctcat gat                                           23

<210> SEQ ID NO 318
<211> LENGTH: 21
<212> TYPE: DNA
<213> ORGANISM: Artificial Sequence
<220> FEATURE:
<223> OTHER INFORMATION: TBP.1
      Probe

<400> SEQUENCE: 318
taccgcagca aaccgcttgg g                                             21

<210> SEQ ID NO 319
<211> LENGTH: 20
<212> TYPE: DNA
<213> ORGANISM: Artificial Sequence
<220> FEATURE:
<223> OTHER INFORMATION: TFRC.3
      Forward Primer

<400> SEQUENCE: 319
gccaactgct ttcatttgtg                                               20

<210> SEQ ID NO 320
<211> LENGTH: 20
<212> TYPE: DNA
<213> ORGANISM: Artificial Sequence
<220> FEATURE:
<223> OTHER INFORMATION: TFRC.3
      Reverse Primer

<400> SEQUENCE: 320
actcaggccc atttccttta                                               20

<210> SEQ ID NO 321
<211> LENGTH: 28
<212> TYPE: DNA
<213> ORGANISM: Artificial Sequence
<220> FEATURE:
<223> OTHER INFORMATION: TFRC.3
      Probe

<400> SEQUENCE: 321
agggatctga accaatacag agcagaca                                      28

<210> SEQ ID NO 322
<211> LENGTH: 19
<212> TYPE: DNA
<213> ORGANISM: Artificial Sequence
<220> FEATURE:
<223> OTHER INFORMATION: TST.1
      Forward Primer

<400> SEQUENCE: 322
ggagccggat gcagtagga                                                19

<210> SEQ ID NO 323
<211> LENGTH: 22
<212> TYPE: DNA
<213> ORGANISM: Artificial Sequence
<220> FEATURE:
<223> OTHER INFORMATION: TST.1
      Reverse Primer

<400> SEQUENCE: 323
aagtccatga aaggcatgtt ga                                              22

<210> SEQ ID NO 324
<211> LENGTH: 23
<212> TYPE: DNA
<213> ORGANISM: Artificial Sequence
<220> FEATURE:
<223> OTHER INFORMATION: TST.1
      Probe

<400> SEQUENCE: 324
accacggata tggcccgagt cca                                             23

<210> SEQ ID NO 325
<211> LENGTH: 21
<212> TYPE: DNA
<213> ORGANISM: Artificial Sequence
<220> FEATURE:
<223> OTHER INFORMATION: UGT1A3.1
      Forward Primer

<400> SEQUENCE: 325
gatgcccttg tttggtgatc a                                               21

<210> SEQ ID NO 326
<211> LENGTH: 21
<212> TYPE: DNA
<213> ORGANISM: Artificial Sequence
<220> FEATURE:
<223> OTHER INFORMATION: UGT1A3.1
      Reverse Primer

<400> SEQUENCE: 326
agggtcactc cagctccctt a                                               21

<210> SEQ ID NO 327
<211> LENGTH: 24
<212> TYPE: DNA
<213> ORGANISM: Artificial Sequence
<220> FEATURE:
<223> OTHER INFORMATION: UGT1A3.1
      Probe

<400> SEQUENCE: 327
tctccatgcg ctttgcattg tcca                                            24

<210> SEQ ID NO 328
<211> LENGTH: 19
<212> TYPE: DNA
<213> ORGANISM: Artificial Sequence
<220> FEATURE:
<223> OTHER INFORMATION: UGT2B7.2
      Forward Primer

<400> SEQUENCE: 328
caatggcatc tacgaggca                                                  19

<210> SEQ ID NO 329
<211> LENGTH: 18
<212> TYPE: DNA
<213> ORGANISM: Artificial Sequence
<220> FEATURE:
<223> OTHER INFORMATION: UGT2B7.2
      Reverse Primer

<400> SEQUENCE: 329
caggttgatc ggcaaaca                                              18

<210> SEQ ID NO 330
<211> LENGTH: 24
<212> TYPE: DNA
<213> ORGANISM: Artificial Sequence
<220> FEATURE:
<223> OTHER INFORMATION: UGT2B7.2
      Probe

<400> SEQUENCE: 330
aatccccacc atagggatcc catg                                       24

<210> SEQ ID NO 331
<211> LENGTH: 19
<212> TYPE: DNA
<213> ORGANISM: Artificial Sequence
<220> FEATURE:
<223> OTHER INFORMATION: upa.3
      Forward Primer

<400> SEQUENCE: 331
gtggatgtgc cctgaagga                                             19

<210> SEQ ID NO 332
<211> LENGTH: 20
<212> TYPE: DNA
<213> ORGANISM: Artificial Sequence
<220> FEATURE:
<223> OTHER INFORMATION: upa.3
      Reverse Primer

<400> SEQUENCE: 332
ctgcggatcc agggtaagaa                                            20

<210> SEQ ID NO 333
<211> LENGTH: 28
<212> TYPE: DNA
<213> ORGANISM: Artificial Sequence
<220> FEATURE:
<223> OTHER INFORMATION: upa.3
      Probe

<400> SEQUENCE: 333
aagccaggcg tctacacgag agtctcac                                   28

<210> SEQ ID NO 334
<211> LENGTH: 19
<212> TYPE: DNA
<213> ORGANISM: Artificial Sequence
<220> FEATURE:
<223> OTHER INFORMATION: VDAC1.1
      Forward Primer

<400> SEQUENCE: 334
gctgcgacat ggatttcga                                             19

```
<210> SEQ ID NO 335
<211> LENGTH: 20
<212> TYPE: DNA
<213> ORGANISM: Artificial Sequence
<220> FEATURE:
<223> OTHER INFORMATION: VDAC1.1
      Reverse Primer

<400> SEQUENCE: 335
ccagccctcg taacctagca                                                   20

<210> SEQ ID NO 336
<211> LENGTH: 20
<212> TYPE: DNA
<213> ORGANISM: Artificial Sequence
<220> FEATURE:
<223> OTHER INFORMATION: VDAC1.1
      Probe

<400> SEQUENCE: 336
ttgctgggcc ttccatccgg                                                   20

<210> SEQ ID NO 337
<211> LENGTH: 18
<212> TYPE: DNA
<213> ORGANISM: Artificial Sequence
<220> FEATURE:
<223> OTHER INFORMATION: VDAC2.1
      Forward Primer

<400> SEQUENCE: 337
acccacggac agacttgc                                                     18

<210> SEQ ID NO 338
<211> LENGTH: 18
<212> TYPE: DNA
<213> ORGANISM: Artificial Sequence
<220> FEATURE:
<223> OTHER INFORMATION: VDAC2.1
      Reverse Primer

<400> SEQUENCE: 338
agctttgcca aggtcagc                                                     18

<210> SEQ ID NO 339
<211> LENGTH: 24
<212> TYPE: DNA
<213> ORGANISM: Artificial Sequence
<220> FEATURE:
<223> OTHER INFORMATION: VDAC2.1
      Probe

<400> SEQUENCE: 339
cgcgtccaat gtgtattcct ccat                                              24

<210> SEQ ID NO 340
<211> LENGTH: 20
<212> TYPE: DNA
<213> ORGANISM: Artificial Sequence
<220> FEATURE:
<223> OTHER INFORMATION: XPC.1
      Forward Primer

<400> SEQUENCE: 340
gatacatcgt ctgcgaggaa                                                   20

<210> SEQ ID NO 341
```

-continued

```
<211> LENGTH: 20
<212> TYPE: DNA
<213> ORGANISM: Artificial Sequence
<220> FEATURE:
<223> OTHER INFORMATION: XPC.1
     Reverse Primer

<400> SEQUENCE: 341
ctttcaatga ctgcctgctc                                               20

<210> SEQ ID NO 342
<211> LENGTH: 24
<212> TYPE: DNA
<213> ORGANISM: Artificial Sequence
<220> FEATURE:
<223> OTHER INFORMATION: XPC.1
     Probe

<400> SEQUENCE: 342
ttcaaagacg tgctcctgac tgcc                                          24

<210> SEQ ID NO 343
<211> LENGTH: 77
<212> TYPE: DNA
<213> ORGANISM: Artificial Sequence
<220> FEATURE:
<223> OTHER INFORMATION: Amplicon Sequence

<400> SEQUENCE: 343
agatgagagc agcctgaact tacactgtga aaatgccctg gagaaatgca gagatgcagg    60
tttaatgaag tccatca                                                  77

<210> SEQ ID NO 344
<211> LENGTH: 67
<212> TYPE: DNA
<213> ORGANISM: Artificial Sequence
<220> FEATURE:
<223> OTHER INFORMATION: Amplicon Sequence

<400> SEQUENCE: 344
tgccagctca ttgctcttat agcctgtgag ggaggaagaa acatttgcta accaggccag    60
tgacaga                                                             67

<210> SEQ ID NO 345
<211> LENGTH: 75
<212> TYPE: DNA
<213> ORGANISM: Artificial Sequence
<220> FEATURE:
<223> OTHER INFORMATION: Amplicon Sequence

<400> SEQUENCE: 345
gctttgcctg atgtctacca gaagccctgt gtgtggatgg tgacgcagag gacgtctcta    60
tgccggtgac tggac                                                    75

<210> SEQ ID NO 346
<211> LENGTH: 65
<212> TYPE: DNA
<213> ORGANISM: Artificial Sequence
<220> FEATURE:
<223> OTHER INFORMATION: Amplicon Sequence

<400> SEQUENCE: 346
gatgctgcca ctcaacaact tttgagtcgt ggcgtgcgtc taactgagtt gctgaagcaa    60
ggaca                                                               65
```

<210> SEQ ID NO 347
<211> LENGTH: 66
<212> TYPE: DNA
<213> ORGANISM: Artificial Sequence
<220> FEATURE:
<223> OTHER INFORMATION: Amplicon Sequence

<400> SEQUENCE: 347
cagcagatgt ggatcagcaa gcaggagtat gacgagtccg gcccctccat cgtccaccgc     60
aaatgc                                                               66

<210> SEQ ID NO 348
<211> LENGTH: 70
<212> TYPE: DNA
<213> ORGANISM: Artificial Sequence
<220> FEATURE:
<223> OTHER INFORMATION: Amplicon Sequence

<400> SEQUENCE: 348
ctgggatgcc tttgtggaac tgtacggccc cagcatgcgg cctctgtttg atttctcctg     60
gctgtctctg                                                           70

<210> SEQ ID NO 349
<211> LENGTH: 73
<212> TYPE: DNA
<213> ORGANISM: Artificial Sequence
<220> FEATURE:
<223> OTHER INFORMATION: Amplicon Sequence

<400> SEQUENCE: 349
cagatggacc tagtacccac tgagatttcc acgccgaagg acagcgatgg gaaaaatgcc     60
cttaaatcat agg                                                       73

<210> SEQ ID NO 350
<211> LENGTH: 80
<212> TYPE: DNA
<213> ORGANISM: Artificial Sequence
<220> FEATURE:
<223> OTHER INFORMATION: Amplicon Sequence

<400> SEQUENCE: 350
gcatcatttg ttgggtatgg agttgcagaa gttgggttga gggacactgg cttctagaat     60
caaatattgg cctccataga                                                80

<210> SEQ ID NO 351
<211> LENGTH: 63
<212> TYPE: DNA
<213> ORGANISM: Artificial Sequence
<220> FEATURE:
<223> OTHER INFORMATION: Amplicon Sequence

<400> SEQUENCE: 351
gggcagtggc ctgatgaaaa gcaaaaatga agaaaagaat aaggaaagac acagttttgc     60
cat                                                                  63

<210> SEQ ID NO 352
<211> LENGTH: 79
<212> TYPE: DNA
<213> ORGANISM: Artificial Sequence
<220> FEATURE:
<223> OTHER INFORMATION: Amplicon Sequence

<400> SEQUENCE: 352
gtcactttta tctcacagca tcacaaggag gaacatctga cagcacttgc caggttatca    60
agacaccaag atccaatgc                                                 79

<210> SEQ ID NO 353
<211> LENGTH: 65
<212> TYPE: DNA
<213> ORGANISM: Artificial Sequence
<220> FEATURE:
<223> OTHER INFORMATION: Amplicon Sequence

<400> SEQUENCE: 353
ggagaagtag ccagcccatt taaaatgtca gcaaagattc cagttgtcta aacgcgccag    60
ggaca                                                                65

<210> SEQ ID NO 354
<211> LENGTH: 71
<212> TYPE: DNA
<213> ORGANISM: Artificial Sequence
<220> FEATURE:
<223> OTHER INFORMATION: Amplicon Sequence

<400> SEQUENCE: 354
ctagccaccc ccaagagaaa ccccctgaca gctcccttc cccaggagaa ccttgacctt    60
agaggttggc a                                                         71

<210> SEQ ID NO 355
<211> LENGTH: 67
<212> TYPE: DNA
<213> ORGANISM: Artificial Sequence
<220> FEATURE:
<223> OTHER INFORMATION: Amplicon Sequence

<400> SEQUENCE: 355
tgggtaggtg cacttggtga tgtgagtctg ggctgaggcc acaggtccga gatgcggggg    60
ttggagt                                                              67

<210> SEQ ID NO 356
<211> LENGTH: 78
<212> TYPE: DNA
<213> ORGANISM: Artificial Sequence
<220> FEATURE:
<223> OTHER INFORMATION: Amplicon Sequence

<400> SEQUENCE: 356
atccattcga tctcaccaag gtttggcctc acaaggacta ccctctcatc ccagttggta    60
aactggtctt aaaccgga                                                  78

<210> SEQ ID NO 357
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 357
tggttcccag ccctgtgtcc acctccaagc ccagattcag attcgagtca tgtacacaac    60
ccagggtgga ggag                                                      74

<210> SEQ ID NO 358
<211> LENGTH: 81

<212> TYPE: DNA
<213> ORGANISM: Artificial Sequence
<220> FEATURE:
<223> OTHER INFORMATION: Amplicon Sequence

<400> SEQUENCE: 358
tgagtgtccc ccggtatctt ccccgccctg ccaatcccga tgaaattgga aattttattg    60
atgaaaatct gaaagcggct g                                              81

<210> SEQ ID NO 359
<211> LENGTH: 77
<212> TYPE: DNA
<213> ORGANISM: Artificial Sequence
<220> FEATURE:
<223> OTHER INFORMATION: Amplicon Sequence

<400> SEQUENCE: 359
tgacaatcag cacacctgca ttcaccgctc ggaagagggc ctgagctgca tgaataagga    60
tcacggctgt agtcaca                                                   77

<210> SEQ ID NO 360
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 360
gctgcatttt atgtccaaat ggaaccttcc aaaatgagga aggacaaatg acttgtgaac    60
catgcccaag acca                                                      74

<210> SEQ ID NO 361
<211> LENGTH: 51
<212> TYPE: DNA
<213> ORGANISM: Artificial Sequence
<220> FEATURE:
<223> OTHER INFORMATION: Amplicon Sequence

<400> SEQUENCE: 361
tccccttgcc tttggagaac agcccaaatc ctttgatgcc tccaggcctt t             51

<210> SEQ ID NO 362
<211> LENGTH: 86
<212> TYPE: DNA
<213> ORGANISM: Artificial Sequence
<220> FEATURE:
<223> OTHER INFORMATION: Amplicon Sequence

<400> SEQUENCE: 362
cttaatggtg tttagcacag atgcaggctg tttcctgtgc atttgccccc ccagcaggcc    60
ctgtgctgct tcgcatgcta cagtgg                                         86

<210> SEQ ID NO 363
<211> LENGTH: 67
<212> TYPE: DNA
<213> ORGANISM: Artificial Sequence
<220> FEATURE:
<223> OTHER INFORMATION: Amplicon Sequence

<400> SEQUENCE: 363
ccttatcggc tggaacgagt tcatcctgca gcccatccac aacctgctca tgggtgacac    60
caaggag                                                              67

<210> SEQ ID NO 364
<211> LENGTH: 67
<212> TYPE: DNA
<213> ORGANISM: Artificial Sequence
<220> FEATURE:
<223> OTHER INFORMATION: Amplicon Sequence

<400> SEQUENCE: 364
cgttctgtcc ctcacactgt gacctgacca gccccaccgg cccatcctgg tcatgttact    60
gcatttg                                                              67

<210> SEQ ID NO 365
<211> LENGTH: 78
<212> TYPE: DNA
<213> ORGANISM: Artificial Sequence
<220> FEATURE:
<223> OTHER INFORMATION: Amplicon Sequence

<400> SEQUENCE: 365
aagtcctgaa attgcgatca gatattgcag taccgattcc aaaagaccat caggttctaa    60
tcaaggtcca tgcatgtg                                                  78

<210> SEQ ID NO 366
<211> LENGTH: 67
<212> TYPE: DNA
<213> ORGANISM: Artificial Sequence
<220> FEATURE:
<223> OTHER INFORMATION: Amplicon Sequence

<400> SEQUENCE: 366
tgtctcactg agcgagcaga atctggtgga ctgttcgcgt cctcaaggca atcagggctg    60
caatggt                                                              67

<210> SEQ ID NO 367
<211> LENGTH: 78
<212> TYPE: DNA
<213> ORGANISM: Artificial Sequence
<220> FEATURE:
<223> OTHER INFORMATION: Amplicon Sequence

<400> SEQUENCE: 367
tcagaggctt gtttgctgag ggtgcctgcg cagctgcgac ggctgctggt tttgaaacat    60
gaatctttcg ctcgtcct                                                  78

<210> SEQ ID NO 368
<211> LENGTH: 84
<212> TYPE: DNA
<213> ORGANISM: Artificial Sequence
<220> FEATURE:
<223> OTHER INFORMATION: Amplicon Sequence

<400> SEQUENCE: 368
tggacttcta gtgatgagaa agattgagaa tgttcccaca ggccccaaca ataagcccaa    60
gctacctgtg gtgatctcgc agtg                                           84

<210> SEQ ID NO 369
<211> LENGTH: 76
<212> TYPE: DNA
<213> ORGANISM: Artificial Sequence
<220> FEATURE:
<223> OTHER INFORMATION: Amplicon Sequence

<400> SEQUENCE: 369

```
ccggagtgac tctatcacca acatgctgga cacactgatg caagccaaga tgaactcaga    60
taatggcaat gctggc                                                    76

<210> SEQ ID NO 370
<211> LENGTH: 70
<212> TYPE: DNA
<213> ORGANISM: Artificial Sequence
<220> FEATURE:
<223> OTHER INFORMATION: Amplicon Sequence

<400> SEQUENCE: 370
tccttatagg tactttcagc catttggctt tgggccccgt ggctgtgcag gaaagtacat    60
cgccatggtg                                                          70

<210> SEQ ID NO 371
<211> LENGTH: 73
<212> TYPE: DNA
<213> ORGANISM: Artificial Sequence
<220> FEATURE:
<223> OTHER INFORMATION: Amplicon Sequence

<400> SEQUENCE: 371
aataatttcg gggaggtggt tggctctgga aacccagctg acttcatccc tattcttcgc    60
tacctaccca acc                                                      73

<210> SEQ ID NO 372
<211> LENGTH: 71
<212> TYPE: DNA
<213> ORGANISM: Artificial Sequence
<220> FEATURE:
<223> OTHER INFORMATION: Amplicon Sequence

<400> SEQUENCE: 372
ccagctttgt gcctgtcact attcctcatg ccaccactgc caacacctct gtcttgggct    60
accacattcc c                                                        71

<210> SEQ ID NO 373
<211> LENGTH: 76
<212> TYPE: DNA
<213> ORGANISM: Artificial Sequence
<220> FEATURE:
<223> OTHER INFORMATION: Amplicon Sequence

<400> SEQUENCE: 373
gccttacacc acgatgtgca tcaaggaatg cctccgcctc tacgcaccgg tagtaaacat    60
atcccggtta ctcgac                                                   76

<210> SEQ ID NO 374
<211> LENGTH: 76
<212> TYPE: DNA
<213> ORGANISM: Artificial Sequence
<220> FEATURE:
<223> OTHER INFORMATION: Amplicon Sequence

<400> SEQUENCE: 374
accgtaggct ctgctctgaa tgactctcct gtgggtctgg ctgcctatat tctagagaag    60
ttttccacct ggacca                                                   76

<210> SEQ ID NO 375
<211> LENGTH: 68
<212> TYPE: DNA
```

```
<213> ORGANISM: Artificial Sequence
<220> FEATURE:
<223> OTHER INFORMATION: Amplicon Sequence

<400> SEQUENCE: 375
cgtggtgccc ctctatgacc tgctgctgga gatgctggac gcccaccgcc tacatgcgcc      60
cactagcc                                                               68

<210> SEQ ID NO 376
<211> LENGTH: 82
<212> TYPE: DNA
<213> ORGANISM: Artificial Sequence
<220> FEATURE:
<223> OTHER INFORMATION: Amplicon Sequence

<400> SEQUENCE: 376
ccaccccgag caaatctgtc ctccccagaa ccctgaatc ctggaggctc acgccccag         60 ccaaagtagg gggactggat tt                                               82

<210> SEQ ID NO 377
<211> LENGTH: 69
<212> TYPE: DNA
<213> ORGANISM: Artificial Sequence
<220> FEATURE:
<223> OTHER INFORMATION: Amplicon Sequence

<400> SEQUENCE: 377
tgcccagatg tgcgctatta gatgtttctc tgataatgtc cccaatcata ccagggagac      60
tggcattga                                                              69

<210> SEQ ID NO 378
<211> LENGTH: 64
<212> TYPE: DNA
<213> ORGANISM: Artificial Sequence
<220> FEATURE:
<223> OTHER INFORMATION: Amplicon Sequence

<400> SEQUENCE: 378
tggacagaga caagatgtga tgtggggaag ggtccctatg gccatgtttt gtctaggtgc      60
cagc                                                                   64

<210> SEQ ID NO 379
<211> LENGTH: 64
<212> TYPE: DNA
<213> ORGANISM: Artificial Sequence
<220> FEATURE:
<223> OTHER INFORMATION: Amplicon Sequence

<400> SEQUENCE: 379
ggtgtcctat tttcctctga agagagattc tggccaatta agaatgttgg accttcagct      60
tgca                                                                   64

<210> SEQ ID NO 380
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 380
attccaccca tggcaaattc catggcaccg tcaaggctga gaacgggaag cttgtcatca      60
atggaaatcc catc                                                        74
```

<210> SEQ ID NO 381
<211> LENGTH: 71
<212> TYPE: DNA
<213> ORGANISM: Artificial Sequence
<220> FEATURE:
<223> OTHER INFORMATION: Amplicon Sequence

<400> SEQUENCE: 381
ctgttgcagg aaggcattga tcatctcctg gcccagcatg ttgctcatct ctttattaga    60
gacccactga c                                                         71

<210> SEQ ID NO 382
<211> LENGTH: 85
<212> TYPE: DNA
<213> ORGANISM: Artificial Sequence
<220> FEATURE:
<223> OTHER INFORMATION: Amplicon Sequence

<400> SEQUENCE: 382
tgtagaatca aactcttcat catcaactag aagtgcagtt gacatggcct gttcagtcct    60
tggagttgca cagctggatt ctgtg                                          85

<210> SEQ ID NO 383
<211> LENGTH: 67
<212> TYPE: DNA
<213> ORGANISM: Artificial Sequence
<220> FEATURE:
<223> OTHER INFORMATION: Amplicon Sequence

<400> SEQUENCE: 383
gcttatgacc gaccccaagc tcatcacctg gtctccggtg tgtcgcaacg atgttgcctg    60
gaacttt                                                              67

<210> SEQ ID NO 384
<211> LENGTH: 75
<212> TYPE: DNA
<213> ORGANISM: Artificial Sequence
<220> FEATURE:
<223> OTHER INFORMATION: Amplicon Sequence

<400> SEQUENCE: 384
cacacagatc tcctactcca tccagtcctg aggagcctta ggatgcagca tgccttcagg    60
agacactgct ggacc                                                     75

<210> SEQ ID NO 385
<211> LENGTH: 86
<212> TYPE: DNA
<213> ORGANISM: Artificial Sequence
<220> FEATURE:
<223> OTHER INFORMATION: Amplicon Sequence

<400> SEQUENCE: 385
aagctatgag gaaagaagt acacgatggg ggacgctcct gattatgaca gaagccagtg     60
gctgaatgaa aaattcaagc tgggcc                                         86

<210> SEQ ID NO 386
<211> LENGTH: 82
<212> TYPE: DNA
<213> ORGANISM: Artificial Sequence
<220> FEATURE:
<223> OTHER INFORMATION: Amplicon Sequence

```
<400> SEQUENCE: 386
ccatggtttg caggaaacaa gggcttggag aagatctctg cctacatgaa gtccagccgc    60
ttcctcccaa gacctgtgtt ct                                             82

<210> SEQ ID NO 387
<211> LENGTH: 79
<212> TYPE: DNA
<213> ORGANISM: Artificial Sequence
<220> FEATURE:
<223> OTHER INFORMATION: Amplicon Sequence

<400> SEQUENCE: 387
aacgggtacg tgcagtgtaa actgggggct tccctggtgc agacaaagtc agggaccctc    60
catctctgac gcgacctgc                                                 79

<210> SEQ ID NO 388
<211> LENGTH: 61
<212> TYPE: DNA
<213> ORGANISM: Artificial Sequence
<220> FEATURE:
<223> OTHER INFORMATION: Amplicon Sequence

<400> SEQUENCE: 388
tctgtgtcca cctgcattcg ttcatgtgac agtattctta tttcagtcct gccatgagca    60
g                                                                    61

<210> SEQ ID NO 389
<211> LENGTH: 75
<212> TYPE: DNA
<213> ORGANISM: Artificial Sequence
<220> FEATURE:
<223> OTHER INFORMATION: Amplicon Sequence

<400> SEQUENCE: 389
cgactccaat gtcatgtcaa caaaagcaga ggcaattccc accaaccttc ggacacgatc    60
caggcatccc agggt                                                     75

<210> SEQ ID NO 390
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 390
ggcaattccc accaaccttc ggacacgatc caggcatccc agggtagaaa ttcagttcct    60
gtatggtaaa gttt                                                      74

<210> SEQ ID NO 391
<211> LENGTH: 61
<212> TYPE: DNA
<213> ORGANISM: Artificial Sequence
<220> FEATURE:
<223> OTHER INFORMATION: Amplicon Sequence

<400> SEQUENCE: 391
atggcaccct cgaattgcat cttctcctca acagttttct gagtgctgtc attgacatgc    60
a                                                                    61

<210> SEQ ID NO 392
<211> LENGTH: 59
```

```
<212> TYPE: DNA
<213> ORGANISM: Artificial Sequence
<220> FEATURE:
<223> OTHER INFORMATION: Amplicon Sequence

<400> SEQUENCE: 392
gcctccctgt ggaaaaggag actgtttgtg cagtcaagga gtgacagggc ctggtgtga        59

<210> SEQ ID NO 393
<211> LENGTH: 82
<212> TYPE: DNA
<213> ORGANISM: Artificial Sequence
<220> FEATURE:
<223> OTHER INFORMATION: Amplicon Sequence

<400> SEQUENCE: 393
gcaggaacga gaggaggaga tggggctccc cttgtgcaga gtcgtcacaa agtcagggac        60
cctccatctc tgacccgagc tg                                                82

<210> SEQ ID NO 394
<211> LENGTH: 71
<212> TYPE: DNA
<213> ORGANISM: Artificial Sequence
<220> FEATURE:
<223> OTHER INFORMATION: Amplicon Sequence

<400> SEQUENCE: 394
ctgggctgtg aggctgagag tgaatctgct ttacgagggt aggcggggaa tcagaaaagg        60
agcagattcg c                                                            71

<210> SEQ ID NO 395
<211> LENGTH: 76
<212> TYPE: DNA
<213> ORGANISM: Artificial Sequence
<220> FEATURE:
<223> OTHER INFORMATION: Amplicon Sequence

<400> SEQUENCE: 395
caatgccatc ttgcgctaca tcgctcgcaa gcacaacatg tgtggtgaga ctgaagaaga        60
aaagattcga gtggac                                                       76

<210> SEQ ID NO 396
<211> LENGTH: 76
<212> TYPE: DNA
<213> ORGANISM: Artificial Sequence
<220> FEATURE:
<223> OTHER INFORMATION: Amplicon Sequence

<400> SEQUENCE: 396
ccagaagcca aggatctctc tagtgatggt cagagggccc aaatggcagg gatacccagt        60
gatgtcagga ggaata                                                       76

<210> SEQ ID NO 397
<211> LENGTH: 86
<212> TYPE: DNA
<213> ORGANISM: Artificial Sequence
<220> FEATURE:
<223> OTHER INFORMATION: Amplicon Sequence

<400> SEQUENCE: 397
tcacagtttc cctagtcctc gaaggctcgg aagcccgtca ccatgtcgtg cgagtcgtct        60
atggttctcg ggtactggga tattcg                                            86
```

<210> SEQ ID NO 398
<211> LENGTH: 80
<212> TYPE: DNA
<213> ORGANISM: Artificial Sequence
<220> FEATURE:
<223> OTHER INFORMATION: Amplicon Sequence

<400> SEQUENCE: 398
cggaccttgc tccctgaaca ctcggaggtg gcggtggatc ttactccttc cagccagtga    60
ggatccagca acctgctccg                                                80

<210> SEQ ID NO 399
<211> LENGTH: 72
<212> TYPE: DNA
<213> ORGANISM: Artificial Sequence
<220> FEATURE:
<223> OTHER INFORMATION: Amplicon Sequence

<400> SEQUENCE: 399
tccctgaggc tcccttgact caggactgtg ctcgaattgt gggtggtttt ttgtcttctg    60
ttgtccacag cc                                                        72

<210> SEQ ID NO 400
<211> LENGTH: 83
<212> TYPE: DNA
<213> ORGANISM: Artificial Sequence
<220> FEATURE:
<223> OTHER INFORMATION: Amplicon Sequence

<400> SEQUENCE: 400
gaaaggtgct ctgtgccaag ttcctcactc attcgcgctc ctgtaggccg tctagaactg    60
gcatggttca agagggggct agg                                            83

<210> SEQ ID NO 401
<211> LENGTH: 76
<212> TYPE: DNA
<213> ORGANISM: Artificial Sequence
<220> FEATURE:
<223> OTHER INFORMATION: Amplicon Sequence

<400> SEQUENCE: 401
gagaccctgc tgtcccagaa ccagggaggc aagaccttca ttgtgggaga ccagatctcc    60
ttcgctgact acaacc                                                    76

<210> SEQ ID NO 402
<211> LENGTH: 66
<212> TYPE: DNA
<213> ORGANISM: Artificial Sequence
<220> FEATURE:
<223> OTHER INFORMATION: Amplicon Sequence

<400> SEQUENCE: 402
caccatcccc accctgtctt ccacagccgc ctgaaagcca caatgagaat gatgcacact    60
gaggcc                                                               66

<210> SEQ ID NO 403
<211> LENGTH: 73
<212> TYPE: DNA
<213> ORGANISM: Artificial Sequence
<220> FEATURE:
<223> OTHER INFORMATION: Amplicon Sequence

<400> SEQUENCE: 403

```
cccactcagt agccaagtca caatgtttgg aaaacagccc gtttacttga gcaagactga      60
taccacctgc gtg                                                        73

<210> SEQ ID NO 404
<211> LENGTH: 71
<212> TYPE: DNA
<213> ORGANISM: Artificial Sequence
<220> FEATURE:
<223> OTHER INFORMATION: Amplicon Sequence

<400> SEQUENCE: 404
cgtgccttat ggttactttg gaggcgggta ctactcctgc cgagtgtccc ggagctcgct      60
gaaaccctgt g                                                          71

<210> SEQ ID NO 405
<211> LENGTH: 78
<212> TYPE: DNA
<213> ORGANISM: Artificial Sequence
<220> FEATURE:
<223> OTHER INFORMATION: Amplicon Sequence

<400> SEQUENCE: 405
ctggaccgca cggacatcca caccttccac cgcttctacc aatacctcgc ccacagcaag      60
caagtctttc gcgaggcg                                                   78

<210> SEQ ID NO 406
<211> LENGTH: 68
<212> TYPE: DNA
<213> ORGANISM: Artificial Sequence
<220> FEATURE:
<223> OTHER INFORMATION: Amplicon Sequence

<400> SEQUENCE: 406
gctttccaag tggggaatta aagttgcttc catccaacct ggaggcttcc taacaaatat      60
cgcaggca                                                              68

<210> SEQ ID NO 407
<211> LENGTH: 72
<212> TYPE: DNA
<213> ORGANISM: Artificial Sequence
<220> FEATURE:
<223> OTHER INFORMATION: Amplicon Sequence

<400> SEQUENCE: 407
ttgtcctttg gctttgtcac gagagttgtg aggagaatgg tggcttgttt gaggttggag      60
caggatggat tg                                                         72

<210> SEQ ID NO 408
<211> LENGTH: 76
<212> TYPE: DNA
<213> ORGANISM: Artificial Sequence
<220> FEATURE:
<223> OTHER INFORMATION: Amplicon Sequence

<400> SEQUENCE: 408
accctctggt ggtaaatgga catttcccta catcggcttc cctgtagagc tgaacacagt      60
ctatttcatt ggggcc                                                     76

<210> SEQ ID NO 409
<211> LENGTH: 76
<212> TYPE: DNA
```

```
<213> ORGANISM: Artificial Sequence
<220> FEATURE:
<223> OTHER INFORMATION: Amplicon Sequence

<400> SEQUENCE: 409
ctgcctatgc cagactcaga ggaatcgaac aggctgttca gagccatgca gttgctgaag    60
aggaagccag aaaagc                                                    76

<210> SEQ ID NO 410
<211> LENGTH: 80
<212> TYPE: DNA
<213> ORGANISM: Artificial Sequence
<220> FEATURE:
<223> OTHER INFORMATION: Amplicon Sequence

<400> SEQUENCE: 410
cggactttgg gtgcgacttg acgagcggtg gttcgacaag tggccttgcg ggccggatcg    60
tcccagtgga agagttgtaa                                                80

<210> SEQ ID NO 411
<211> LENGTH: 68
<212> TYPE: DNA
<213> ORGANISM: Artificial Sequence
<220> FEATURE:
<223> OTHER INFORMATION: Amplicon Sequence

<400> SEQUENCE: 411
ccagttgtct tcctgcaaca tggcttgctg gcagattcta gtaactgggt cacaaacctt    60
gccaacag                                                             68

<210> SEQ ID NO 412
<211> LENGTH: 63
<212> TYPE: DNA
<213> ORGANISM: Artificial Sequence
<220> FEATURE:
<223> OTHER INFORMATION: Amplicon Sequence

<400> SEQUENCE: 412
ccaacacctt tgttgcagag ctgaagggtt tggatccagc tcgagtcaac gtccctgtca    60
ttg                                                                  63

<210> SEQ ID NO 413
<211> LENGTH: 79
<212> TYPE: DNA
<213> ORGANISM: Artificial Sequence
<220> FEATURE:
<223> OTHER INFORMATION: Amplicon Sequence

<400> SEQUENCE: 413
acggatctac cacaccattg catatttgac accccttccc cagccaaata gagctttgag    60
tttttttgtt ggatatgga                                                 79

<210> SEQ ID NO 414
<211> LENGTH: 67
<212> TYPE: DNA
<213> ORGANISM: Artificial Sequence
<220> FEATURE:
<223> OTHER INFORMATION: Amplicon Sequence

<400> SEQUENCE: 414
agctgttgga ggtgtttacc acccgcgtat agcttctggc ctgggcttgg cctggattgt    60
tggacga                                                              67
```

<210> SEQ ID NO 415
<211> LENGTH: 72
<212> TYPE: DNA
<213> ORGANISM: Artificial Sequence
<220> FEATURE:
<223> OTHER INFORMATION: Amplicon Sequence

<400> SEQUENCE: 415
ccatacgtgc tgctacctgt agatattggt gatgaaccat ggtttgatga ttctgccatt    60
caaaccttta gg                                                        72

<210> SEQ ID NO 416
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 416
ccaatgtgtt gctgttatct ggaactccta cctgtcctgg aaggcacatc ggctctaagc    60
ctgcctcact ccat                                                      74

<210> SEQ ID NO 417
<211> LENGTH: 75
<212> TYPE: DNA
<213> ORGANISM: Artificial Sequence
<220> FEATURE:
<223> OTHER INFORMATION: Amplicon Sequence

<400> SEQUENCE: 417
acgagaacga gggcatctat gtgcaggatg tcaagaccgg aaaggtgcgc gctgtgattg    60
gaagcaccta catgc                                                     75

<210> SEQ ID NO 418
<211> LENGTH: 75
<212> TYPE: DNA
<213> ORGANISM: Artificial Sequence
<220> FEATURE:
<223> OTHER INFORMATION: Amplicon Sequence

<400> SEQUENCE: 418
tggttttgag accacgatgt tgggagggta tgtttacagc actccagcca aaaaatacag    60
cactggcatg attca                                                     75

<210> SEQ ID NO 419
<211> LENGTH: 73
<212> TYPE: DNA
<213> ORGANISM: Artificial Sequence
<220> FEATURE:
<223> OTHER INFORMATION: Amplicon Sequence

<400> SEQUENCE: 419
taactgacat tcttgagcac cagatccggg ctgttccctt tgagaacctt aacatgcatt    60
gtgggcaagc cat                                                       73

<210> SEQ ID NO 420
<211> LENGTH: 74
<212> TYPE: DNA
<213> ORGANISM: Artificial Sequence
<220> FEATURE:
<223> OTHER INFORMATION: Amplicon Sequence

```
<400> SEQUENCE: 420
agtgacctcc gtgcctacgt cagggctgtc ctccatgggt cccgagcagg ttaatgatcc    60
tgctctgagg ggag                                                     74

<210> SEQ ID NO 421
<211> LENGTH: 79
<212> TYPE: DNA
<213> ORGANISM: Artificial Sequence
<220> FEATURE:
<223> OTHER INFORMATION: Amplicon Sequence

<400> SEQUENCE: 421
gcagctacgc taccaggaga tctccaagcg aactcagcct cctcccaagc tccctgtggg    60
tcctagccac aagctctcc                                                79

<210> SEQ ID NO 422
<211> LENGTH: 71
<212> TYPE: DNA
<213> ORGANISM: Artificial Sequence
<220> FEATURE:
<223> OTHER INFORMATION: Amplicon Sequence

<400> SEQUENCE: 422
cagcagacgc ccgaattcaa atcctggaag gatggaagaa acgcctggag aatatttggg    60
atgagacacc a                                                        71

<210> SEQ ID NO 423
<211> LENGTH: 64
<212> TYPE: DNA
<213> ORGANISM: Artificial Sequence
<220> FEATURE:
<223> OTHER INFORMATION: Amplicon Sequence

<400> SEQUENCE: 423
agcgctcctt tccgtaacca cgggaggcac ggccgagatg tacacgaaga caggagtcaa    60
tgga                                                                64

<210> SEQ ID NO 424
<211> LENGTH: 68
<212> TYPE: DNA
<213> ORGANISM: Artificial Sequence
<220> FEATURE:
<223> OTHER INFORMATION: Amplicon Sequence

<400> SEQUENCE: 424
ctttgaaccc ttgcttgcaa taggtgtgcg tcagaagcac ccaggacttc catttgcttt    60
gtcccggg                                                            68

<210> SEQ ID NO 425
<211> LENGTH: 81
<212> TYPE: DNA
<213> ORGANISM: Artificial Sequence
<220> FEATURE:
<223> OTHER INFORMATION: Amplicon Sequence

<400> SEQUENCE: 425
ccgcaacgtg gttttctcac cctatggggt ggcctcggtg ttggccatgc tccagctgac    60
aacaggagga gaaacccagc a                                             81

<210> SEQ ID NO 426
<211> LENGTH: 85
```

```
<212> TYPE: DNA
<213> ORGANISM: Artificial Sequence
<220> FEATURE:
<223> OTHER INFORMATION: Amplicon Sequence

<400> SEQUENCE: 426
gcatcaggct gtcattatgg tgtccttacc tgtgggagct gtaaggtctt ctttaagagg    60
gcaatggaag ggcagcacaa ctact                                          85

<210> SEQ ID NO 427
<211> LENGTH: 73
<212> TYPE: DNA
<213> ORGANISM: Artificial Sequence
<220> FEATURE:
<223> OTHER INFORMATION: Amplicon Sequence

<400> SEQUENCE: 427
gttccatccc aaagaacctg ctattgagag tagcattcag ataacgggt ggaaatgcca     60 actccagagt ttc                                                       73

<210> SEQ ID NO 428
<211> LENGTH: 66
<212> TYPE: DNA
<213> ORGANISM: Artificial Sequence
<220> FEATURE:
<223> OTHER INFORMATION: Amplicon Sequence

<400> SEQUENCE: 428
tctccatatc tgccttgcag agtctcctgc agcacctcat cgggctgagc aatctgaccc    60
acgtgc                                                               66

<210> SEQ ID NO 429
<211> LENGTH: 64
<212> TYPE: DNA
<213> ORGANISM: Artificial Sequence
<220> FEATURE:
<223> OTHER INFORMATION: Amplicon Sequence

<400> SEQUENCE: 429
ccactgctcc cagcttacaa ccttaagctt ctacgggaat tccatctcca tatctgcctt    60
gcag                                                                 64

<210> SEQ ID NO 430
<211> LENGTH: 65
<212> TYPE: DNA
<213> ORGANISM: Artificial Sequence
<220> FEATURE:
<223> OTHER INFORMATION: Amplicon Sequence

<400> SEQUENCE: 430
atcaggcaca gagatagagg tgactggggc ccaggcagtg gcagaaggaa gcccgagttg    60
aaaga                                                                65

<210> SEQ ID NO 431
<211> LENGTH: 69
<212> TYPE: DNA
<213> ORGANISM: Artificial Sequence
<220> FEATURE:
<223> OTHER INFORMATION: Amplicon Sequence

<400> SEQUENCE: 431
ggtgtccttc gccagatcac tgttaatgat ttgcctgtgg gacgctccgt ggatgaggct    60
``` ctgcggctg 69

<210> SEQ ID NO 432
<211> LENGTH: 80
<212> TYPE: DNA
<213> ORGANISM: Artificial Sequence
<220> FEATURE:
<223> OTHER INFORMATION: Amplicon Sequence

<400> SEQUENCE: 432
tgaccccaat ggagtcatca agcatttgag cgtcaacgat ctcccagtgg gccgaagcgt    60
ggaagaaacc ctccgcttgg                                                80

<210> SEQ ID NO 433
<211> LENGTH: 75
<212> TYPE: DNA
<213> ORGANISM: Artificial Sequence
<220> FEATURE:
<223> OTHER INFORMATION: Amplicon Sequence

<400> SEQUENCE: 433
ttacccattt ggcctggatt aatacccctc gaagacaagg aggacttggg ccaataagga    60
ttccacttct ttcag                                                     75

<210> SEQ ID NO 434
<211> LENGTH: 76
<212> TYPE: DNA
<213> ORGANISM: Artificial Sequence
<220> FEATURE:
<223> OTHER INFORMATION: Amplicon Sequence

<400> SEQUENCE: 434
ctgtgagcca gaggatgtca gctgccaatt gtgttttcct gcagcaattc cataaacaca    60
tcctggtgtc atcaca                                                    76

<210> SEQ ID NO 435
<211> LENGTH: 75
<212> TYPE: DNA
<213> ORGANISM: Artificial Sequence
<220> FEATURE:
<223> OTHER INFORMATION: Amplicon Sequence

<400> SEQUENCE: 435
ccattctatc atcaacgggt acaaacgagt cctggccttg tctgtggaga cggattacac    60
cttcccactt gctga                                                     75

<210> SEQ ID NO 436
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 436
cgcctacata aacctcacca tatttggaag attcctactc catttgcaag tcatgctttt    60
caccctattg atgg                                                      74

<210> SEQ ID NO 437
<211> LENGTH: 70
<212> TYPE: DNA
<213> ORGANISM: Artificial Sequence
<220> FEATURE:
<223> OTHER INFORMATION: Amplicon Sequence

```
<400> SEQUENCE: 437
tgaagagagg catgttggag acttgggcaa tgtgactgct gacaaagatg gtgtggccga    60
tgtgtctatt                                                          70

<210> SEQ ID NO 438
<211> LENGTH: 78
<212> TYPE: DNA
<213> ORGANISM: Artificial Sequence
<220> FEATURE:
<223> OTHER INFORMATION: Amplicon Sequence

<400> SEQUENCE: 438
gcttgtccaa atcaggatcc actgcaagga acaacaggcc ttattccact gctggggatt    60
gatgtgtggg agcacgct                                                 78

<210> SEQ ID NO 439
<211> LENGTH: 68
<212> TYPE: DNA
<213> ORGANISM: Artificial Sequence
<220> FEATURE:
<223> OTHER INFORMATION: Amplicon Sequence

<400> SEQUENCE: 439
ccataagccc tgagactccc gcctttgacc tgacgatctt ccccttccc gccttcaggt     60 tcctccta                                                            68

<210> SEQ ID NO 440
<211> LENGTH: 81
<212> TYPE: DNA
<213> ORGANISM: Artificial Sequence
<220> FEATURE:
<223> OTHER INFORMATION: Amplicon Sequence

<400> SEQUENCE: 440
gtaggtctcc tggcgttctg ccagctggcc tggggattct gagtggtgtc tgcttagagt    60
ttactcctac ccttccaggg a                                             81

<210> SEQ ID NO 441
<211> LENGTH: 69
<212> TYPE: DNA
<213> ORGANISM: Artificial Sequence
<220> FEATURE:
<223> OTHER INFORMATION: Amplicon Sequence

<400> SEQUENCE: 441
catcttccag gaggaccact ctctgtggca ccctggacta cctgcccct gaaatgattg     60 aaggtcgga                                                           69

<210> SEQ ID NO 442
<211> LENGTH: 61
<212> TYPE: DNA
<213> ORGANISM: Artificial Sequence
<220> FEATURE:
<223> OTHER INFORMATION: Amplicon Sequence

<400> SEQUENCE: 442 gcccctgaa atgattgaag gtcggatgca tgatgagaag gtggatctct ggagccttgg     60
a                                                                   61

<210> SEQ ID NO 443
```

-continued

```
<211> LENGTH: 68
<212> TYPE: DNA
<213> ORGANISM: Artificial Sequence
<220> FEATURE:
<223> OTHER INFORMATION: Amplicon Sequence

<400> SEQUENCE: 443
cattcacatt tataaaccca catggaggtt ggtcttgtcg ggaattcttt ccgcctttac    60
tttggatt                                                             68

<210> SEQ ID NO 444
<211> LENGTH: 79
<212> TYPE: DNA
<213> ORGANISM: Artificial Sequence
<220> FEATURE:
<223> OTHER INFORMATION: Amplicon Sequence

<400> SEQUENCE: 444
gcgaggaatg aacccacaga ctcttttgct tttagcggtc taacagaggc taagagtcta    60
aatccactgg ttctcatgc                                                 79

<210> SEQ ID NO 445
<211> LENGTH: 75
<212> TYPE: DNA
<213> ORGANISM: Artificial Sequence
<220> FEATURE:
<223> OTHER INFORMATION: Amplicon Sequence

<400> SEQUENCE: 445
atggtggctg gtcatccaaa tcctggatcc tttccagagt tgtgtggagaa attcatgcaa    60 ggacaggttc cttat                                                     75

<210> SEQ ID NO 446
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 446
cacctgccct accgctttct gccctctgac ctccacaatg gagactccaa ggtcatctat    60
atggctcgca accc                                                      74

<210> SEQ ID NO 447
<211> LENGTH: 80
<212> TYPE: DNA
<213> ORGANISM: Artificial Sequence
<220> FEATURE:
<223> OTHER INFORMATION: Amplicon Sequence

<400> SEQUENCE: 447
tgttttgatt cccgggctta ccaggtgaga agtgagggag gaagaaggca gtgtcccttt    60
tgctagagct gacagctttg                                                80

<210> SEQ ID NO 448
<211> LENGTH: 65
<212> TYPE: DNA
<213> ORGANISM: Artificial Sequence
<220> FEATURE:
<223> OTHER INFORMATION: Amplicon Sequence

<400> SEQUENCE: 448
gcccgaaacg ccgaatataa tcccaagcgg tttgctgcgg taatcatgag gataagagag    60
``` ccacg                                                              65

<210> SEQ ID NO 449
<211> LENGTH: 68
<212> TYPE: DNA
<213> ORGANISM: Artificial Sequence
<220> FEATURE:
<223> OTHER INFORMATION: Amplicon Sequence

<400> SEQUENCE: 449
gccaactgct tcatttgtg agggatctga accaatacag agcagacata aaggaaatgg    60
gcctgagt                                                           68

<210> SEQ ID NO 450
<211> LENGTH: 69
<212> TYPE: DNA
<213> ORGANISM: Artificial Sequence
<220> FEATURE:
<223> OTHER INFORMATION: Amplicon Sequence

<400> SEQUENCE: 450
ggagccggat gcagtaggac tggactcggg ccatatccgt ggtgccgtca acatgccttt    60
catggactt                                                          69

<210> SEQ ID NO 451
<211> LENGTH: 69
<212> TYPE: DNA
<213> ORGANISM: Artificial Sequence
<220> FEATURE:
<223> OTHER INFORMATION: Amplicon Sequence

<400> SEQUENCE: 451
gatgcccttg tttggtgatc agatggacaa tgcaaagcgc atggagacta agggagctgg    60
agtgaccct                                                          69

<210> SEQ ID NO 452
<211> LENGTH: 71
<212> TYPE: DNA
<213> ORGANISM: Artificial Sequence
<220> FEATURE:
<223> OTHER INFORMATION: Amplicon Sequence

<400> SEQUENCE: 452
caatggcatc tacgaggcaa tctaccatgg gatccctatg gtggggattc cattgtttgc    60
cgatcaacct g                                                       71

<210> SEQ ID NO 453
<211> LENGTH: 70
<212> TYPE: DNA
<213> ORGANISM: Artificial Sequence
<220> FEATURE:
<223> OTHER INFORMATION: Amplicon Sequence

<400> SEQUENCE: 453
gtggatgtgc cctgaaggac aagccaggcg tctacacgag agtctcacac ttcttaccct    60
ggatccgcag                                                         70

<210> SEQ ID NO 454
<211> LENGTH: 71
<212> TYPE: DNA
<213> ORGANISM: Artificial Sequence
<220> FEATURE:

<223> OTHER INFORMATION: Amplicon Sequence

<400> SEQUENCE: 454
gctgcgacat ggatttcgac attgctgggc cttccatccg gggtgctctg gtgctaggtt    60
acgagggctg g                                                        71

<210> SEQ ID NO 455
<211> LENGTH: 66
<212> TYPE: DNA
<213> ORGANISM: Artificial Sequence
<220> FEATURE:
<223> OTHER INFORMATION: Amplicon Sequence

<400> SEQUENCE: 455
acccacggac agacttgcgc gcgtccaatg tgtattcctc catcatatgc tgaccttggc    60
aaagct                                                              66

<210> SEQ ID NO 456
<211> LENGTH: 73
<212> TYPE: DNA
<213> ORGANISM: Artificial Sequence
<220> FEATURE:
<223> OTHER INFORMATION: Amplicon Sequence

<400> SEQUENCE: 456
gatacatcgt ctgcgaggaa ttcaaagacg tgctcctgac tgcctgggaa aatgagcagg    60
cagtcattga aag                                                      73

<210> SEQ ID NO 457
<211> LENGTH: 86
<212> TYPE: DNA
<213> ORGANISM: Artificial Sequence
<220> FEATURE:
<223> OTHER INFORMATION: Amplicon Sequence

<400> SEQUENCE: 457
aagctacgag gaaaagaagt acacgatggg ggacgctcct gattatgaca gaagccagtg    60
gctgaatgaa aaattcaagc tgggcc                                        86

<210> SEQ ID NO 458
<211> LENGTH: 86
<212> TYPE: DNA
<213> ORGANISM: Artificial Sequence
<220> FEATURE:
<223> OTHER INFORMATION: Amplicon Sequence

<400> SEQUENCE: 458
aagctacgag gaaaagaagt atacgatggg ggacgctcct gactatgaca gaagccagtg    60
gctgaatgaa aaattcaagc tgggcc                                        86

<210> SEQ ID NO 459
<211> LENGTH: 86
<212> TYPE: DNA
<213> ORGANISM: Artificial Sequence
<220> FEATURE:
<223> OTHER INFORMATION: Amplicon Sequence

<400> SEQUENCE: 459
aagctatgtg gaaaagaagt acacgctggg ggacgctcct gactatgaca gaagccagtg    60
gctgaatgaa aaattcaagc tgggcc                                        86

```
<210> SEQ ID NO 460
<211> LENGTH: 86
<212> TYPE: DNA
<213> ORGANISM: Artificial Sequence
<220> FEATURE:
<223> OTHER INFORMATION: Amplicon Sequence

<400> SEQUENCE: 460
ctcttatgag gagaaacggt acacgtgcgg ggaagctcct gactatgatc gaagccaatg      60
gctggatgtg aaattcaagc tagacc                                          86

<210> SEQ ID NO 461
<211> LENGTH: 61
<212> TYPE: DNA
<213> ORGANISM: Artificial Sequence
<220> FEATURE:
<223> OTHER INFORMATION: Amplicon Sequence

<400> SEQUENCE: 461
tctgtgtccc agctcatttg ttcatgtgac agtatttcta tgtcaggcct gccatgagcg      60
g                                                                     61

<210> SEQ ID NO 462
<211> LENGTH: 61
<212> TYPE: DNA
<213> ORGANISM: Artificial Sequence
<220> FEATURE:
<223> OTHER INFORMATION: Amplicon Sequence

<400> SEQUENCE: 462
tctgtgtccc agctcattta ttagtgtgac agtatttcta tctcaggcct gccatgagca      60
g                                                                     61

<210> SEQ ID NO 463
<211> LENGTH: 58
<212> TYPE: DNA
<213> ORGANISM: Artificial Sequence
<220> FEATURE:
<223> OTHER INFORMATION: Amplicon Sequence

<400> SEQUENCE: 463
tgtattttca ttcccattaa ccactagcaa aagttatttc cttttattgt gaagagag        58

<210> SEQ ID NO 464
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 464
ggcaattccc accaatctta ggacacgatc caggcatccc acgtggaaaa ttcaattcct      60
agatggtaaa attt                                                       74

<210> SEQ ID NO 465
<211> LENGTH: 75
<212> TYPE: DNA
<213> ORGANISM: Artificial Sequence
<220> FEATURE:
<223> OTHER INFORMATION: Amplicon Sequence

<400> SEQUENCE: 465
atcaattccc caccaatcta cttatagaat cctgactccc cagggtatga attcactctc      60
```

```
tagacagtaa tggtt                                                      75

<210> SEQ ID NO 466
<211> LENGTH: 68
<212> TYPE: DNA
<213> ORGANISM: Artificial Sequence
<220> FEATURE:
<223> OTHER INFORMATION: Amplicon Sequence

<400> SEQUENCE: 466
atcagtcccc accaatcata ggaagtccta tgaaagctag caattcagtt cctagacaat     60
aaagtcat                                                              68

<210> SEQ ID NO 467
<211> LENGTH: 81
<212> TYPE: DNA
<213> ORGANISM: Artificial Sequence
<220> FEATURE:
<223> OTHER INFORMATION: Amplicon Sequence

<400> SEQUENCE: 467
aagaacccct gtctagaatc ttgtggaccc agttgctacc ttctacttat tttctttttt     60
ctcctaacac agcatcttct c                                               81

<210> SEQ ID NO 468
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 468
ctgggctgtg atgctgagat tgagtctgtg ttttgtgggt ggcaggtggg gagacagaag     60
aggagaagat tcgt                                                       74

<210> SEQ ID NO 469
<211> LENGTH: 74
<212> TYPE: DNA
<213> ORGANISM: Artificial Sequence
<220> FEATURE:
<223> OTHER INFORMATION: Amplicon Sequence

<400> SEQUENCE: 469
ttggggtgct atgctcagag tgagtctgtg ttttgtgggt ggcaggtggg gagacagaag     60 aggagaaagat tcgt                                                      74

<210> SEQ ID NO 470
<211> LENGTH: 78
<212> TYPE: DNA
<213> ORGANISM: Artificial Sequence
<220> FEATURE:
<223> OTHER INFORMATION: Amplicon Sequence

<400> SEQUENCE: 470 ctaattttg tattttgta agagacgggg ttttgccatg ttacccaggc tgatcctgaa       60
cttctgggct caaacagt                                                   78
```

GENES INVOLVED IN ESTROGEN METABOLISM

CROSS REFERENCE TO RELATED APPLICATIONS

This is a non-provisional application filed under 37 C.F.R. §1.53(b), claiming priority under 37 C.F.R. §119(e) to U.S. Provisional Patent Application Ser. No. 60/787,926, filed on Mar. 31, 2006 and to U.S. Provisional Patent Application Ser. No, 60/789,187, filed on Apr. 3, 2006, the entire disclosures of which are hereby expressly incorporated by reference.

This application contains a Sequence Listing, which was submitted as an ASCII text file tited "GHDX024DIV1" (95,000 bytes, created May 17,2012), and which is incorporated by reference in its entirety.

FIELD OF THE INVENTION

The present invention concerns genes that have been identified as being involved in estrogen metabolism, and are useful as diagnostic, prognostic and/or predictive markers in cancer. In particular, the present invention concerns genes the tumor expression levels of which are useful in the diagnosis of cancers associated with estrogen metabolism, and/or in the prognosis of clinical outcome and/or prediction of drug response of such cancers.

DESCRIPTION OF RELATED ART

Gene Expression Studies

Oncologists regularly confront treatment decisions regarding whether a cancer patient should receive treatment and, if so, what treatment to choose. These oncologists typically have a number of treatment options available to them, including different combinations of chemotherapeutic drugs that are characterized as "standard of care." Because these "standard of care"chemotherapeutic drugs such as cyclophosphamide, methotrexate, 5-fluorouracil, anthracyclines, taxanes, have limited efficacy and a spectrum of often severe side effects, it is important to identify those patients having the highest likelihood of a positive clinical outcome without chemotherapy (patients with good prognosis) in order to minimize unnecessary exposure of these patients to the toxic side effects of the chemotherapeutic agents.

For those patients with a poor prognosis it is then important to predict the likelihood of beneficial response in individual patients to particular chemotherapeutic drug regimens. Identification of those patients most likely to benefit from each available treatment will enhance the utility of "standard of care"treatments, and facilitate the development of further, more personalized treatment options, including the use of already approved drugs that had previously not been recommended for the treatment of a particular cancer. The identification of patients who are more likely or less likely to need and respond to available drugs thus could increase the net benefit these drugs have to offer and decrease net morbidity and toxicity, via more intelligent patient selection.

Most diagnostic tests currently used in clinical practice are single analyte, and therefore do not capture the potential value of knowing relationships between dozens of different markers. Moreover, diagnostic tests are often based on immunohistochemistry, which is not quantitative. Immunohistochemistry often yields different results in different laboratories, in part because the reagents are not standardized, and in part because the interpretations are subjective. RNA-based tests, while potentially highly quantitative, have not been used because of the perception that RNA is destroyed in tumor specimens as routinely prepared, namely fixed in formalin and embedded in paraffin (FPE), and because it is inconvenient to obtain and store fresh tissue samples from patients for analysis.

Over the last two decades molecular biology and biochemistry have revealed hundreds of genes whose activities influence the behavior of tumor cells, their state of differentiation, and their sensitivity or resistance to certain therapeutic drugs. However, with a few exceptions, the status of these genes has not been exploited for the purpose of routinely making clinical decisions about drug treatments. In the last few years, several groups have published studies concerning the classification of various cancer types by microarray gene expression analysis of thousands of genes (see, e.g. Golub et al., Science 286:531-537 (1999); Bhattacharjae et al., Proc. Natl. Acad. Sci. USA 98:13790-13795 (2001); Chen-Hsiang et al., Bioinformatics 17 (Suppl. 1):S316-S322 (2001); Ramaswamy et al., Proc. Natl. Acad. Sci. USA 98:15149-15154 (2001); Martin et al., Cancer Res. 60:2232-2238 (2000); West et al., Proc. Natl. Acad. Sci. USA 98:11462-114 (2001); Sorlie et al., Proc. Natl. Acad. Sci. USA 98:10869-10874 (2001); Yan et al., Cancer Res. 61:83.75-8380 (2001)). However, these studies have not yet yielded tests routinely used in clinical practice, in large part because microarrays require fresh or frozen tissue RNA and such specimens are not present in sufficient quantity to permit clinical validation of identified molecular signatures.

In the past three years, it has become possible to profile gene expression of hundreds of genes in formalin-fixed paraffin-embedded (FPE) tissue using RT-PCR technology. Methods have been described that are highly sensitive, precise, and reproducible (Cronin et al., Am. J. Pathol. 164:35-42 (2004); PCT Publication No. WO 2003/078,662; WO 2004/071,572; WO 2004/074,518; WO 2004/065,583; WO 2004/111,273; WO 2004/111,603; WO 2005/008,213; WO 2005/040,396; WO 2005/039,382; WO 2005/064,019, the entire disclosures of which are hereby expressly incorporated by reference). Because thousands of archived FPE clinical tissue specimens exist with associated clinical records, such as survival, drug treatment history, etc., the ability to now quantitatively assay gene expression in this type of tissue enables rapid clinical studies relating expression of certain genes to patient prognosis and likelihood of response to treatments. Using data generated by past clinical studies allows for rapid results because the clinical events are historical. In contrast, for example, if one wished to carry out a survival study on newly recruited cancer patients one would generally need to wait for many years for statistically sufficient numbers of deaths to have occurred.

Breast Cancer Prognosis and Prediction

Breast cancer is the most common type of cancer among women in the United States, and is the leading cause of cancer deaths among women between the ages of 40 and 59.

Because current tests for prognosis and for prediction of chemotherapy response are inadequate, breast cancer treatment strategies vary between oncologists (Schott and Hayes, J. Clin. Oncol. PMID 15505274 (2004); Hayes, Breast 12;543-9 (2003)). The etiology of certain types of human breast cancer involves certain steroid hormones, called estrogens. Estrogens are believed to cause proliferation of breast epithelial cells primarily via binding of hormones to estrogen receptors, resulting in modification of the cellular transcription program. For these reasons, one of the most commonly used markers in selecting a treatment option for breast cancer patients is the estrogen receptor 1 (ESR1). Estrogen receptor-positive (ESR1+) tumors are generally less aggressive than estrogen receptor negative (ESR1−) tumors, and can often be successfully treated with anti-estrogens such as tamoxifen (TAM). Conversely, ESR1− tumors are typically more aggressive and are resistant to anti-estrogen treatment. Thus, aggressive chemotherapy is often provided to patients for ESR1− tumors. Based on this simple understanding, assays for ESR1 levels by immunohistochemistry are currently utilized as one parameter for making treatment decisions in breast cancer. Generally, lymph node negative patients whose tumors are found to be ESR1 positive are treated with an anti-estrogen drug, such as tamoxifen (TAM), and patients whose tumors are found to be ESR1 negative are treated with chemotherapy. However, often because of the uncertainty in the currently used diagnostic procedures, ESR1 positive patients are also prescribed chemotherapy in addition to anti-estrogen therapy, accepting the toxic side effects of chemotherapy in order to modestly decrease the risk of cancer recurrence. Toxicities include, neuropathy, nausea and other gastrointestinal symptoms, hair loss and cognitive impairment. Recurrence is to be feared because recurrent breast cancer is usually metastatic and poorly responsive to treatment.

The human GSTM (GSTμ) gene family consists of five different closely related isotypes, GSTM1-GSTM5. GSTM proteins conjugate glutathione to various electrophilic small molecules, facilitating clearance of the electrophiles from cells. Evidence exists that several metabolites of estrogen, including estrogen semi-quinones and estrogen quinones (catechol estrogens), are toxic and mutagenic (Cavalieri et al., *Proc Natl Acad Sci* 94:10937-42,1997). The activity of one or more GSTM enzymes may limit mutational damage caused by these estrogen metabolites.

We have reported five independent clinical studies in which GSTM gene expression was examined by quantitative RT-PCR in formalin-fixed, paraffin embedded primary breast cancer tissues. GSTM expression correlated strongly with favorable clinical outcome in each of these studies (Esteban et al., *Prog. Proc Am Soc. Clin. Oncol.* 22:850 abstract, 2003; Cobleigh et al., *Clin Cancer Res* (in press); Paik et al., *Breast Cancer Res. Treat.* 82:A16 abstract, 2003; Habel et al, *Breast. Cancer Res. Treat.* 88:3019 abstract, 2004: Paik et al, *N Engl J Med* 351:2817-26, 2004).

In these studies the probe used could not discriminate between GSTM1 and several other GSTM family members as a result of the strong sequence similarity of the GSTM genes, amplicon size limitations and the stringent sequence criteria for probe-primer design, leaving the possibility that several of the GSTM genes may be favorable markers.

Clearly, a need exists to identify those patients who are at substantial risk of cancer recurrence (i.e., to provide prognostic information) and/or likely to respond to chemotherapy (i.e., to provide predictive information). Likewise, a need exists to identify those patients who do not have a significant risk of recurrence, and/or who are unlikely to respond to chemotherapy, as these patients should be spared needless exposure to these toxic drugs.

SUMMARY OF THE INVENTION

The present invention is based, at least in part, on the recognition that since estrogens may contribute to tumorigenesis and tumor progression via pathways that are ESR1 independent, treatment decisions based primarily or solely on the ESR1 status of a patient are unsatisfactory.

One aspect of the invention is directed to a method of predicting clinical outcome for a subject diagnosed with cancer, comprising determining evidence of the expression level of one or more predictive RNA transcripts listed in Table 8, or their expression products, in a biological sample comprising cancer cells obtained from said subject, wherein evidence of increased expression of one or more of the genes listed in Table 8, or the corresponding expression product, indicates a decreased likelihood of a positive clinical outcome. In one embodiment the subject is a human patient. In one embodiment the expression level is obtained by a method of gene expression profiling. In one embodiment the method of gene expression profiling is a PCR-based method. In one embodiment the expression levels are normalized relative to the expression levels of one or more reference genes, or their expression products. In one embodiment the clinical outcome is expressed in terms of Recurrence-Free Interval (RFI), Overall Survival (OS), Disease-Free Survival (DFS), or Distant Recurrence-Free Interval (DRFI). In one embodiment the cancer is selected from the group consisting of breast cancer or ovarian cancer. In one embodiment the cancer is breast cancer.

In one embodiment, the method of predicting clinical outcome for a subject diagnosed with cancer comprises determining evidence of the expression level of at least two of said genes, or their expression products. In another embodiment, the expression levels of at least three of said genes, or their expression products are determined. In yet another embodiment, the expression levels of at least four of said genes, or their expression products are determined. In a further embodiment, the expression levels of at least five of said genes, or their expression products are determined.

The method may further comprise the step of creating a report summarizing said prediction.

Another aspect of the invention is a method of predicting the duration of Recurrence-Free Interval (RFI) in a subject diagnosed with breast cancer, comprising determining the expression level of one or more predictive RNA transcripts listed in Table 8 or their expression products, in a biological sample comprising cancer cells obtained from said subject, wherein evidence of increased expression of one or more of the genes listed in Table 8, or the corresponding expression product, indicates that said RFI is predicted to be shorter. In one embodiment the subject is a human patient. In another aspect the expression level is obtained by a method of gene expression profiling. In one embodiment the method of gene expression profiling is a PCR-based method. In one embodiment the expression levels are normalized relative to the expression levels of one or more reference genes, or their expression products. In one embodiment the clinical outcome is expressed in terms of Recurrence-Free Interval (RFI), Overall Survival (OS), Disease-Free Survival (DFS), or Distant Recurrence-Free Interval (DRFI). In one embodiment the cancer is selected from the group consisting of breast cancer or ovarian cancer. In one embodiment the cancer is breast cancer.

One aspect of the method of predicting the duration of Recurrence-Free Interval (RFI), for a subject diagnosed with cancer, comprises determining evidence of the expression level of at least two of said genes, or their expression products. In one embodiment the expression levels of at least three of said genes, or their expression products are determined. In another embodiment the expression levels of at least four of said genes, or their expression products are determined. In another embodiment the expression levels of at least five of said genes, or their expression products are determined.

One aspect of the methods of this invention is that if the RFI is predicted to be shorter, said patient is subjected to further therapy following surgical removal of the cancer. In one aspect, the therapy is chemotherapy and/or radiation therapy.

One aspect of the methods of this invention is that the expression level of one or more predictive RNA transcripts or their expression products of one or more genes selected from the group consisting of CAT, CRYZ, CYP4Z1, CYP17A1, GPX1, GPX2, GSTM1, GSTM2, GSTM3, GSTM4, GSTM5, GSTP1, NQO1, PRDX3, and SC5DL is determined.

One aspect of the methods of this invention is that the expression level of one or more predictive RNA transcripts or their expression products of one or more genes selected from the group consisting of GSTM1, GSTM2, GSTM3, GSTM4, GSTM5 and GSTP1 is determined.

One aspect of the methods of this invention is that the expression level of one or more predictive RNA transcripts or their expression products of one or more genes selected from the group consisting of GSTM2 and GSTM4 is determined.

One aspect of the methods of this invention is that the expression level of one or more predictive RNA transcripts or their expression products of one or more genes selected from the group consisting of GSTM1 and GSTM3 is determined.

One aspect of the methods of this invention is that the expression level of one or more predictive RNA transcripts or their expression products of one or more genes selected from the group consisting of CAT, PRDX3, GPX1, and GPX2 is determined.

One aspect of the methods of this invention is that the expression level of one or more predictive RNA transcripts or their expression products of one or more genes selected from the group consisting of PRDX3, GPX1 and GPX2 is determined.

One aspect of the methods of this invention is that the expression level of one or more predictive RNA transcripts or their expression products of one or more genes selected from the group consisting of GPX1 and GPX2 is determined.

One aspect of the methods of this invention is that the expression level of one or more predictive RNA transcripts or their expression products of one or more genes selected from the group consisting of CRYZ and NQO1 is determined.

One aspect of the methods of this invention is that the expression level of one or more predictive RNA transcripts or their expression products of CYP17A1 is determined.

One aspect of the methods of this invention is that the expression level of one or more predictive RNA transcripts or their expression products of one or more genes selected from the group consisting of SC5DL and CYP4Z1 is determined.

In another aspect, this invention concerns a method for preparing a personalized genomics profile for a patient comprising the steps of (a) subjecting RNA extracted from a tissue obtained from the patient to gene expression analysis;
(b) determining the expression level in the tissue of one or more genes selected from the gene set listed in Table 8 wherein the expression level is normalized against a control gene or genes and optionally is compared to the amount found in a cancer reference set and
(c) creating a report summarizing the data obtained by said gene expression analysis.

Another embodiment of this invention is a method for amplification of a gene listed in Table 8 by polymerase chain reaction (PCR) comprising performing said per by using amplicons listed in Table 7 and a primer-probe set listed in Table 6.

Another embodiment of this invention is a PCR primer-probe set listed in Table 6.

Another embodiment of this invention is a PCR amplicon listed in Table 7.

BRIEF DESCRIPTION OF THE FIGURES AND TABLES

FIG. 1 shows the sequence alignment of the GSTM1 and GSTM2 amplicons with the corresponding regions of other GSTM family members.

DETAILED DESCRIPTION OF THE PREFERRED EMBODIMENT

A. Definitions

Figure 2:
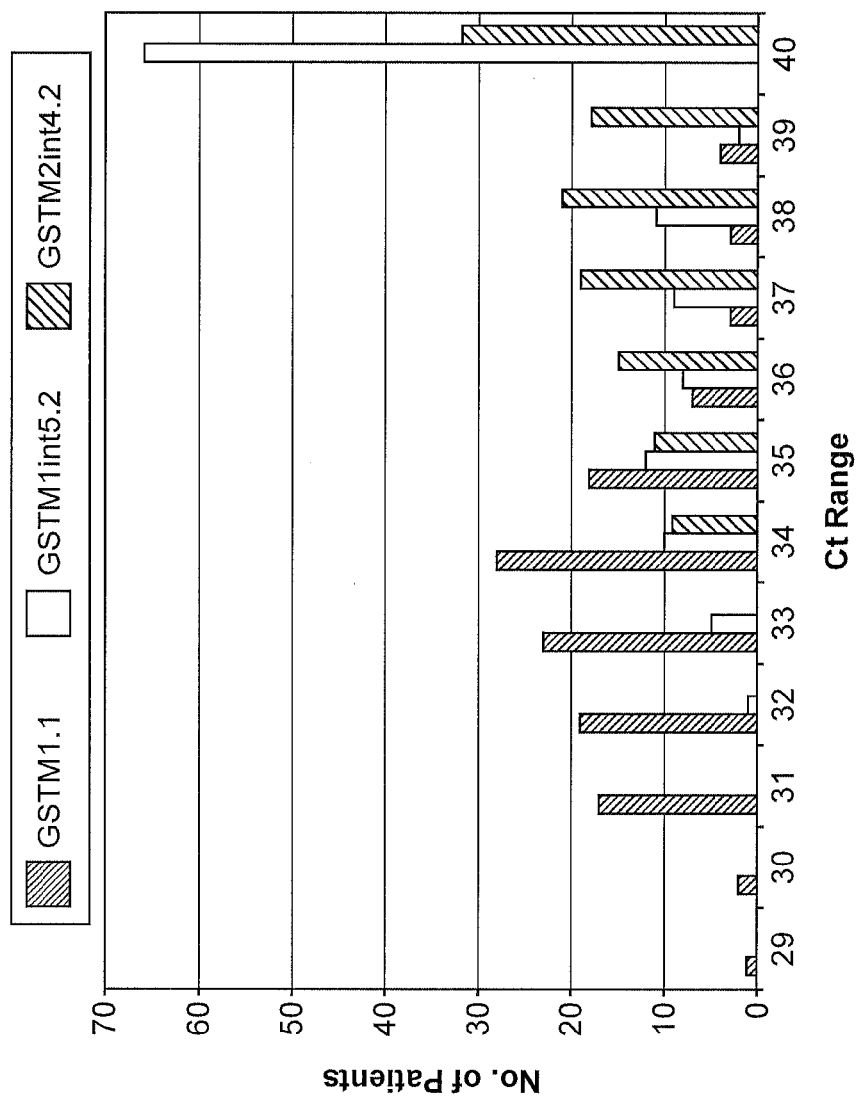
FIG. 2 shows the distribution of RT-PCR signals as CT values (X-axis) across the 125 breast cancer patients (Y-axis) for GSTM1.1, GSTM1int5.2 and GSTM2int4.2.

Unless defined otherwise, technical and scientific terms used herein have the same meaning as commonly understood by one of ordinary skill in the art to which this invention belongs, Singleton et al., Dictionary of Microbiology and Molecular Biology 2nd ed., J. Wiley & Sons (New York, N.Y. 1994); and Webster's New World™ Medical Dictionary, 2nd Edition, Wiley Publishing Inc., 2003, provide one skilled in the aft with a general guide to many of the terms used in the present application. For purposes of the present invention, the following terms are defined below.

The term RT-PCR has been variously used in the art to mean reverse-transcription PCR (which refers to the use of PCR to amplify mRNA by first converting mRNA to double stranded cDNA) or real-time PCR (which refers to ongoing monitoring in 'real-time' of the amount of PCR product in order to quantify the amount of PCR target sequence initially present. The term 'RT-PCR' means reverse transcription PCR. The term quantitative RT-PCR (qRT-PCR) means real-time PCR applied to determine the amount of mRNA initially present in a sample.

The term "clinical outcome" means any measure of patient status including those measures ordinarily used in the art, such as disease recurrence, tumor metastasis, overall survival, progression-free survival, recurrence-free survival, and distant recurrence-free survival. Distant recurrence-free survival (DRFS) refers to the time (in years) from surgery to the first distant recurrence.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "gene expression" describes the conversion of the DNA gene sequence information into transcribed RNA (the initial unspliced RNA transcript or the mature mRNA) or the encoded protein product. Gene expression can be monitored by measuring the levels of either the entire RNA or protein products of the gene or subsequences.

The phrase "gene amplification" refers to a process by which multiple copies of a gene or gene fragment are formed in a particular cell or cell line. The duplicated region (a stretch of amplified DNA) is often referred to as "amplicon." Often, the amount of the messenger RNA (mRNA) produced, i.e., the level of gene expression, also increases in the proportion of the number of copies made of the particular gene expressed.

Prognostic factors are those variables related to the natural history of breast cancer, which influence the recurrence rates and outcome of patients once they have developed breast cancer. Clinical parameters that have been associated with a worse prognosis include, for example, lymph node involvement, increasing tumor size, and high grade tumors. Prognostic factors are frequently used to categorize patients into subgroups with different baseline relapse risks. In contrast, treatment predictive factors are variables related to the likelihood of an individual patient's beneficial response to a treatment, such as anti-estrogen or chemotherapy, independent of prognosis.

The term "prognosis" is used herein to refer to the likelihood of cancer-attributable death or cancer progression, including recurrence and metastatic spread of a neoplastic disease, such as breast cancer, during the natural history of the disease. Prognostic factors are those variables related to the natural history of a neoplastic diseases, such as breast cancer, which influence the recurrence rates and disease outcome once the patient developed the neoplastic disease, such as breast cancer. In this context, "natural outcome" means outcome in the absence of further treatment. For example, in the case of breast cancer, "natural outcome" means outcome following surgical resection of the tumor, in the absence of further treatment (such as, chemotherapy or radiation treatment). Prognostic factors are frequently used to categorize patients into subgroups with different baseline risks, such as baseline relapse risks.

The term "prediction" is used herein to refer to the likelihood that a patient will respond either favorably or unfavorably to a drug or set of drugs, and also the extent of those responses. Thus, treatment predictive factors are those variables related to the response of an individual patient to a specific treatment, independent of prognosis. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as anti-estrogen therapy, such as TAM treatment alone or in combination with chemotherapy and/or radiation therapy.

The term "long-term" survival is used herein to refer to survival for at least 3 years, more preferably for at least 8 years, most preferably for at least 10 years following surgery mother treatment.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, breast cancer, ovarian cancer, colon cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

In the context of the present invention, reference to "at least one," "at least two," "at least three," "at least four," "at least five," etc. of the genes listed in any particular gene set means any one or any and all combinations of the genes listed.

The term "node negative" cancer, such as "node negative" breast cancer, is used herein to refer to cancer that has not spread to the lymph nodes.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product (B, Lewin. *Genes IV* Cell Press, Cambridge Mass. 1990). In theory the term "intron" refers to any segment of DNA that is transcribed but removed from within the transcript by splicing together the exons on either side of it. Operationally, exon sequences occur in the mRNA sequence of a gene as defined by Ref. SEQ ID numbers. Operationally, intron sequences are the intervening sequences within the genomic DNA of a gene, bracketed by exon sequences and having GT and AG splice consensus sequences at their 5' and 3' boundaries.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994). The practice of the present invention will also employ, unless otherwise indicated, conventional techniques of statistical analyis such as the Cox Proportional Hazards model (see, e.g. Cox, D. R., and Oakes, D. (1984), *Analysis of Survival Data*, Chapman and Hall, London, N.Y.). Such techniques are explained fully in the literature.

B.1. General Description of the Invention

As discussed before, the present invention is based, at least in part, on the recognition that since estrogens may contribute to tumorigenesis and tumor progression via pathways that are ESR1 independent, treatment decisions based primarily or solely on the ESR1 status of a patient are unsatisfactory.

Estrogen Metabolism

It is known that certain pathways of estrogen degradation involve the production of electrophilic estrogen metabolites as well as reactive oxygen species (ROS), both of which have the potential to damage cellular DNA and thus contribute to carcinogenesis (Cavalieri et al., *Cell. Mol. Life Sci.* 59: 665-81 (2002); Thompson and Ambrosone, *J. Natl. Cancer Inst.* 27: 125-34 (2000)).

The present invention is based on the identification of genes that are believed to be involved in the metabolism and/or clearance of estrogen, and thus in the control of intracellular concentration of electrophilic estrogen metabolites. In a specific embodiment, gene specific probe primer sets were designed based on the exon and introns sequences of the genes identified. These probe primer sets may be used in conjuction with a variety of clinical samples to identify particular genes within the estrogen metabolism group which are prognostic of outcome in a particular type of cancer and/or have predictive value in determining patient response to a particular treatment modality.

Estrogens, including the principle active hormones, estrone and estradiol, can be converted to catechol estrogens (CE) via either 2-hydroxylation by cytochrome P4501A1 (CYP1A1) or via 4-hydroxylation by cytochrome P4501B1 (CYP1B1). These catechol estrogens (CE) can be further metabolized to CE semiquinones and then to CE quinones, which compounds are electrophiles and are proven or potential mutagens. (Mitrunen and Hirvonen, *Mutation Research*, 544: 9-41 (2003); Lieher, *Endocrine Reviews*, 21:40-54 (2000)). Furthermore, concomitant with the conversion of estrogen semiquinones to estrogen quinones, molecular oxygen is converted to highly reactive superoxide anion, which also can damage DNA.

The presence of electrophilic estrogen metabolites and reactive oxygen species could cause mutations in normal cells over time, resulting in tumorigenesis and could further cause new mutations in existing tumor cells that may be already compromised in their ability to repair damage to their DNA. The resulting increased burden of mutations could result in emergence of more aggressive clones in the tumor, more tumor aneuploidy and heterogeneity, with negative consequences for the health of the patient. Cellular metabolic strategies that would minimize the formation of mutagenic estrogen metabolites or increase the efficiency of their removal via conversion or clearance would then minimize mutagenic effects and result in more favorable prognosis.

Although a number of studies have been carried out to determine the effect on breast cancer predisposition risk of allelic variation in estrogen metabolizing genes, little has been done regarding the potential effect on cancer predisposition or prognosis, of expression levels of the various genes that affect cellular levels of mutatgenic estrogen metabolites.

One alternative to the catechol/quinone pathway discussed above is the conversion, by the enzyme cathecol-O-methyl transferase (COMT), of estrogen catechols to 2-methoxy and 4-methoxy estrogens, compounds that are much less reactive than the quinones and more readily cleared from the cell.

Mutagenic catechol estrogen quinones can be converted back to catechol estrogens through the action of a NADPH-dependent quinone reductase (CRYZ), making them re-available for metabolism via COMT.

Direct clearance of both CE semiquinones and CE quinones can be initiated by conjugation of the metabolites with glutathione catalyzed by glutathione-S-transferase (GST) enzymes. The GST protein family includes GST mu enzymes (GSTM1, GSTM2, GSTM3, GSTM4 and GSTM5), GST pi enzyme GSTP1 and GST theta enzyme GSTT1. In addition to the above enzymes, membrane-associated glutathione-S-transferase enzymes that catalyze the conjugation of glutathione to electrophiles; including MGST1 and MGST3, have been identified. Membrane-associated glutathione-S-transferase may also catalyze the reduction of lipid hydroperoxides (see below).

Glutathione, required by GST enzymes, is a tripeptide synthesized from amino acids in a process the rate-limiting step of which is catalyzed by gamma-glutamylcysteine synthetase, an enzyme composed of a catalytic subunit (GCLC) and a regulatory subunit (GCLM) that are endoded by separate genes.

Various other metabolites arising from the synthesis and degradation of estrogens are further modified by enzymatic sulfation or glucuronidation as a prerequisite for their clearance from the cell. Variation in the levels of the enzymes that carry out these modifications may shift the intracellular concentrations of estrogen and its electrophilic metabolites. For example, SULT1E1 is a member of the sulfotransferase family that preferentially sulfates estrone at the 3 position in a detoxification and clearance step. Another family of proteins, the UDP-glucuronosyltransferases (UGTs), participates in the clearance of a wide variety of compounds, and includes UGT1A3 and UGT2b7, the substrates of which include estrone and 2-hydroxyestrone.

The forward and reverse conversion between catechol estrogens and catechol estrogen quinones establishes the possibility of redox cycling, which results in continuous generation of superoxide anion ($O_2^-$) Cells have established strategies for detoxification of $O_2^-$ produced by estrogen metabolism and other cellular processes. $O_2^-$ is initially converted to molecular oxygen ($O_2$)+hygrogen peroxide ($H_2O_2$), another ROS, by a superoxide dismutase (SOD), which occur in cytoplamic (SOD1), mitochondrial (SOD2), and extracellular (SOD3) forms. The H2O2 produced by superoxide dismutase is further metabolized to $H_2O_2$ and molecular oxygen by catalase (CAT). The various enzymes of the peroxiredoxin family, including peroxiredoxins 2,3,4 and 6 (PRDX2, PRDX3, PRDX4 and PRDX6) also catalyze the inactivation of $H_2O_2$ as well as the reduction of organic hydroperoxides that may have been generated in the presence of ROS. Glutathione peroxidases (GPX1 and GPX2) are also involved in the detoxification of $H_2O_2$. Allelic variants of GPX1 have been associated with breast cancer risk (Knight et al., Cancer Epidemiol. Biomarkers Prev. 13: 146-9 (2004).

Hydrogen peroxide, in the presence of certain transition metal ions, gives rise to hydroxide ions, which not only can damage DNA directly but can also initiate lipid peroxidation, giving rise to lipid hydroperoxides. These lipid hydroperoxides are believed to accelerate the conversion of catechol estrogen to semiquinones and quinones by cytochrome P450 (Cavalieri CMLS), thus amplifying the production of electrophilic estrogen metabolites. Both peroxiredoxins (in addition to inactivating H202) and membrane-associated glutathione-S-transferases (in addition to conjugating glutathione to electrophilic estrogen metabolites) can catalyze the reduction of organic hydroperoxides by the action of ROS and therefore slow the production of CE semiquinones and CE quinines.

Figure 7:
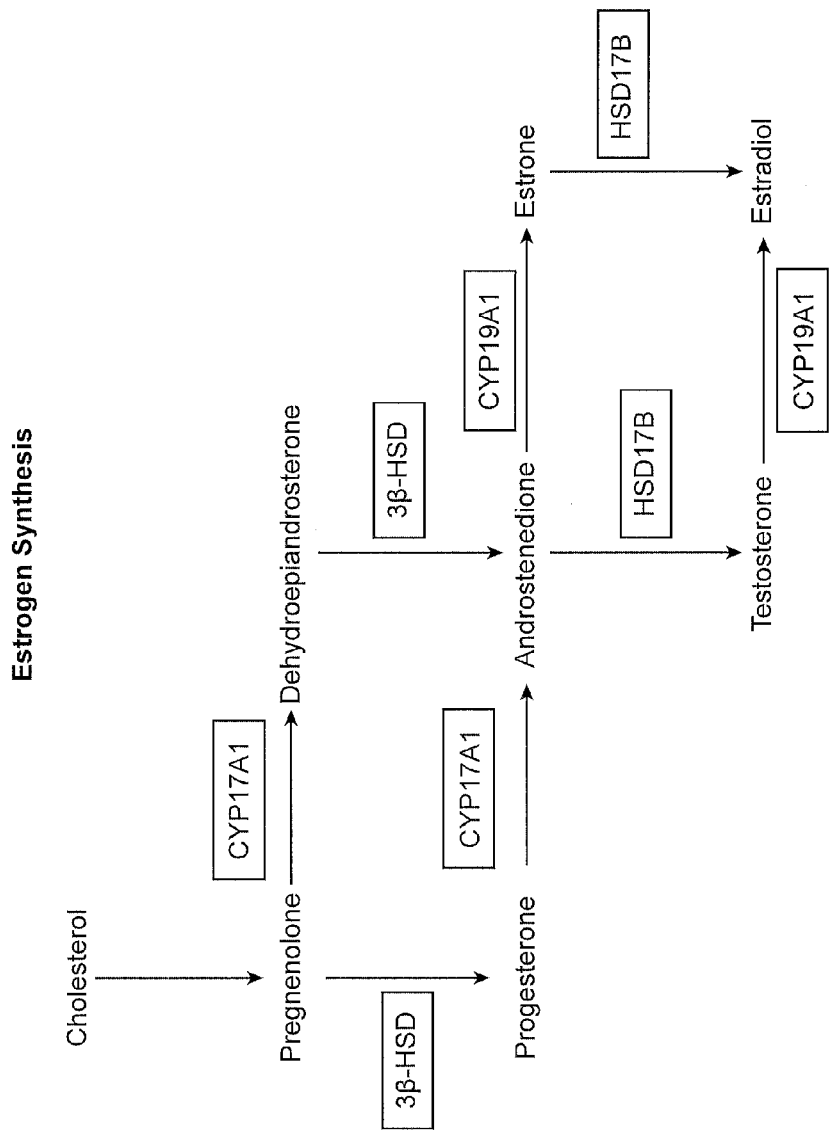
FIG. 7 shows specific pathways for the synthesis of key estrogens, estrone and estradiol, from cholesterol.

The concentration of estrogen metabolites is affected by the rate estrogen synthesis as well as the routes and rates of degradation and clearance. Estrogen is synthesized from cholesterol via a complex series of reactions. Cholesterol is first metabolized in C21 steroid metabolism pathways to pregnenolone. As shown in FIG. 7, pregnenolone is then converted to androst-4-ene-3,17-dione by the action of a 3β-hydroxysteroid dehydrogenase and a cytochrome P450 (CYP17A1) in either order. Androst-4-ene-3,17-dione then gives rise to the key estrogens, estrone and estradiol through the sequential actions of a 17β-hydroxysteroid dehydrogenase (HSD17B1, HSD17B2, and HSD17B4) and the cytochrome P450 enzyme, aromatase (CYP19A1) in either order. Both estrone and estradiol are subject to the degradation processes discussed above.

Entry of estrogen precursors into the estrogen synthesis pathway can be limited by the alternate conversion of pregnenolone to progesterone and then to 20α-hydroxyprogesterone by 20α-hydroxysteroid dehydrogenase (AKR1C3), reducing the amount of androst-4-ene-3,17-dione available for conversion to estrogens.

The Invention

The present invention takes the novel approach of measuring the mRNA expression level of numerous genes that can affect the cellular concentration of mutagenic estrogen metabolites at equilibrium, and identifying markers of predisposition and prognosis in cancer the pathogenesis of which involves estrogen metabolism, such as breast cancer.

In particular, quantitative gene expression analysis performed in accordance with the present invention resulted in the identification of molecular indicators of prognosis in cancer. Based on analysis of the relationship between gene expression in the sample set and DRFS, a set of genes has been identified, the expression levels of which are indicative of outcome after tumor resection and any accompanying therapy with tamoxifen and/or adjuvant chemotherapy. Outcome may be manifest in various measurements including survival, recurrence-free survival and distant recurrence-free survival (DRFS), all of which are within the scope of the invention.

The genes identified in accordance with the present invention, or any gene group formed by particular combination of such genes can be used alone, or can be used together with one or more further diagnostic, prognostic and/or predictive indicators. Other diagnostic, prognostic and predictive indicators may include the expression of other genes or gene groups and may also include clinical variables including tumor size, stage and grade. Other diagnostic, prognostic or predictive indicators specifically include, individually or in any combination, the genes and genes sets disclosed in any of the following PCT Publications: WO 2003/078,662; WO 2004/071, 572; WO 2004/074,518; WO 2004/065,583; WO 2004/111, 273; WO 2004/111,603; WO 2005/008,213; WO 2005/040, 396; WO 2005/039,382; WO 2005/064,019.

Alone or in combination with other cancer markers, such as diagnostic, prognostic and/or predictive indicators, the genes and gene groups of the present invention can be used to calculate Recurrence Score, an aggregate indication, based on multiple prognostic indicators, of the likelihood of a particular clinical outcome and/or drug responsiveness. Thus, for example, for an individual patient it is possible to provide a quantitative estimate of likelihood of outcome. This information can be utilized by the patient and treating physicians to make treatment decisions, in particular decisions regarding whether or not to treat the patient with drugs that lead to appreciable adverse events.

In various embodiments of the inventions, various technological approaches are available for determination of expression levels of the disclosed genes, including, without limitation, RT-PCR, microarrays, serial analysis of gene expression (SAGE) and Gene Expression Analysis by Massively Parallel Signature Sequencing (MPSS), which will be discussed in detail below. In particular embodiments, the expression level of each gene may be determined in relation to various features of the expression products of the gene including exons, introns, protein epitopes and protein activity. In other embodiments, the expression level of a gene may be inferred from analysis of the structure of the gene, for example from the analysis of the methylation pattern of gene's promoter(s).

B.2 Gene Expression Profiling

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

a. Reverse Transcriptase PCR (RT-PCR)

Of the techniques listed above, the most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include Master-Pure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonueleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is detected at the CCD. The system includes software for running the instrument and for analyzing the data.

5'-Nuclease assay data are initially expressed as $C_T$, or the threshold cycle. As discussed above, fluorescence values are recorded during every cycle and represent the amount of product amplified to that point in the amplification reaction. The point when the fluorescent signal is first recorded as statistically significant is the threshold cycle ($C_T$).

To minimize errors and the effect of sample-to-sample variation, RT-PCR is usually performed using one or more reference genes as internal standards. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPD) and β-actin (ACTB).

A more recent variation of the RT-PCR technique is real time quantitative RT-PCR (q RT-PCR), which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

The steps of a representative protocol for profiling gene expression using fixed, paraffin-embedded tissues as the RNA source, including mRNA isolation, purification, primer extension and amplification are given in various published journal articles {(for example: T. E, Godfrey et al. J. Molec. Diagnostics 2: 84-91 (2000); K. Specht et al., Am. J. Pathol. 158: 419-29 (2001); Cronin et al., Am J Pathol 164:35-42 (2004)}. Briefly, a representative process starts with cutting about 10 µm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR.

b. Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

c. Serial Analysis of Gene Expression (SAGE)

Serial analysis of gene expression (SAGE) is a method that allows the simultaneous and quantitative analysis of a large number of gene transcripts, without the need of providing an individual hybridization probe for, each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

d. Gene Expression Analysis by Massively Parallel Signature Sequencing (MPSS)

This method, described by Brenner et al., *Nature Biotechnology* 18:630-634 (2000), is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

e. General Description of the mRNA Isolation, Purification and Amplification

The steps of a representative protocol for profiling gene expression using fixed, paraffin-embedded tissues as the RNA source, including mRNA isolation, purification, primer extension and amplification are provided in various published journal articles (for example: T. E. Godfrey et al,. *J. Molec. Diagnostics* 2: 84-91 [2000]; K. Specht et al., *Am. J. Pathol.* 158: 419-29 [2001]). Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific-promoters followed by RT-PCR. Finally, the data are analyzed to identify the best treatment option(s) available to the patient on the basis of the characteristic gene expression pattern identified in the tumor sample examined, dependent on the predicted likelihood of cancer recurrence.

f. Reference Gene Set

An important aspect of the present invention is to use the measured expression of certain genes by breast cancer tissue to provide prognostic or predictive information. For this purpose it is necessary to correct for (normalize away) both differences in the amount of RNA assayed and variability in the quality of the RNA used. Well known housekeeping genes such as β-actin, GAPD, GUS, RPLO, and TFRC can be used as reference genes for normalization. Reference genes can also be chosen based on the relative invariability of their expression in the study samples and their lack of correlation with clinical outcome. Alternatively, normalization can be based on the mean or median signal ($C_T$) of all of the assayed genes or a large subset thereof (global normalization approach). Below, unless noted otherwise, gene expression means normalized expression.

g. Primer and Probe Design

According to one aspect of the present invention, PCR primers and probes are designed based upon intron sequences present in the gene to be amplified. Accordingly, the first step in the primer/probe design is the delineation of intron sequences within the genes. This can be done by publicly available software, such as the DNA BLAT software developed by Kent, W. J., *Genome Res.* 12(4):656-64 (2002), or by the BLAST software including its variations. Subsequent steps follow well established methods of PCR primer and probe design.

In order to avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386).

The most important factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. Primerselect: Primer and probe design. *Methods Mol. Biol.* 70:520-527 (1997), the entire disclosures of which are hereby expressly incorporated by reference.

B.3 Sources of Biological Material

Treatment of cancer often involves resection of the tumor to the extent possible without severely compromising the biological function of the patient. As a result, tumor tissue is typically available for analysis following initial treatment of the tumor, and this resected tumor has most often been the sample used in expression analysis studies.

Expression analysis can also be carried out on tumor tissue obtained through other means such as core, fine needle, or other types of biopsy.

For particular tumor types, tumor tissue is appropriately obtained from biological fluids using methods such as fine needle aspiration, bronchial lavage, or transbronchial biopsy.

Particularly in relatively advanced tumors, circulating tumor cells (CTC) are sometimes found in the blood of cancer patients. CTC recovered from blood can also be used as a source of material for expression analysis.

Cellular constituents, including RNA and protein, derived from tumor cells have been found in biological fluids of cancer patients, including blood and urine. Circulating nucleic acids and proteins may result from tumor cell lysis and may be subjected to expression analysis.

B.3 Algorithms and Statistical Methods

When quantitative RT-PCR (qRT-PCR) is used to measure mRNA levels, mRNA amounts are expressed in $C_T$ (threshold cycle) units (Held et al., Genome Research 6:986-994 (1996)). The averaged sum of $C_T$s for the reference mRNAs is arbitrarily set (e.g. to zero), and each measured test mRNA $C_T$ is given relative to this fixed reference. For example, if, for a particular patient tumor specimen the average of $C_T$s of the reference genes found to be 31 and $C_T$ of test gene X is found to be 35, the reported value for gene X is −4 (i.e. 31-35).

The normalized data can be used to analyze correlation between the expression level of particular mRNAs and clinical outcome. Standard statistical methods can be applied to identify those genes, for which the correlation between expression and outcome, in a univariate analysis, is statistically significant. These genes are markers of outcome, given the existing clinical status. Multivariate analysis can be applied to identify sets of genes, the expression levels of which, when used in combination, are better markers of outcome than the individual genes that constitute the sets.

Further, it is possible to define groups of genes known or suspected to be associated with particular aspects of the molecular pathology of cancer. A gene can be assigned to a particular group based either on its known or suspected role in a particular aspect of the molecular biology of cancer or based on its co-expression with another gene already assigned to a particular group. Co-pending U.S. Patent Application 60/561,035 defines several such groups and further shows that the definition of such groups (also termed axis or subset) is useful in that it supports particular methods of data analysis and the elaboration of mathematical algorithms, which in turn yields a more powerful predictors of outcome than can be formulated if these groups are not defined.

In breast cancer, steroid metabolism, including synthesis and degradation of steroids and clearance of intermediates is an aspect of the molecular pathology of cancer the importance of which has not been adequately appreciated. Genes involved in steroid metabolism form a "Steroid Metabolism Group" the definition of which supports particular methods of data analysis and will support the elaboration of mathematical algorithms useful in the prediction of outcome in various forms of cancer. The precise definition of the genes in the "Steroid Metabolism Group may vary depending on the identity of the steroid relevant in a particular cancer but will be defined to include a) genes, the expression products of which are known or suspected to be involved in synthesis and degradation of the particular steroid and clearance of intermediates, and b) genes that are co-expressed with such genes.

B.5 Clinical Application of Data

The methods of this invention could be performed as a self-contained test for cancer. Individual markers of the invention identified by univariate analysis or sets of markers of the inventions (e.g. identified by multivariate analysis) are useful predictors of clinical outcome. Alternatively the markers can be applied as predictive elements of a test that could include other predictive indicators including a) other genes and/or gene groups, or b) other clinical indicators such as tumor stage and grade).

B.6 Kits of the Invention

The methods of this invention, when practiced for commercial diagnostic purposes would typically be performed in a CLIA-approved clinical diagnostic laboratory. The materials for use in the methods of the present invention are suited for preparation of kits produced in accordance with well known procedures. The invention thus provides kits or components thereof, such kits comprising agents, which may include gene-specific or gene-selective probes and/or primers, for quantitating the expression of the disclosed genes for predicting prognostic outcome or response to treatment. Such kits may optionally contain reagents for the extraction of RNA from tumor samples, in particular fixed paraffin-embedded tissue samples and/or reagents for RNA amplification. In addition, the kits may optionally comprise the reagent(s) with an identifying description or label or instructions relating to their use in the methods of the present invention. The kits may comprise containers (including microtiter plates suitable for use in an automated implementation of the method), each with one or more of the various reagents (typically in concentrated form) utilized in the methods, including, for example; pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention (e.g., appropriate length poly (T) or random primers linked to a promoter reactive with the RNA polymerase). Mathematical algorithms used to estimate or quantify prognostic or predictive information are also properly potential components of kits.

The methods provided by the present invention may also be automated in whole or in part.

All aspects of the present invention may also be practiced such that a limited number of additional genes that are co-expressed with the disclosed genes, for example as evidenced by high Pearson correlation coefficients, are included in a prognostic or predictive test in addition to and/or in place of disclosed genes.

Having described the invention, the same will be more readily understood through reference to the following Example, which is provided by way of illustration, and is not intended to limit the invention in any way.

EXAMPLES

Example 1

Multiple GSTM1 Gene Family Members as Recurrance Risk Markers

Breast Tumor FPE Specimens. Archival breast tumor FPE blocks, from patients diagnosed between 1990 and 1997, were provided by Providence St. Joseph Medical Center, Burbank Calif. and were a subset of specimens examined in a previously reported observational study [Esteban, J. et al. *Prog. Proc Am Soc. Clin. Oncol.* 22, 850 abstract (2003)]. The tumor tissue specimens all came from female breast cancer patients with primary disease (90% stage I or II) and relatively little nodal involvement (80% node negative). The protocol for use of these specimens was approved by the IRB of that medical center.

Human genomic DNA samples. Genomic DNA was supplied by Dr. Maureen Cronin. The samples were collected with informed consent for genotyping under an IRB approved protocol.

RNA extraction and preparation. RNA was extracted from three 10 μm FPE sections per patient specimen according to Cronin et al. [*Am. J. Pathol.* 164, 35-42 (2004)].

RNA amplification. The FPE RNA used in this study was amplified prior to RT-PCR assay in order to preserve the RNA for later studies. Fifty ng of each FPE RNA sample was amplified using the SenseAmp kit from Genisphere (Hatfield, Pa.). The amplified RNA products were purified using the mirVana miRNA isolation kit from Ambion.

TaqMan primer/probe design: Exon-based assays: mRNA reference sequence accession numbers for genes of interest were identified and used to access the sequences through the NCBI Entrez Nucleotide database. Intron-based assays: Intron sequences were delineated by aligning appropriate mRNA reference sequences with their corresponding genes by using the DNA BLAT software [Kent, W. J., *Genome Res.* 12, 656-664(2002)]. Repetitive sequences within the introns were identified and masked using the Repeat Masker program (Institute for Systems Biology). Primers and probes were designed using Primer Express 2.0 (Applied Biosystems, Foster City, Calif.), or Primer 3 [Rozen, R. & Skaletsky, H. J. In Krawetz, S, Misener, S (eds) *Bioinformatics Methods and Protocols:Methods in Molecular Biology*: Humana Press, Totowa, N.J., 365-386(2000)]. Standard chemistry oligonucleotides were supplied by Biosearch Technologies Inc. (Novato, Calif.), Integrated DNA Technologies (Coralville, Iowa), and Eurogentech (San Diego, Calif.); MGB probes were supplied by Applied Biosystems. Amplicon sizes were typically 60-85 bases in length. Fluorogenic probes were dual-labeled with 5'-FAM and 3'-BHQ-2.

Reverse Transcription and TaqMan gene expression profiling RT-PCR was carried out as previously described [Cronin et al., *Am. J. Pathol.* 164, 35-42 (2004)].

Normalization and data analysis. Reference gene-based normalization was used to correct for differences in RNA quality and total quantity of RNA assayed. A set of five reference genes were selected from a series of candidates based on their low variance in expression across all the FPE breast cancer tissues and absence of a relationship (p>0.25) with disease free survival. A reference CT for each tested tissue was defined as the average measured CT of the five reference genes. The normalized mRNA level of a test gene within a tissue specimen was defined by the difference between the average CT of the test gene (from triplicate measurements) minus the reference CT.

Statistical analysis. Least squares linear regression was used to model the relationship between the levels of pairs of assays. Pearson's correlation coefficient was used to summarize the strength of the linear relationship. Cox Proportional Hazards regression was used to model the relationship between gene expression levels and disease-free survival, which was defined as the time from surgical removal of the breast tumor until the recurrence of breast cancer or death from breast cancer or an unknown cause.

The GSTM (GSTµ) gene family consists of five different closely related isotypes named GSTM1-GSTM5. We have reported four independent clinical studies in which GSTM gene expression strongly correlates with good outcome in primary breast cancer, based on measurements made using an RT-PCR probe-primer set (designated GSTM1.1) that was designed to recognize GSTM1 [8, Esteban, J. et al: Tumor gene expression and prognosis in breast cancer:multigene RT-PCR assay of paraffin-embedded tissue. *Prog. Proc Am Soc. Clin. Oncol.* 22, 850 abstract (2003), Cobleigh, M. A. et al. Tumor gene expression predicts distant disease-free survival (DDFS) in breast cancer patients with 10 or more positive nodes: high throughput RT-PCR assay of paraffin-embedded tumor tissues. *Prog. Proc Am Soc. Clin. Oncol.* 22, 850 abstract (2003), Paik, S. et al. Multi-gene RT-PCR assay for predicting recurrence in node negative breast cancer patients-NSABP studies B-20 and B-14. *Breast Cancer Res. Treat.* 82:A16.abstract (2003)].

GSTM expression was examined by qRT-PCR in FPET primary breast cancer tissues. GSTM1 was detected with the GSTM1.1 assay, which recognizes several GSTM isotypes. The estimate of relative risk in studies 1-4 was based on the hazard ratio (HR) from analysis of the time to breast cancer recurrence using univariate Cox proportional hazards regression. The estimate of relative risk in study 5 was based on the odds ratio (OR) from analysis of breast cancer death in a matched ease-control study using conditional logistic regression.

Study 1, Esteban et al., *Prog. Proc Am Soc. Clin, Oncol.* 22:850 abstract, 2003; Study 2, Cobleigh et al., *Clin Cancer Res* 11:8623-31,2005; Study 3, Paik et al., *Breast Cancer Res. Treat.* 82:A16 abstract, 2003; Study 4, Paik et al, *N. Engl J Med* 351:2817-26, 2004; Study 5, Habel et. al, *Breast Cancer Res. Treat.* 88:3019 abstract, 2004. The results are shown in Table 1.* Patients in studies 3-5 were tamoxifen treated, LN−,ER+. GSTM expression was a consistent predictor of favorable outcome in five independent breast cancer recurrence studies.

TABLE 1

| Study | Relative Risk | P-Value | Rank (among tested genes) | Total no. of genes tested |
|---|---|---|---|---|
| 1 Providence | 0.71 | 0.0014 | 6 | 192 |
| 2 Rush | 0.80 | 0.0200 | 5 | 192 |
| 3 NSABP 20* | 0.68 | 0.0005 | 7 | 192 |
| 4 NSABP 14* | 0.73 | <0.0001 | 5 | 21 (OncotypeDX) |
| 5 Kaiser* | 0.72 | <0.0010 | ≤6 | 21 (OncotypeDX) |

Sequence alignments of GSTM1 and GSTM2 amplicons with corresponding regions of other GSTM family members (FIG. 1). Sequences were aligned by Clustal W (family member denoted in left column). Arrows mark forward (left) and reverse RT-PCR primer (right) regions. Sequences beneath horizontal line indicates probe region. Gray boxes highlight mismatches with primers/probes in the first column. The vertical line in GSTM1.1 indicates a spliced exon-exon junction. The vertical line in GSTM2int4.2 indicates an unspliced intron-exon junction. In fact, alignment of the targeted GSTM1 amplicon probe-primer set with homologous regions in GSTM2, GSTM4 and GSTM5 indicates only 1, 3 and 3 base mismatches, respectively, indicating that GSTM1.1 may also amplify those sequences (FIG. 1).

Consistent with the fact that 50% of the U.S. population is homozygous GSTM1-null, the GSTM1 intron-based assay displays a biphasic expression pattern within 125 breast cancer specimens. FIG. 2 shows the number of patients (Y-axis) and corresponding Ct values (x-axis) were plotted for GSTM1.1, GSTM1int5.2 and GSTM2int4.2 assays. Expression levels were determined by TaqMan RT-PCR. "int" indicates that the assay was derived from intron sequence.

tially regulated. GSTM4.1 vs. GSTM5.2 and GSTM4.1 vs.GSTM1int5.2 show the lowest levels of coordinated expression (R=0.15-0.22) which was not unexpected since they are detecting transcripts from different genes. GSTM2int4.2 and GSTM3.6, the two genes that both contribute to positive prognosis in the multivariate analysis, show a modest positive correlation (0.42).

In summary, the positive effects of the GSTM family members are most likely due to a combination of protein function and co-expression. (Table 2).

TABLE 2

| Pearson (R) correlation | GSTM1 int 5.2 | GSTM1 int 3.1 | GSTM1.1 | GSTM2 int 4.2 | GSTM3.6 | GSTM4.1 | GSTM5.2 |
|---|---|---|---|---|---|---|---|
| GSTM1 int 5.2 | 1.00 | | | | | | |
| GSTM1 int 3.1 | 0.91 | 1.00 | | | | | |
| GSTM1.1 | 0.52 | 0.49 | 1.00 | | | | |
| GSTM2 int 4.2 | 0.26 | 0.25 | 0.57 | 1.00 | | | |
| GSTM3.6 | 0.26 | 0.23 | 0.46 | 0.37 | 1.00 | | |
| GSTM4.1 | 0.15 | 0.18 | 0.51 | 0.34 | 0.44 | 1.00 | |
| GSTM5.2 | N/A | N/A | 0.19 | 0.23 | 0.23 | 0.15 | 1.00 |
| GSTM5.1 | 0.29 | 0.28 | 0.40 | 0.28 | 0.27 | 0.22 | N/A |

Figure 3:
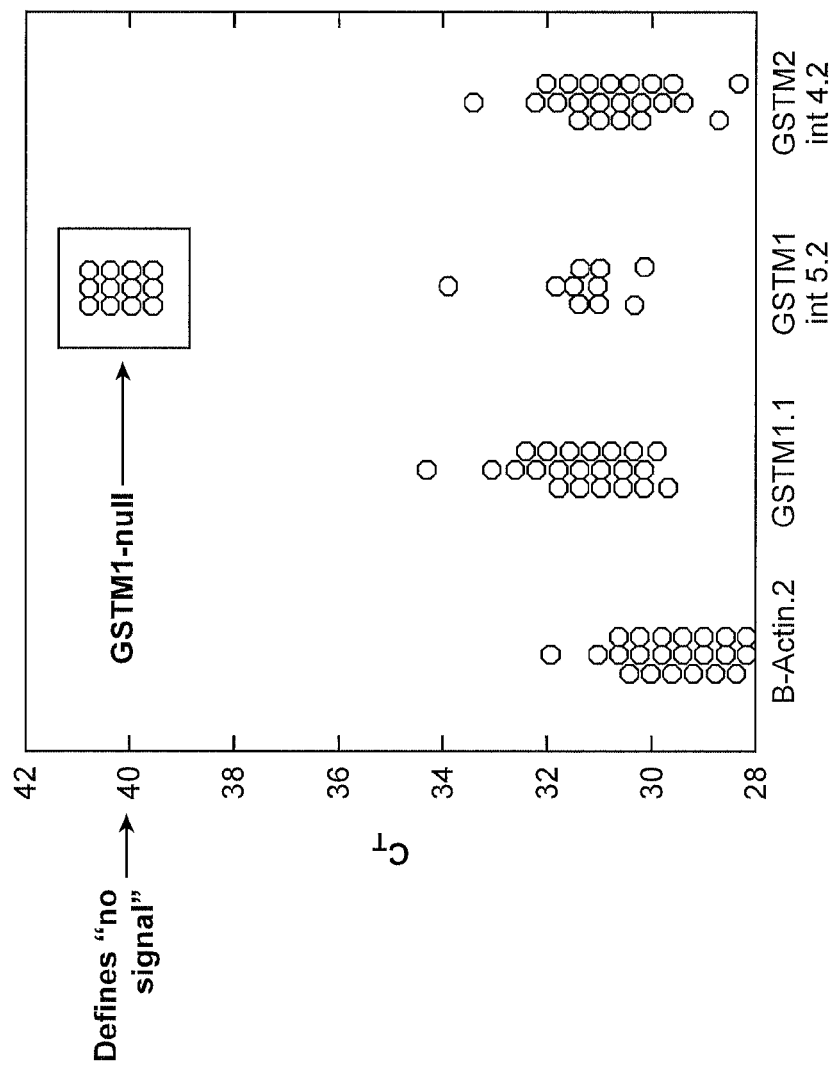
FIG. 3 shows the distribution of RT-PCR signals as CT values for 22 human subjects for the different GSTM amplicons.
Figure 4:
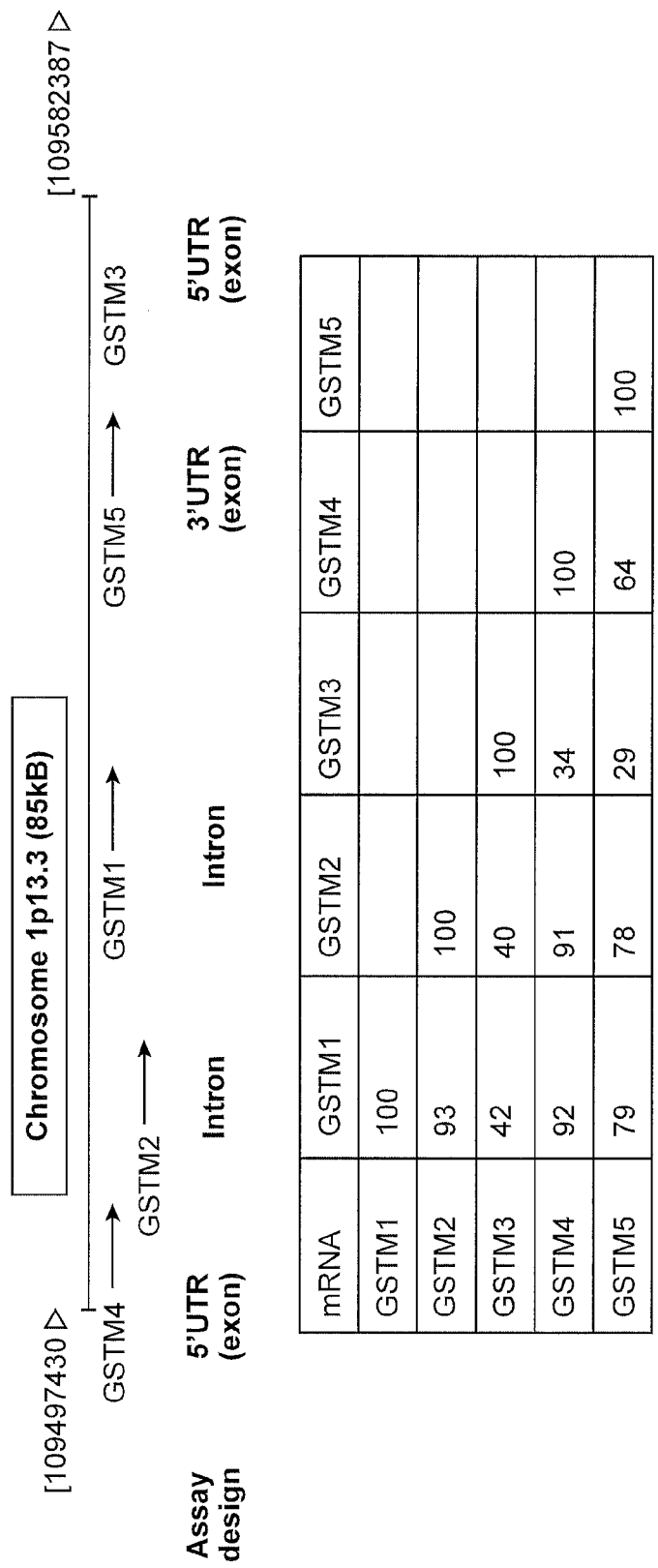
FIG. 4 shows the similarity and chromosome location of the GSTM genes.
Figure 5:
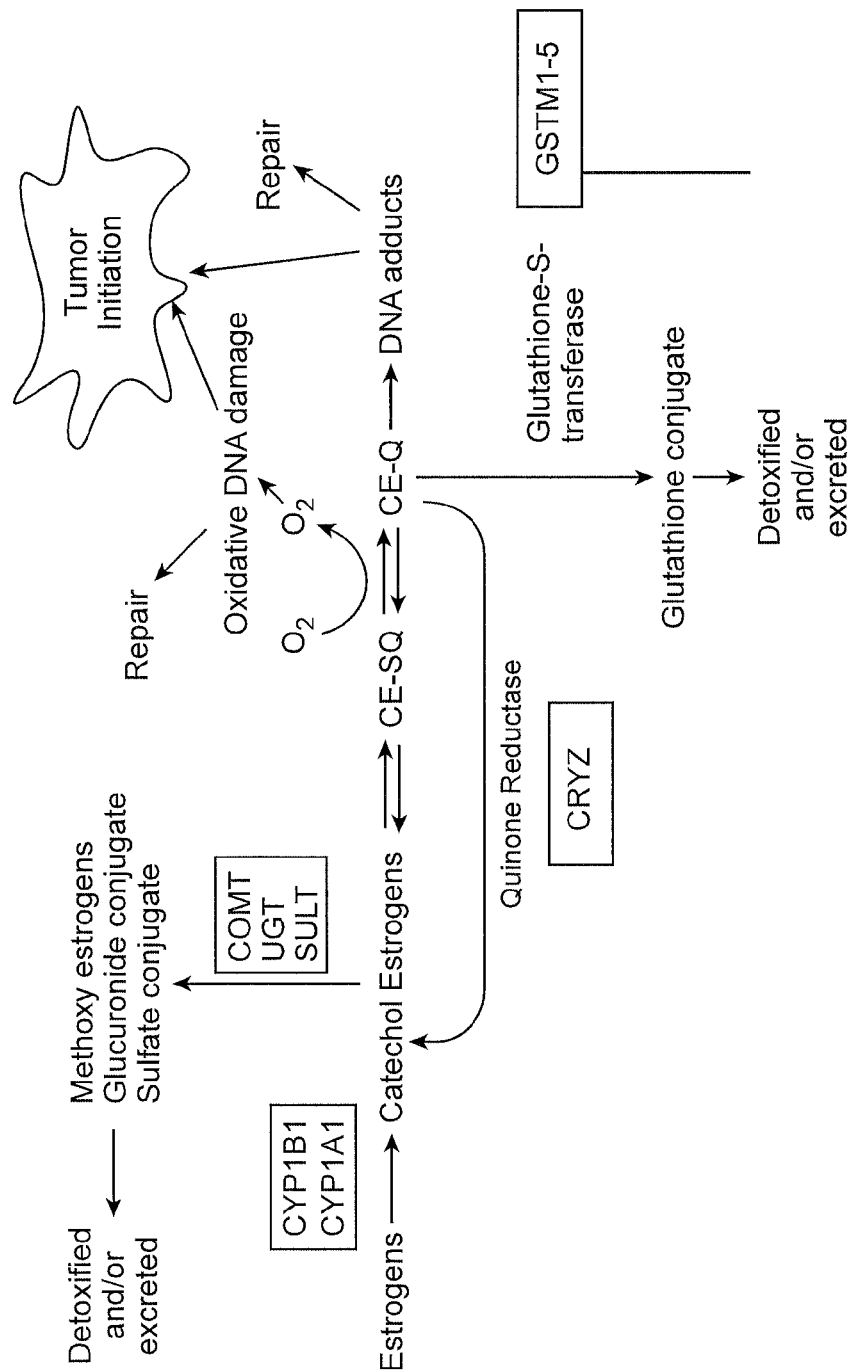
FIG. 5 shows the cellular pathways which are the possible basis for the correlation of GSTM expression with good outcome.
Figure 6:
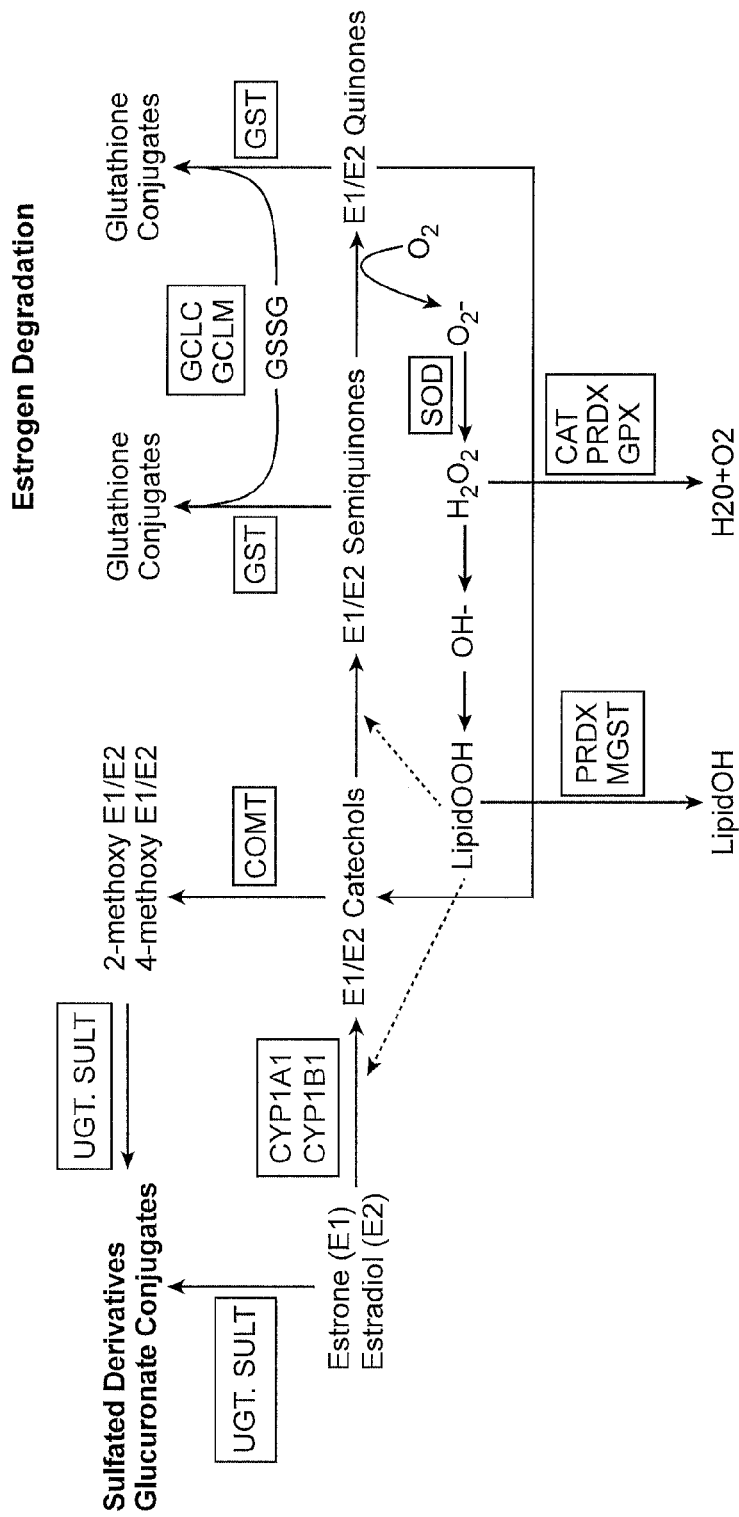
FIG. 6 shows specific pathways for the degradation, modification and clearance of key estrogens, estrone and estradiol.

It is noteworthy that a GSTM1.1 signal was detected in all specimens ($C_T$<40). This result is strong evidence that GSTM1.1 is not specific for GSTM1, because it is well-established that approximately 50% of the Caucasian and Asian populations are homozygous null for the GSTM1 gene. FIG. 2 shows that in the case of GSTM1int5.2, RT-PCR signals distribute in a bimodal pattern, with no signal detected in ~50% of the specimens, consistent with specificity for GSTM1. GSTM1int3.1 showed a similar bimodal pattern as GSTM1int5. Furthermore, as shown in FIG. 3, genotyping of 22 independent human genomic DNA samples using GSTM1int5.2 identified ~50% as GSTM1 null, ($C_T$=40). $C_T$ values were ~31-32 for the remaining samples. Again, GSTM1.1 failed to discriminate between the two GSTM1 genotypes, yielding $C_T$~31-32 in all cases.

We also explored the expression of another GSTM isotype, GSTM2, using an intron-based design, designated GSTM2int4.2. This 73 base amplicon differs from the other GSTM isotypes by 14 or more bases within the corresponding primer/probe regions (FIG. 2). Expression of this sequence in the 125 patient specimens distributes across 6 $C_T$ units, from 34-40 (FIG. 2). Genotyping with GSTM2int4.2 gave uniform positive signals for all 22 tested DNA specimens (FIG. 3) indicating that GSTM2 is not deleted, Pearson (R) correlation between GSTM family members. Table 2 shows the Pearson (r) correlation for the various GStM gene family members as determined by various probe-primer sets. Bold font denotes R values between assay sets that we found to be specific for the designated genes. "int" indicates that the assay was derived from intron sequence. In general, the GSTM family members show positive correlations of expression. However, there is a wide range of correlations that vary not only between genes but also between probe-primer sets within the same gene. Among the probe-primer sets thought to be gene specific (bold font), correlations range from 0.15 to 0.91. GSTM1int3.1 and GSTM1int5.2 showed the highest degree of co-expression (R=0.91). Interestingly, GSTM3.5 and GSTM3.6 show a more modest correlation (R=0.68) suggesting perhaps that they monitor alternate GSTM3 transcripts that are differen- GSTM1-5 expression predict favorable outcome in the 125 breast cancer specimen study. Multivariate analysis suggests that GSTM2 and GSTM3 carry independent biomarker information. Univariate and multivariate Cox PH regression analysis. Assays are ordered by p-value, with p-values ≤0.05 considered significant. Data in bold are assays that are specific. "int" indicates that the assay was derived from intron sequence. (Tables 3 and 4).

The tables indicate that all 5 GSTM genes are indicators of positive prognosis. The order of predictive strength from strongest to weakest is: GSTM3>GSTM2>GSTM4>GSTM5>GSTM1.

TABLE 3

| Univariate Analysis | Hazard Ratio | HR 95% LCL | HR 95% UCL | P-Value |
|---|---|---|---|---|
| GSTM3.6 | 0.57 | 0.42 | 0.78 | 0.0003 |
| GSTM2 int 4.2 | 0.64 | 0.49 | 0.83 | 0.0003 |
| GSTM1.1 | 0.71 | 0.58 | 0.86 | 0.0009 |
| GSTM4.1 | 0.68 | 0.53 | 0.87 | 0.0044 |
| GSTM1 int 5.2 | 0.79 | 0.64 | 0.96 | 0.0128 |
| GSTM5.2 | 0.77 | 0.58 | 1.02 | 0.0493 |
| GSTM1 int 3.1 | 0.84 | 0.70 | 1.02 | 0.0632 |

A multivariate stepwise Cox PH analysis indicated that GSTM3 and GSTM2 contributed independently to the positive prognosis (Table 4). Because there was an independent contribution to survival by both GSTM2 and GSTM3, it would suggest that each gene (product) has a biological effect.

TABLE 4

| Multivariate Analysis | Hazard Ratio | HR 95% LCL | HR 95% UCL | P-Value |
|---|---|---|---|---|
| GSTM3.6 | 0.65 | 0.47 | 0.90 | 0.0105 |
| GSTM2 int 4.2 | 0.74 | 0.58 | 0.95 | 0.0185 |

The results indicate that all five GSTM genes are correlated with the likelihood of breast cancer recurrence and suggest that certain GSTM family members contribute independent prognostic information.

Example 2

A Study Of The Prognostic Value Of GSTM Family Members And Estrogen Metabolizing Genes in Invasive Breast Cancer The primary objective of this study was to determine the relationship between the expression of genes involved in estrogen metabolism (including members of the GST gene family) and clinical outcome, in particular distant recurrence-free survival (DRFS), in breast cancer carcinoma.

Study Design

Inclusion Criteria

Samples were initially obtained from patients meeting the following criteria.

Surgery performed with diagnosis of invasive ductal carcinoma of the breast, ductal carcinoma in situ (DCIS), lobular carcinoma of the breast, or lobular carcinoma in situ (LCIS).

Histopathologic assessment indicating adequate amounts of tumor tissue and homogeneous pathology for inclusion in this research study.

For each patient sample included in the study, the expression level of each of 82 amplicons (shown in Table 5) was quantitatively assessed using qRT-PCR and the correlation between gene expression and distant recurrence-free survival (DRFS) for each of the test genes was evaluated. Distant recurrence-free survival is the time from surgery until the first diagnosis of distant recurrence. Contralateral disease, other second primary cancers, and deaths prior to distant recurrence will be considered censoring events. For the primary analysis, ipsilateral breast recurrence, local chest wall recurrence and regional recurrence is ignored, i.e., not considered either as an event or a censoring event.

For this study, one hundred twenty five (125) tumor samples were chosen from the patients. All recurring patients were included in the study, as well as a randomly selected subset of patients who were censored (J. Esteban et al., ASCO Meeting Proceedings 22:850 (2003) (Abstract 3416)).

Gene Panel

A panel of genes potentially involved in metabolism or clearance of estrogen or in other aspects of cancer pathophysiology was compiled based on published literature. Analysis of 82 genes selected from this panel or potentially useful as reference genes and listed in Table 5 was carried out using quantitative RT-PCR. For certain of the genes, multiple probe primer sets targeted to distinct gene sequences were utilized. Gene names and primer and probe sequences used to quantify transcript expression are listed in Table 6.

TABLE 5

| Official Symbol | NCBI Sequence ID | Sequence Version | Gene ID |
|---|---|---|---|
| AKR1C1 | BC040210 | BC040210.1 | 1645 |
| AKR1C2 | NM_001354 | NM_001354.4 | 1646 |
| AKR1C3 | NM_003739 | NM_003739.4 | 8644 |
| ATP5A1 | NM_004046 | NM_004046.4 | 498 |
| ACTB | NM_001101 | NM_001101.2 | 60 |
| BCL2 | NM_000633 | NM_000633.1 | 596 |
| CAT | NM_001752 | NM_001752.1 | 847 |
| CD68 | NM_001251 | NM_001251.1 | 968 |
| CDH1 | NM_004360 | NM_004360.2 | 999 |
| SCUBE2 | NM_020974 | NM_020974.1 | 57758 |
| COMT | NM_000754 | NM_000754.2 | 1312 |
| COX8A | NM_004074 | NM_004074.2 | 1351 |
| CRYZ | NM_001889 | NM_001889.2 | 1429 |
| CTSL2 | NM_001333 | NM_001333.2 | 1515 |
| PPIH | NM_006347 | NM_006347.3 | 10465 |
| CYP17A1 | NM_000102 | NM_000102.2 | 1586 |
| CYP19A1 | NM_000103 | NM_000103.2 | 1588 |
| CYP1A1 | NM_000499 | NM_000499.2 | 1543 |
| CYP1B1 | NM_000104 | NM_000104.2 | 1545 |
| CYP4Z1 | NM_178134 | NM_178134.2 | 199974 |
| EPHX1 | NM_000120 | NM_000120.2 | 2052 |
| ESR1 | NM_000125 | NM_000125.1 | 2099 |
| FOXM1 | NM_021953 | NM_021953.2 | 2305 |
| GAPD | NM_002046 | NM_002046.2 | 2597 |
| GCLC | NM_001498 | NM_001498.2 | 2729 |
| GCLM | NM_002061 | NM_002061.2 | 2730 |
| GPX1 | NM_000581 | NM_000581.2 | 2876 |
| GPX2 | NM_002083 | NM_002083.2 | 2877 |
| GSTM1 | NM_000561 | NM_000561.2 | 2944 |
| GSTM2 | NM_000848 | NM_000848.2 | 2946 |
| GSTM3 | NM_000849 | NM_000849.3 | 2947 |
| GSTM4 | NM_000850 | NM_000850.3 | 2948 |
| GSTM5 | NM_000851 | NM_000851.2 | 2949 |
| GSTP1 | NM_000852 | NM_000852.2 | 2950 |
| GSTT1 | NM_000853 | NM_000853.1 | 2952 |
| GUSB | NM_000181 | NM_000181.1 | 2990 |
| HOXB13 | NM_006361 | NM_006361.2 | 10481 |
| HSD17B1 | NM_000413 | NM_000413.1 | 3292 |
| HSD17B2 | NM_002153 | NM_002153.1 | 3294 |
| HSD17B4 | NM_000414 | NM_000414.1 | 3295 |
| IL17RB | NM_018725 | NM_018725.2 | 55540 |
| IMMT | NM_006839 | NM_006839.1 | 10989 |
| MKI67 | NM_002417 | NM_002417.2 | 4288 |
| LIPA | NM_000235 | NM_000235.2 | 3988 |
| MDH2 | NM_005918 | NM_005918.2 | 4191 |
| MGST1 | NM_020300 | NM_020300.3 | 4257 |
| MGST3 | NM_004528 | NM_004528.2 | 4259 |
| MPV17 | NM_002437 | NM_002437.3 | 4358 |
| MVP | NM_017458 | NM_017458.2 | 9961 |
| NAT1 | NM_000662 | NM_000662.4 | 9 |
| NAT2 | NM_000015 | NM_000015.1 | 10 |
| NCOA2 | NM_006540 | NM_006540.1 | 10499 |
| NDUFA7 | NM_005001 | NM_005001.1 | 4701 |
| NQO1 | NM_000903 | NM_000903.1 | 1728 |
| NQO2 | NM_000904 | NM_000904.1 | 4835 |
| TP53 | NM_000546 | NM_000546.2 | 7157 |
| SERPINE1 | NM_000602 | NM_000602.1 | 5054 |
| PGR | NM_000926 | NM_000926.2 | 5241 |
| PRAME | NM_006115 | NM_006115.3 | 23532 |
| PRDX2 | NM_005809 | NM_005809.4 | 7001 |
| PRDX3 | NM_006793 | NM_006793.2 | 10935 |
| PRDX4 | NM_006406 | NM_006406.1 | 10549 |
| PRDX6 | NM_004905 | NM_004905.2 | 9588 |
| RPLP0 | NM_001002 | NM_001002.3 | 6175 |
| SC5DL | NM_006918 | NM_006918.2 | 6309 |
| SOD1 | NM_000454 | NM_000454.4 | 6647 |
| SOD2 | NM_000636 | NM_000636.1 | 6648 |
| SOD3 | NM_003102 | NM_003102.1 | 6649 |
| SRD5A2 | NM_000348 | NM_000348.2 | 6716 |
| STK6 | NM_003600 | NM_003600.2 | 6790 |
| SULT1E1 | NM_005420 | NM_005420.2 | 6783 |
| SULT4A1 | NM_014351 | NM_014351.2 | 25830 |
| BIRC5 | NM_001168 | NM_001168.2 | 332 |
| TBP | NM_003194 | NM_003194.2 | 6908 |
| TFRC | NM_003234 | NM_003234.1 | 7037 |
| TST | NM_003312 | NM_003312.4 | 7263 |
| UGT1A3 | NM_019093 | NM_019093.2 | 54659 |
| UGT2B7 | NM_001074 | NM_001074.1 | 7364 |
| PLAU | NM_002658 | NM_002658.2 | 5328 |
| VDAC1 | NM_003374 | NM_003374.1 | 7416 |
| VDAC2 | NM_003375 | NM_003375.2 | 7417 |
| XPC | NM_004628 | NM_004628.3 | 7508 |

TABLE 6

| Probe Name | Accession Number | Reagent | Oligo Sequence | Seq id No: | Oligo Length |
|---|---|---|---|---|---|
| AKR1C1.1 | BC040210 | Forward | GTGTGTGAAGCTGAATGATGG | 1 | 21 |
| | BC040210 | Reverse | CTCTGCAGGCGCATAGGT | 2 | 18 |
| | BC040210 | Probe | CCAAATCCCAGGACAGGCATGAAG | 3 | 24 |
| AKR1C2.1 | NM_001354 | Forward | TGCCAGCTCATTGCTCTTAT | 4 | 20 |
| | NM_001354 | Reverse | TCTGTCACTGGCCTGGTTAG | 5 | 20 |
| | NM_001354 | Probe | CAAATGTTTCTTCCTCCCTCACAGGC | 6 | 26 |
| AKR1C3.1 | NM_003739 | Forward | GCTTTGCCTGATGTCTACCAGAA | 7 | 23 |
| | NM_003739 | Reverse | GTCCAGTCACCGGCATAGAGA | 8 | 21 |
| | NM_003739 | Probe | TGCGTCACCATCCACACACAGGG | 9 | 23 |
| ATP5A1.1 | NM_004046 | Forward | GATGCTGCCACTCAACAACT | 10 | 20 |
| | NM_004046 | Reverse | TGTCCTTGCTTCAGCAACTC | 11 | 20 |
| | NM_004046 | Probe | AGTTAGACGCACGCCACGACTCAA | 12 | 24 |
| B-actin.2 | NM_001101 | Forward | CAGCAGATGTGGATCAGCAAG | 13 | 21 |
| | NM_001101 | Reverse | GCATTTGCGGTGGACGAT | 14 | 18 |
| | NM_001101 | Probe | AGGAGTATGACGAGTCCGGCCCC | 15 | 23 |
| Bcl2.1 | NM_000633 | Probe | TGTACGGCCCCAGCATGCGG | 16 | 20 |
| | NM_000633 | Forward | CTGGGATGCCTTTGTGGAA | 17 | 19 |
| | NM_000633 | Reverse | CAGAGACAGCCAGGAGAAATCA | 18 | 22 |
| Bcl2.2 | NM_000633 | Forward | CAGATGGACCTAGTACCCACTGAGA | 19 | 25 |
| | NM_000633 | Reverse | CCTATGATTTAAGGGCATTTTTCC | 20 | 24 |
| | NM_000633 | Probe | TTCCACGCCGAAGGACAGCGAT | 21 | 22 |
| Bcl2 intron 1 50 kb.1 | NM_000633int1-50 kb | Forward | GCATCATTTGTTGGGTATGGAGTT | 22 | 24 |
| | NM_000633int1-50 kb | Reverse | TCTATGGAGGCCAATATTTGATTCT | 23 | 25 |
| | NM_000633int1-50 kb | Probe | AGCCAGTGTCCCTCAACCCAACTTCTG | 24 | 27 |
| Bcl2 intron 1 50 kb.2 | NM_000633int1-50 kb | Forward | GGGCAGTGGCCTGATGAA | 25 | 18 |
| | NM_000633int1-50 kb | Reverse | ATGGCAAAACTGTGTCTTTCCTTAT | 26 | 25 |
| | NM_000633int1-50 kb | Probe | CTTTTCTTCATTTTGCT | 27 | 18 |
| Bcl2 intron 1 100 kb.1 | NM_000633int1-100 kb | Forward | GTCACTTTTATCTCACAGCATCACAA | 28 | 26 |
| | NM_000633int1-100 kb | Reverse | GCATTGGATCTTGGTGTCTTGA | 29 | 22 |
| | NM_000633int1-100 kb | Probe | AGGAACATCTGACAGCACTTGCCAGGTT | 30 | 28 |
| Bcl2 intron 1 150 kb.2 | NM_000633int1-150 kb | Forward | GGAGAAGTAGCCAGCCCATTTAA | 31 | 23 |
| | NM_000633int1-150 kb | Reverse | TGTCCCTGGCGCGTTTAG | 32 | 18 |
| | NM_000633int1-150 kb | Probe | ATGTCAGCAAAGATTCCAGT | 33 | 20 |

TABLE 6-continued

| Probe Name | Accession Number | Reagent | Oligo Sequence | Seq id No: | Oligo Length |
|---|---|---|---|---|---|
| Bcl2 intron1 3'.1 | NM_000633int1-3 | Forward | CTAGCCACCCCCAAGAGAAAC | 34 | 21 |
| | NM_000633int1-3 | Reverse | TGCCAACCTCTAAGGTCAAGGT | 35 | 22 |
| | NM_000633int1-3 | Probe | CCTGACAGCTCCCTTTCCCCAGGA | 36 | 24 |
| Bcl2-beta.1 | NM_000657 | Forward | TGGGTAGGTGCACTTGGTGAT | 37 | 21 |
| | NM_000657 | Reverse | ACTCCAACCCCCGCATCT | 38 | 18 |
| | NM_000657 | Probe | ACCTGTGGCCTCAGCCCAGACTCA | 39 | 24 |
| CAT.1 | NM_001752 | Forward | ATCCATTCGATCTCACCAAGGT | 40 | 22 |
| | NM_001752 | Reverse | TCCGGTTTAAGACCAGTTTACCA | 41 | 23 |
| | NM_001752 | Probe | TGGCCTCACAAGGACTACCCTCTCATCC | 42 | 28 |
| CD68.2 | NM_001251 | Forward | TGGTTCCCAGCCCTGTGT | 43 | 18 |
| | NM_001251 | Reverse | CTCCTCCACCCTGGGTTGT | 44 | 19 |
| | NM_001251 | Probe | CTCCAAGCCCAGATTCAGATTCGAGTCA | 45 | 28 |
| CDH1.3 | NM_004360 | Forward | TGAGTGTCCCCCGGTATCTTC | 46 | 21 |
| | NM_004360 | Reverse | CAGCCGCTTTCAGATTTTCAT | 47 | 21 |
| | NM_004360 | Probe | TGCCAATCCCGATGAAATTGGAAATTT | 48 | 27 |
| CEGP1.2 | NM_020974 | Forward | TGACAATCAGCACACCTGCAT | 49 | 21 |
| | NM_020974 | Reverse | TGTGACTACAGCCGTGATCCTTA | 50 | 23 |
| | NM_020974 | Probe | CAGGCCCTCTTCCGAGCGGT | 51 | 20 |
| CEGP1.6 | NM_020974 | Forward | GCTGCATTTTATGTCCAAATGG | 52 | 22 |
| | NM_020974 | Reverse | TGGTCTTGGGCATGGTTCA | 53 | 19 |
| | NM_020974 | Probe | ATTTGTCCTTCCTCATTTTG | 54 | 20 |
| CEGP1 intron 4.1 | NM_020974 | Forward | TCCCCTTGCCTTTGGAGAA | 55 | 19 |
| | NM_020974 | Reverse | AAAGGCCTGGAGGCATCAA | 56 | 19 |
| | NM_020974 | Probe | CAGCCCAAATCCT | 57 | 13 |
| CEGP1 intron 5.1 | NM_020974 | Forward | CTTAATGGTGTTTAGCAGAGATGCA | 58 | 25 |
| | NM_020974 | Reverse | CCACTGTAGCATGCGAAGCA | 59 | 20 |
| | NM_020974 | Probe | CAAATGCACAGGAAAC | 60 | 16 |
| COMT.1 | NM_000754 | Forward | CCTTATCGGCTGGAACGAGTT | 61 | 21 |
| | NM_000754 | Reverse | CTCCTTGGTGTCACCCATGAG | 62 | 21 |
| | NM_000754 | Probe | CCTGCAGCCCATCCACAACCT | 63 | 21 |
| COX8.1 | NM_004074 | Forward | CGTTCTGTCCCTCACACTGTGA | 64 | 22 |
| | NM_004074 | Reverse | CAAATGCAGTAACATGACCAGGAT | 65 | 24 |
| | NM_004074 | Probe | TGACCAGCCCCACCGGCC | 66 | 18 |
| CRYZ.1 | NM_001889 | Forward | AAGTCCTGAAATTGCCATCA | 67 | 20 |
| | NM_001889 | Reverse | CACATGCATGGACCTTGATT | 68 | 20 |
| | NM_001889 | Probe | CCGATTCCAAAAGACCATCAGGTTCT | 69 | 26 |

TABLE 6-continued

| Probe Name | Accession Number | Reagent | Oligo Sequence | Seq id No: | Oligo Length |
|---|---|---|---|---|---|
| CTSL2.1 | NM_001333 | Forward | TGTCTCACTGAGCGAGCAGAA | 70 | 21 |
|  | NM_001333 | Reverse | ACCATTGCAGCCCTGATTG | 71 | 19 |
|  | NM_001333 | Probe | CTTGAGGACGCGAACAGTCCACCA | 72 | 24 |
| CTSL2.10 | NM_001333 | Forward | TCAGAGGCTTGTTTGCTGAG | 73 | 20 |
|  | NM_001333 | Reverse | AGGACGAGCGAAAGATTCAT | 74 | 20 |
|  | NM_001333 | Probe | CGACGGCTGCTGGTTTTGAAAC | 75 | 22 |
| CYP.1 | NM_006347 | Forward | TGGACTTCTAGTGATGAGAAAGATTGA | 76 | 27 |
|  | NM_006347 | Reverse | CACTGCGAGATCACCACAGGTA | 77 | 22 |
|  | NM_006347 | Probe | TTCCCACAGGCCCCAACAATAAGCC | 78 | 25 |
| CYP17A1.1 | NM_000102 | Forward | CCGGAGTGACTCTATCACCA | 79 | 20 |
|  | NM_000102 | Reverse | GCCAGCATTGCCATTATCT | 80 | 19 |
|  | NM_000102 | Probe | TGGACACACTGATGCAAGCCAAGA | 81 | 24 |
| CYP19A1.1 | NM_000103 | Forward | TCCTTATAGGTACTTTCAGCCATTTG | 82 | 26 |
|  | NM_000103 | Reverse | CACCATGGCGATGTACTTTCC | 83 | 21 |
|  | NM_000103 | Probe | CACAGCCACGGGGCCCAAA | 84 | 19 |
| CYP1A1.2 | NM_000499 | Forward | AATAATTTCGGGGAGGTGGT | 85 | 20 |
|  | NM_000499 | Reverse | GGTTGGGTAGGTAGCGAAGA | 86 | 20 |
|  | NM_000499 | Probe | TGGCTCTGGAAACCCAGCTGACTT | 87 | 24 |
| CYP1B1.3 | NM_000104 | Forward | CCAGCTTTGTGCCTGTCACTAT | 88 | 22 |
|  | NM_000104 | Reverse | GGGAATGTGGTAGCCCAAGA | 89 | 20 |
|  | NM_000104 | Probe | CTCATGCCACCACTGCCAACACCTC | 90 | 25 |
| CYP4Z1.1 | NM_178134 | Forward | GCCTTACACCACGATGTGCAT | 91 | 21 |
|  | NM_178134 | Reverse | GTCGAGTAACCGGGATATGTTTACTAC | 92 | 27 |
|  | NM_178134 | Probe | AAGGAATGCCTCCGCCTCTACGCAC | 93 | 25 |
| EPHX1.2 | NM_000120 | Forward | ACCGTAGGCTCTGCTCTGAA | 94 | 20 |
|  | NM_000120 | Reverse | TGGTCCAGGTGGAAAACTTC | 95 | 20 |
|  | NM_000120 | Probe | AGGCAGCCAGACCCACAGGA | 96 | 20 |
| EstR1.1 | NM_000125 | Forward | CGTGGTGCCCCTCTATGAC | 97 | 19 |
|  | NM_000125 | Reverse | GGCTAGTGGGCGCATGTAG | 98 | 19 |
|  | NM_000125 | Probe | CTGGAGATGCTGGACGCCC | 99 | 19 |
| FOXM1.1 | NM_021953 | Forward | CCACCCCGAGCAAATCTGT | 100 | 19 |
|  | NM_021953 | Reverse | AAATCCAGTCCCCCTACTTTGG | 101 | 22 |
|  | NM_021953 | Probe | CCTGAATCCTGGAGGCTCACGCC | 102 | 23 |
| FOXM1.3 | NM_021953 | Forward | TGCCCAGATGTGCGCTATTA | 103 | 20 |
|  | NM_021953 | Reverse | TCAATGCCAGTCTCCCTGGTA | 104 | 21 |
|  | NM_021953 | Probe | ATGTTTCTCTGATAATGTCC | 105 | 20 |
| FOXM1 intron 5.1 | NM_021953 | Forward | TGGACAGAGACAAGATGTGATGTG | 106 | 24 |
|  | NM_021953 | Reverse | GCTGGCACCTAGACAAAACATG | 107 | 22 |
|  | NM_021953 | Probe | CCATAGGGACCCTTC | 108 | 15 |

TABLE 6-continued

| Probe Name | Accession Number | Reagent | Oligo Sequence | Seq id No: | Oligo Length |
|---|---|---|---|---|---|
| FOXM1 intron 7.1 | NM_021953 | Forward | GGTGTCCTATTTTCCTCTGAAGAGA | 109 | 25 |
| | NM_021953 | Reverse | TGCAAGCTGAAGGTCCAACAT | 110 | 21 |
| | NM_021953 | Probe | TTCTGGCCAATTAAG | 111 | 15 |
| GAPDH.1 | NM_002046 | Forward | ATTCCACCCATGGCAAATTC | 112 | 20 |
| | NM_002046 | Reverse | GATGGGATTTCCATTGATGACA | 113 | 22 |
| | NM_002046 | Probe | CCGTTCTCAGCCTTGACGGTGC | 114 | 22 |
| GCLC.3 | NM_001498 | Forward | CTGTTGCAGGAAGGCATTGA | 115 | 20 |
| | NM_001498 | Reverse | GTCAGTGGGTCTCTAATAAAGAGATGAG | 116 | 28 |
| | NM_901498 | Probe | CATCTCCTGGCCCAGCATGTT | 117 | 21 |
| GCLM.2 | NM_002061 | Forward | TGTAGAATCAAACTCTTCATCATCAACTAG | 118 | 30 |
| | NM_002061 | Reverse | CACAGAATCCAGCTGTGCAACT | 119 | 22 |
| | NM_002061 | Probe | TGCAGTTGACATGGCCTGTTCAGTCC | 120 | 26 |
| GPX1.2 | NM_000581 | Forward | GCTTATGACCGACCCCAA | 121 | 18 |
| | NM_000581 | Reverse | AAAGTTCCAGGCAACATCGT | 122 | 20 |
| | NM_000581 | Probe | CTCATCACCTGGTCTCCGGTGTGT | 123 | 24 |
| GPX2.2 | NM_002083 | Forward | CACACAGATCTCCTACTCCATCCA | 124 | 24 |
| | NM_002083 | Reverse | GGTCCAGCAGTGTCTCCTGAA | 125 | 21 |
| | NM_002083 | Probe | CATGCTGCATCCTAAGGCTCCTCAGG | 126 | 26 |
| GSTM1.1 | NM_000561 | Reverse | GGCCCAGCTTGAATTTTTCA | 127 | 20 |
| | NM_000561 | Forward | AAGCTATGAGGAAAAGAAGTACACGAT | 128 | 27 |
| | NM_000561 | Probe | TCAGCCACTGGCTTCTGTCATAATCAGGAG | 129 | 30 |
| GSTM1 var2.1 | NM_146421 | Forward | CCATGGTTTGCAGGAAACAA | 130 | 20 |
| | NM_146421 | Reverse | AGAACACAGGTCTTGGGAGGAA | 131 | 22 |
| | NM_146421 | Probe | ATCTCTGCCTACATGAAGTCCAGCC | 132 | 25 |
| GSTM1 intron 1.1 | NM_000561 | Forward | AACGGGTACGTGCAGTGTAAACT | 133 | 23 |
| | NM_000561 | Reverse | GCAGGTCGCGTCAGAGATG | 134 | 19 |
| | NM_000561 | Probe | CCCTGACTTTGTCTGCACCAGGGAAG | 135 | 26 |
| GSTM1 intron 3.1 | NM_000561 | Forward | TCTGTGTCCACCTGCATTCG | 136 | 20 |
| | NM_000561 | Reverse | CTGCTCATGGCAGGACTGAA | 137 | 20 |
| | NM_000561 | Probe | TCATGTGACAGTATTCTTA | 138 | 19 |
| GSTM1 intron 5.1 | NM_000561int5 | Forward | CGACTCCAATGTCATGTCAACA | 139 | 22 |
| | NM_000561int5 | Reverse | ACCCTGGGATGCCTGGAT | 140 | 18 |
| | NM_000561int5 | Probe | AGAGGCAATTCCCACCAACCTTAGGACA | 141 | 28 |
| GSTM1 intron 5.2 | NM_000561int5 | Forward | GGCAATTCCCACCAACCTTA | 142 | 20 |
| | NM_000561int5 | Reverse | AAACTTTACCATACAGGAACTGAATTCT | 143 | 29 |
| | NM_000561int5 | Probe | ACACGATCCAGGCATCCCAGGG | 144 | 22 |

TABLE 6-continued

| Probe Name | Accession Number | Reagent | Oligo Sequence | Seq id No: | Oligo Length |
|---|---|---|---|---|---|
| GSTM1 intron 5.3 | NM_000561int5 | Forward | ATGGCACCCTCGAATTGC | 145 | 18 |
| | NM_000561int5 | Reverse | TGCATGTCAATGACAGCACTCA | 146 | 22 |
| | NM_000561int5 | Probe | TCTTCTCCTCAACAGTTTT | 147 | 19 |
| GSTM1 intron 7.2 | NM_000561int7 | Forward | GCCTCCCTGTGGAAAAGGA | 148 | 19 |
| | NM_000561int7 | Reverse | TCACACCAGGCCCTGTCA | 149 | 18 |
| | NM_000561int7 | Probe | TCCTTGACTGCACAAACAG | 150 | 19 |
| GSTM2 gene.1 | NM_000848gene | Forward | GCAGGAACGAGAGGAGGAGAT | 151 | 21 |
| | NM_000848gene | Reverse | CAGCTCGGGTCAGAGATGGA | 152 | 20 |
| | NM_000848gene | Probe | CTCCCCTTGTGCAGAGTCGTCACAAA | 153 | 26 |
| GSTM2 gene.4 | NM_000848gene | Forward | CTGGGCTGTGAGGCTGAGA | 154 | 19 |
| | NM_000848gene | Reverse | GCGAATCTGCTCCTTTTCTGA | 155 | 21 |
| | NM_000848gene | Probe | CCCGCCTACCCTCGTAAAGCAGATTCA | 156 | 27 |
| GSTM3.2 | NM_000849 | Forward | CAATGCCATCTTGCGCTACAT | 157 | 21 |
| | NM_000849 | Reverse | GTCCACTCGAATCTTTTCTTCTTCA | 158 | 25 |
| | NM_000849 | Probe | CTCGCAAGCACAACATGTGTGGTGAGA | 159 | 27 |
| GSTM3.5 | NM_000849 | Forward | CCAGAAGCCAAGGATCTCTCTAGT | 160 | 24 |
| | NM_000849 | Reverse | TATTCCTCCTGACATCACTGGGTAT | 161 | 25 |
| | NM_000849 | Probe | TGCCATTTGGGCCCTCTGACCAT | 162 | 23 |
| GSTM3.6 | NM_000849 | Forward | TCACAGTTTCCCTAGTCCTCGAA | 163 | 23 |
| | NM_000849 | Reverse | CGAATATCCCAGTACCCGAGAA | 164 | 22 |
| | NM_000849 | Probe | CCCGTCACCATGTCGTGCGAGTC | 165 | 23 |
| GSTM4.1 | NM_000850 | Forward | CGGACCTTGCTCCCTGAAC | 166 | 19 |
| | NM_000850 | Reverse | CGGAGCAGGTTGCTGGAT | 167 | 18 |
| | NM_000850 | Probe | AGTAAGATCCACCGCCACCTCCGAG | 168 | 25 |
| GSTM5.1 | NM_000851 | Forward | TCCCTGAGGCTCCCTTGACT | 169 | 20 |
| | NM_000851 | Reverse | GGCTGTGGACAACAGAAGACAA | 170 | 22 |
| | NM_000851 | Probe | CCACCCACAATTCGAGCACAGTCCT | 171 | 25 |
| GSTM5.2 | NM_000851 | Forward | GAAAGGTGCTCTGTGCCAAGT | 172 | 21 |
| | NM_000851 | Reverse | CCTAGCCCCTCTTTGAACCAT | 173 | 21 |
| | NM_000851 | Probe | ATTCGCGCTCCTGTAGGCCGTCTAGAA | 174 | 27 |
| GSTp.3 | NM_000852 | Forward | GAGACCCTGCTGTCCCAGAA | 175 | 20 |
| | NM_000852 | Reverse | GGTTGTAGTCAGCGAAGGAGATC | 176 | 23 |
| | NM_000852 | Probe | TCCCACAATGAAGGTCTTGCCTCCCT | 177 | 26 |
| GSTT1.3 | NM_000853 | Forward | CACCATCCCCACCCTGTCT | 178 | 19 |
| | NM_000853 | Reverse | GGCCTCAGTGTGCATCATTCT | 179 | 21 |
| | NM_000853 | Probe | CACAGCCGCCTGAAAGCCACAAT | 180 | 23 |
| GUS.1 | NM_000181 | Forward | CCCACTCAGTAGCCAAGTCA | 181 | 20 |
| | NM_000181 | Reverse | CACGCAGGTGGTATCAGTCT | 182 | 20 |
| | NM_000181 | Probe | TCAAGTAAACGGGCTGTTTTCCAAACA | 183 | 27 |

TABLE 6-continued

| Probe Name | Accession Number | Reagent | Oligo Sequence | Seq id No: | Oligo Length |
|---|---|---|---|---|---|
| HOXB13.1 | NM_006361 | Forward | CGTGCCTTATGGTTACTTTGG | 184 | 21 |
| | NM_006361 | Reverse | CACAGGGTTTCAGCGAGC | 185 | 18 |
| | NM_006361 | Probe | ACACTCGGCAGGAGTAGTACCCGC | 186 | 24 |
| HSD17B1.1 | NM_000413 | Forward | CTGGACCGCACGGACATC | 187 | 18 |
| | NM_000413 | Reverse | CGCCTCGCGAAAGACTTG | 188 | 18 |
| | NM_000413 | Probe | ACCGCTTCTACCAATACCTCGCCCA | 189 | 25 |
| HSD17B2.1 | NM_002153 | Forward | GCTTTCCAAGTGGGGAATTA | 190 | 20 |
| | NM_002153 | Reverse | TGCCTGCGATATTTGTTAGG | 191 | 20 |
| | NM_002153 | Probe | AGTTGCTTCCATCCAACCTGGAGG | 192 | 24 |
| HSD17B4.1 | NM_000414 | Forward | TTGTCCTTTGGCTTTGTCAC | 193 | 20 |
| | NM_000414 | Reverse | CAATCCATCCTGCTCCAAC | 194 | 19 |
| | NM_000414 | Probe | CAAACAAGCCACCATTCTCCTCACA | 195 | 25 |
| IL17RB.2 | NM_018725 | Forward | ACCCTCTGGTGGTAAATGGA | 196 | 20 |
| | NM_018725 | Reverse | GGCCCCAATGAAATAGACTG | 197 | 20 |
| | NM_018725 | Probe | TCGGCTTCCCTGTAGAGCTGAACA | 198 | 24 |
| IMMT.1 | NM_006839 | Forward | CTGCCTATGCCAGACTCAGA | 199 | 20 |
| | NM_006839 | Reverse | GCTTTTCTGGCTTCCTCTTC | 200 | 20 |
| | NM_006839 | Probe | CAACTGCATGGCTCTGAACAGCCT | 201 | 24 |
| Ki-67.2 | NM_002417 | Forward | CGGACTTTGGGTGCGACTT | 202 | 19 |
| | NM_002417 | Reverse | TTACAACTCTTCCACTGGGACGAT | 203 | 24 |
| | NM_002417 | Probe | CCACTTGTCGAACCACCGCTCGT | 204 | 23 |
| LIPA.1 | NM_000235 | Forward | CCAGTTGTCTTCCTGCAACA | 205 | 20 |
| | NM_000235 | Reverse | CTGTTGGCAAGGTTTGTGAC | 206 | 20 |
| | NM_000235 | Probe | CCAGTTACTAGAATCTGCCAGCAAGCCA | 207 | 28 |
| MDH2.1 | NM_005918 | Forward | CCAACACCTTTGTTGCAGAG | 208 | 20 |
| | NM_005918 | Reverse | CAATGACAGGGACGTTGACT | 209 | 20 |
| | NM_005918 | Probe | CGAGCTGGATCCAAACCCTTCAG | 210 | 23 |
| mGST1.2 | NM_020300 | Forward | ACGGATCTACCACACCATTGC | 211 | 21 |
| | NM_020300 | Reverse | TCCATATCCAACAAAAAAACTCAAAG | 212 | 26 |
| | NM_020300 | Probe | TTTGACACCCCTTCCCCAGCCA | 213 | 22 |
| MGST3.1 | NM_004528 | Forward | AGCTGTTGGAGGTGTTTACCA | 214 | 21 |
| | NM_004528 | Reverse | TCGTCCAACAATCCAGGC | 215 | 18 |
| | NM_004528 | Probe | AAGCCCAGGCCAGAAGCTATACGC | 216 | 24 |
| MMTV-like env.3 | AF346816 | Forward | CCATACGTGCTGCTACCTGT | 217 | 20 |
| | AF346816 | Reverse | CCTAAAGGTTTGAATGGCAGA | 218 | 21 |
| | AF346816 | Probe | TCATCAAACCATGGTTCATCACCAATATC | 219 | 29 |

TABLE 6-continued

| Probe Name | Accession Number | Reagent | Oligo Sequence | Seq id No: | Oligo Length |
|---|---|---|---|---|---|
| MPV17.1 | NM_002437 | Forward | CCAATGTGTTGCTGTTATCTGGAA | 220 | 24 |
| | NM_002437 | Reverse | ATGGAGTGAGGCAGGCTTAGAG | 221 | 22 |
| | NM_002437 | Probe | TCCTACCTGTCCTGGAAGGCACATCG | 222 | 26 |
| MVP.1 | NM_017458 | Forward | ACGAGAACGAGGGCATCTATGT | 223 | 22 |
| | NM_017458 | Reverse | GCATGTAGGTGCTTCCAATCAC | 224 | 22 |
| | NM_017458 | Probe | CGCACCTTTCCGGTCTTGACATCCT | 225 | 25 |
| NAT1.1 | NM_000662 | Forward | TGGTTTTGAGACCACGATGT | 226 | 20 |
| | NM_000662 | Reverse | TGAATCATGCCAGTGCTGTA | 227 | 20 |
| | NM_000662 | Probe | TGGAGTGCTGTAAACATACCCTCCCA | 228 | 26 |
| NAT2.1 | NM_000015 | Forward | TAACTGACATTCTTGAGCACCAGAT | 229 | 25 |
| | NM_000015 | Reverse | ATGGCTTGCCCACAATGC | 230 | 18 |
| | NM_000015 | Probe | CGGGCTGTTCCCTTTGAGAACCTTAACA | 231 | 28 |
| NCOA2.1 | NM_006540 | Forward | AGTGACCTCCGTGCCTACGT | 232 | 20 |
| | NM_006540 | Reverse | CTCCCCTCAGAGCAGGATCA | 233 | 20 |
| | NM_006540 | Probe | CCTCCATGGGTCCCGAGCAGG | 234 | 21 |
| NDUFA7.1 | NM_005001 | Forward | GCAGCTACGCTACCAGGAG | 235 | 19 |
| | NM_005001 | Reverse | GGAGAGCTTGTGGCTAGGAC | 236 | 20 |
| | NM_005001 | Probe | TCTCCAAGCGAACTCAGCCTCCTC | 237 | 24 |
| NQO1.1 | NM_000903 | Forward | CAGCAGACGCCCGAATTC | 238 | 18 |
| | NM_000903 | Reverse | TGGTGTCTCATCCCAAATATTCTC | 239 | 24 |
| | NM_000903 | Probe | AGGCGTTTCTTCCATCCTTCCAGGATT | 240 | 27 |
| NQO2.1 | NM_000904 | Forward | AGCGCTCCTTTCCGTAACC | 241 | 19 |
| | NM_000904 | Reverse | TCCATTGACTCCTGTCTTCGTGTA | 242 | 24 |
| | NM_000904 | Probe | ATCTCGGCCGTGCCTCCCG | 243 | 19 |
| P53.2 | NM_000546 | Forward | CTTTGAACCCTTGCTTGCAA | 244 | 20 |
| | NM_000546 | Reverse | CCCGGGACAAAGCAAATG | 245 | 18 |
| | NM_000546 | Probe | AAGTCCTGGGTGCTTCTGACGCACA | 246 | 25 |
| PAI1.3 | NM_000602 | Forward | CCGCAACGTGGTTTTCTCA | 247 | 19 |
| | NM_000602 | Reverse | TGCTGGGTTTCTCCTCCTGTT | 248 | 21 |
| | NM_000602 | Probe | CTCGGTGTTGGCCATGCTCCAG | 249 | 22 |
| PR.6 | NM_000926 | Forward | GCATCAGGCTGTCATTATGG | 250 | 20 |
| | NM_000926 | Reverse | AGTAGTTGTGCTGCCCTTCC | 251 | 20 |
| | NM_000926 | Probe | TGTCCTTACCTGTGGGAGCTGTAAGGTC | 252 | 28 |
| PR.12 | NM_000926 | Forward | GTTCCATCCCAAAGAACCTG | 253 | 20 |
| | NM_000926 | Reverse | GAAACTCTGGAGTTGGCATTT | 254 | 21 |
| | NM_000926 | Probe | CCACCCGTTATTCTGAATGCTACTCTCA | 255 | 28 |
| PRAME.3 | NM_006115 | Forward | TCTCCATATCTGCCTTGCAGAGT | 256 | 23 |
| | NM_006115 | Reverse | GCACGTGGGTCAGATTGCT | 257 | 19 |
| | NM_006115 | Probe | TCCTGCAGCACCTCATCGGGCT | 258 | 22 |

TABLE 6-continued

| Probe Name | Accession Number | Reagent | Oligo Sequence | Seq id No: | Oligo Length |
|---|---|---|---|---|---|
| PRAME.4 | NM_006115 | Forward | CCACTGCTCCCAGCTTACAAC | 259 | 21 |
|  | NM_006115 | Reverse | CTGCAAGGCAGATATGGAGATG | 260 | 22 |
|  | NM_006115 | Probe | AATTCCCGTAGAGCTTAA | 261 | 19 |
| PRAME intron 5.1 | NM_006115 | Forward | ATCAGGCACAGAGATAGAGGTGACT | 262 | 25 |
|  | NM_006115 | Reverse | TCTTTCAACTCGGGCTTCCTT | 263 | 21 |
|  | NM_006115 | Probe | CCCAGGCAGTGGCA | 264 | 14 |
| PRDX2.1 | NM_005809 | Forward | GGTGTCCTTCGCCAGATCAC | 265 | 20 |
|  | NM_005809 | Reverse | CAGCCGCAGAGCCTCATC | 266 | 18 |
|  | NM_005809 | Probe | TTAATGATTTGCCTGTGGGACGCTCC | 267 | 26 |
| PRDX3.1 | NM_006793 | Forward | TGACCCCAATGGAGTCATCA | 268 | 20 |
|  | NM_006793 | Reverse | CCAAGCGGAGGGTTTCTTC | 269 | 19 |
|  | NM_006793 | Probe | CATTTGAGCGTCAACGATCTCCCAGTG | 270 | 27 |
| PRDX4.1 | NM_006406 | Forward | TTACCCATTTGGCCTGGATTAA | 271 | 22 |
|  | NM_006406 | Reverse | CTGAAAGAAGTGGAATCCTTATTGG | 272 | 25 |
|  | NM_006406 | Probe | CCAAGTCCTCCTTGTCTTCGAGGGGT | 273 | 26 |
| PRDX6.1 | NM_004905 | Forward | CTGTGAGCCAGAGGATGTCA | 274 | 20 |
|  | NM_004905 | Reverse | TGTGATGACACCAGGATGTG | 275 | 20 |
|  | NM_004905 | Probe | CTGCCAATTGTGTTTTCCTGCAGC | 276 | 24 |
| RPLPO.2 | NM_001002 | Forward | CCATTCTATCATCAACGGGTACAA | 277 | 24 |
|  | NM_001002 | Reverse | TCAGCAAGTGGGAAGGTGTAATC | 278 | 23 |
|  | NM_001002 | Probe | TCTCCACAGACAAGGCCAGGACTCG | 279 | 25 |
| SC5DL.1 | NM_006918 | Forward | CGCCTACATAAACCTCACCA | 280 | 20 |
|  | NM_006918 | Reverse | CCATCAATAGGGTGAAAAGCA | 281 | 21 |
|  | NM_006918 | Probe | TGGAAGATTCCTACTCCATTTGCAAGTCA | 282 | 29 |
| SOD1.1 | NM_000454 | Forward | TGAAGAGAGGCATGTTGGAG | 283 | 20 |
|  | NM_006454 | Reverse | AATAGACACATCGGCCACAC | 284 | 20 |
|  | NM_000454 | Probe | TTTGTCAGCAGTCACATTGCCCAA | 285 | 24 |
| SOD2.1 | NM_000636 | Forward | GCTTGTCCAAATCAGGATCCA | 286 | 21 |
|  | NM_000636 | Reverse | AGCGTGCTCCCACACATCA | 287 | 19 |
|  | NM_000636 | Probe | AACAACAGGCCTTATTCCACTGCTGGG | 288 | 27 |
| SOD3.1 | NM_003102 | Forward | CCATAAGCCCTGAGACTCCC | 289 | 20 |
|  | NM_003102 | Reverse | TAGGAGGAACCTGAAGGCG | 290 | 19 |
|  | NM_003102 | Probe | TTGACCTGACGATCTTCCCCCTTC | 291 | 24 |
| SRD5A2.1 | NM_000348 | Forward | GTAGGTCTCCTGGCGTTCTG | 292 | 20 |
|  | NM_000348 | Reverse | TCCCTGGAAGGGTAGGAGTAA | 293 | 21 |
|  | NM_000348 | Probe | AGACACCACTCAGAATCCCCAGGC | 294 | 24 |

TABLE 6-continued

| Probe Name | Accession Number | Reagent | Oligo Sequence | Seq id No: | Oligo Length |
|---|---|---|---|---|---|
| STK15.2 | NM_003600 | Forward | CATCTTCCAGGAGGACCACT | 295 | 20 |
|  | NM_003600 | Reverse | TCCGACCTTCAATCATTTCA | 296 | 20 |
|  | NM_003600 | Probe | CTCTGTGGCACCCTGGACTACCTG | 297 | 24 |
| STK15.8 | NM_003600 | Forward | GCCCCCTGAAATGATTGAAG | 298 | 20 |
|  | NM_003600 | Reverse | TCCAAGGCTCCAGAGATCCA | 299 | 20 |
|  | NM_003600 | Probe | TTCTCATCATGCATCCGA | 300 | 18 |
| STK15 intron 2.1 | NM_003600 | Forward | CATTCACATTTATAAACCCACATGGA | 301 | 26 |
|  | NM_003600 | Reverse | AATCCAAAGTAAAGGCGGAAAGA | 302 | 23 |
|  | NM_003600 | Probe | TGGTCTTGTCGGGAAT | 303 | 16 |
| STK15 intron 4.1 | NM_003600 | Forward | GCGAGGAATGAACCCACAGA | 304 | 20 |
|  | NM_003600 | Reverse | GCATGAGAACCAGTGGATTTAGACT | 305 | 25 |
|  | NM_003600 | Probe | CGCTAAAAGCAAAGA | 306 | 16 |
| SULT1E1.1 | NM_005420 | Forward | ATGGTGGCTGGTCATCCAA | 307 | 19 |
|  | NM_005420 | Reverse | ATAAGGAACCTGTCCTTGCATGAA | 308 | 24 |
|  | NM_005420 | Probe | TTCTCCACAAACTCTGGAAAGGATCCAGGA | 309 | 30 |
| SULT4A1.1 | NM_014351 | Forward | CACCTGCCCTACCGCTTTC | 310 | 19 |
|  | NM_014351 | Reverse | GGGTTGCGAGCCATATAGATG | 311 | 21 |
|  | NM_014351 | Probe | CCTCTGACCTCCACAATGGAGACTCCA | 312 | 27 |
| SURV.2 | NM_001168 | Forward | TGTTTTGATTCCCGGGCTTA | 313 | 20 |
|  | NM_001168 | Reverse | CAAAGCTGTCAGCTCTAGCAAAG | 314 | 24 |
|  | NM_001168 | Probe | TGCCTTCTTCCTCCCTCACTTCTCACCT | 315 | 28 |
| TBP.1 | NM_003194 | Forward | GCCCGAAACGCCGAATATA | 316 | 19 |
|  | NM_003194 | Reverse | CGTGGCTCTCTTATCCTCATGAT | 317 | 23 |
|  | NM_003194 | Probe | TACCGCAGCAAACCGCTTGGG | 318 | 21 |
| TFRC.3 | NM_003234 | Forward | GCCAACTGCTTTCATTTGTG | 319 | 20 |
|  | NM_003234 | Reverse | ACTCAGGCCCATTTCCTTTA | 320 | 20 |
|  | NM_003234 | Probe | AGGGATCTGAACCAATACAGAGCAGACA | 321 | 28 |
| TST.1 | NM_003312 | Forward | GGAGCCGGATGCAGTAGGA | 322 | 19 |
|  | NM_003312 | Reverse | AAGTCCATGAAAGGCATGTTGA | 323 | 22 |
|  | NM_003312 | Probe | ACCACGGATATGGCCCGAGTCCA | 324 | 23 |
| UGT1A3.1 | NM_019093 | Forward | GATGCCCTTGTTTGGTGATCA | 325 | 21 |
|  | NM_019093 | Reverse | AGGGTCACTCCAGCTCCCTTA | 326 | 21 |
|  | NM_019093 | Probe | TCTCCATGCGCTTTGCATTGTCCA | 327 | 24 |
| UGT2B7.2 | NM_001074 | Forward | CAATGGCATCTACGAGGCA | 328 | 19 |
|  | NM_001074 | Reverse | CAGGTTGATCGGCAAACA | 329 | 18 |
|  | NM_001074 | Probe | AATCCCCACCATAGGGATCCCATG | 330 | 24 |
| upa.3 | NM_002658 | Forward | GTGGATGTGCCCTGAAGGA | 331 | 19 |
|  | NM_002658 | Reverse | CTGCGGATCCAGGGTAAGAA | 332 | 20 |
|  | NM_002658 | Probe | AAGCCAGGCGTCTACACGAGAGTCTCAC | 333 | 28 |

TABLE 6-continued

| Probe Name | Accession Number | Reagent | Oligo Sequence | Seq id No: | Oligo Length |
|---|---|---|---|---|---|
| VDAC1.1 | NM_003374 | Forward | GCTGCGACATGGATTTCGA | 334 | 19 |
| | NM_003374 | Reverse | CCAGCCCTCGTAACCTAGCA | 335 | 20 |
| | NM_003374 | Probe | TTGCTGGGCCTTCCATCCGG | 336 | 20 |
| VDAC2.1 | NM_003375 | Forward | ACCCACGGACAGACTTGC | 337 | 18 |
| | NM_003375 | Reverse | AGCTTTGCCAAGGTCAGC | 338 | 18 |
| | NM_003375 | Probe | CGCGTCCAATGTGTATTCCTCCAT | 339 | 24 |
| XPC.1 | NM_004628 | Forward | GATACATCGTCTGCGAGGAA | 340 | 20 |
| | NM_004628 | Reverse | CTTTCAATGACTGCCTGCTC | 341 | 20 |
| | NM_004628 | Probe | TTCAAAGACGTGCTCCTGACTGCC | 342 | 24 |

TABLE 7

| Amplicon Name | Accession Number | Amplicon Sequence | SEQ ID No: |
|---|---|---|---|
| AKR1C1.1 | BC040210 | AGATGAGAGCAGCCTGAACTTACACTGTGAAAATGCCCTGGAGAAATGCAGAGATGCAGGTTTAATGAAGTCCATCA | 343 |
| AKR1C2.1 | NM_001354 | TGCCAGCTCATTGCTCTTATAGCCTGTGAGGGAGGAAGAAACATTTGCTAACCAGGCCAGTGACAGA | 344 |
| AKR1C3.1 | NM_003739 | GCTTTGCCTGATGTCTACCAGAAGCCCTGTGTGTGGATGGTGACGCAGAGGACGTCTCTATGCCGGTGACTGGAC | 345 |
| ATP5A1.1 | NM_004046 | GATGCTGCCACTCAACAACTTTTGAGTCGTGGCGTGCGTCTAACTGAGTTGCTGAAGCAAGGACA | 346 |
| B-actin.2 | NM_001101 | CAGCAGATGTGGATCAGCAAGCAGGAGTATGACGAGTCCGGCCCCTCCATCGTCCACCGCAAATGC | 347 |
| Bcl2.1 | NM_000633 | CTGGGATGCCTTTGTGGAACTGTACGGCCCCAGCATGCGGCCTCTGTTTGATTTCTCCTGGCTGTCTCTG | 348 |
| Bcl2.2 | NM_000633 | CAGATGGACCTAGTACCCACTGAGATTTCCACGCCGAAGGACAGCGATGGGAAAAATGCCCTTAAATCATAGG | 349 |
| Bcl2 intron 1 50 kb.1 | NM_000633int1-50 kb | GCATCATTTGTTGGGTATGGAGTTGCAGAAGTTGGGTTGAGGGACACTGGCTTCTAGAATCAAATATTGGCCTCCATAGA | 350 |
| Bcl2 intron 1 50 kb.2 | NM_000633int1-50 kb | GGGCAGTGGCCTGATGAAAAGCAAAAATGAAGAAAAGAATAAGGAAAGACACAGTTTTGCCAT | 351 |
| Bcl2 intron 1 100 kb.1 | NM_000633int1-100 kb | GTCACTTTTATCTCACAGCATCACAAGGAGGAACATCTGACAGCACTTGCCAGGTTATCAAGACACCAAGATCCAATGC | 352 |
| Bcl2 intron 1 150 kb.2 | NM_000633int1-150 kb | GGAGAAGTAGCCAGCCCATTTAAAATGTCAGCAAAGATTCCAGTTGTCTAAACGCGCCAGGGACA | 353 |
| Bcl2 intron1 3'.1 | NM_000633int1-3 | CTAGCCACCCCAAGAGAAACCCCCTGACAGCTCCCTTTCCCCAGGAGAACCTTGACCTTAGAGGTTGGCA | 354 |
| Bcl2-beta.1 | NM_000657 | TGGGTAGGTGCACTTGGTGATGTGAGTCTGGGCTGAGGCCACAGGTCCGAGATGCGGGGGTTGGAGT | 355 |
| CAT.1 | NM_001752 | ATCCATTCGATCTCACCAAGGTTTGGCCTCACAAGGACTACCCTCTCATCCCAGTTGGTAAACTGGTCTTAACCGGA | 356 |
| CD68.2 | NM_001251 | TGGTTCCCAGCCCTGTGTCCACCTCCAAGCCCAGATTCAGATTCGAGTCATGTACACAACCCAGGGTGGAGG | 357 |
| CDH1.3 | NM_004360 | TGAGTGTCCCCCGGTATCTTCCCCGCCCTGCCAATCCCGATGAAATTGGAAATTTTATTGATGAAAATCTGAAAGAGCGGCTG | 358 |
| CEGP1.2 | NM_020974 | TGACAATCAGCACACCTGCATTCACCGCTCGGAAGAGGGCCTGAGCTGCATGAATAAGGATCACGGCTGTAGTCACA | 359 |

TABLE 7-continued

| Amplicon Name | Accession Number | Amplicon Sequence | SEQ ID No: |
|---|---|---|---|
| CEGP1.6 | NM_020974 | GCTGCATTTTATGTCCAAATGGAACCTTCCAAAATGAGGAAGGACAAATGACTTGTGAACCATGCCCAAGAC CA | 360 |
| CEGP1 intron 4.1 | NM_020974int4 | TCCCCTTGCCTTTGGAGAACAGCCCAAATCCTTTGATGCCTCCAGGCCTTT | 361 |
| CEGP1 intron 5.1 | NM_020974int5 | CTTAATGGTGTTTAGCACAGATGCAGGCTGTTTCCTGTGCATTTGCCCCCCCAGCAGGCCCTGTGCTGCTTC GCATGCTACAGTGG | 362 |
| COMT.1 | NM_000754 | CCTTATCGGCTGGAACGAGTTCATCCTGCAGCCCATCCACAACCTGCTCATGGGTGACACCAAGGAG | 363 |
| COX8.1 | NM_004074 | CGTTCTGTCCCTCACACTGTGACCTGACCAGCCCCACCGGCCCATCCTGGTCATGTTACTGCATTTG | 364 |
| CRYZ.1 | NM_001889 | AAGTCCTGAAATTGCGATCAGATATTGCAGTACCGATTCCAAAAGACCATCAGGTTCTAATCAAGGTCCATG CATGTG | 365 |
| CTSL2.1 | NM_001333 | TGTCTCACTGAGCGAGCAGAATCTGGTGGACTGTTCGCGTCCTCAAGGCAATCAGGGCTGCAATGGT | 366 |
| CTSL2.10 | NM_001333 | TCAGAGGCTTGTTTGCTGAGGGTGCCTGCGCAGCTGCGACGGCTGCTGGTTTTGAAACATGAATCTTTCGCT TCCT | 367 |
| CYP.1 | NM_006347 | TGGACTTCTAGTGATGAGAAAGAT-TGAGAATGTTCCCACAGGCCCCAACAATAAGCCCAAGCTACCTGTGGTGA CGTCTCGCAGTG | 368 |
| CYP17A1.1 | NM_000102 | CCGGAGTGACTCTATCACCAACATGCTGGACACACTGATGCAAGCCAAGATGAACTCAGATAATGGCAATGCT GGC | 369 |
| CYP19A1.1 | NM_000103 | TCCTTATAGGTACTTTCAGCCATTTGGCTTTGGGCCCCGTGGCTGTGCAGGAAAGTACATCGCCATGGTG | 370 |
| CYP1A1.2 | NM_000499 | AATAATTTCGGGGAGGTGGTTGGCTCTGGAAACCCAGCTGACTTCATCCCTATTCTTCGCTACCTACCCAACC | 371 |
| CYP1B1.3 | NM_000104 | CCAGCTTTGTGCCTGTCACTATTCCTCATGCCACCACTGCCAACACCTCTGTCTTGGGCTACCACATTCCC | 372 |
| CYP4Z1.1 | NM_178134 | GCCTTACACCACGATGTGCATCAAGGAATGCCTCCGCCTCTACGCACCGGTAGTAAACATATCCCGGTTACTC GAC | 373 |
| EPHX1.2 | NM_000120 | ACCGTAGGCTCTGCTCTGAATGACTCTCCTGTGGGTCTGGCTGCCTATATTCTAGAGAAGTTTTCCACCTGGA CCA | 374 |
| EstR1.1 | NM_000125 | CGTGGTGCCCCTCTATGACCTGCTGCTGGAGATGCTGGACGCCCACCGCCTACATGCGCCCACTAGCC | 375 |
| FOXM1.1 | NM_021953 | CCACCCCGAGCAAATCTGTCCTCCCCAGAACCCCTGAATCCTGGAGGCTCACGCCCCCAGCCAAAGTAGGGGG ACTGGATTT | 376 |
| FOXM1.3 | NM_021953 | TGCCCAGATGTGCGCTATTAGATGTTTCTCTGATAATGTCCCCAATCATACCAGGGAGACTGGCATTGA | 377 |
| FOXM1 intron 5.1 | NM_021953 int5 | TGGACAGAGACAAGATGTGATGTGGGAAGGGTCCCTATGGCCATGTTTTGTCTAGGTGCCAGC | 378 |
| FOXM1 intron 7.1 | NM_021953 int7 | GGTGTCCTATTTTCCTCTGAAGAGAGATTCTGGCCAATTAAGAATGTTGGACCTTCAGCTTGCA | 379 |
| GAPDH.1 | NM_002046 | ATTCCACCCATGGCAAATTCCATGGCACCGTCAAGGCTGAGAACGGGAAGCTTGTCATCAATGGAAATCCC ATC | 380 |
| GCLC.3 | NM_001498 | CTGTTGCAGGPAGGCATTGATCATCTCCTGGCCCAGCATGTTGCTCATCTCTTTATTAGAGACCCACTGAC | 381 |
| GCLM.2 | NM_002061 | TGTAGAATCAAACTCTTCATCATCAACTAGAAGTGCAGTTGACATGGCCTGTTCAGTCCTTGGAGTTGCACAG CTGGATTCTGTG | 382 |
| GPX1.2 | NM_000581 | GCTTATGACCGACCCCAAGCTCATCACCTGGTCTCCGGTGTGTCGCAACGATGTTGCCTGGAACTTT | 383 |
| GPX2.2 | NM_002083 | CACACAGATCTCCTACTCCATCCAGTCCTGAGGAGCCTTAGGATGCAGCATGCCTTCAGGAGACACTGCTGGA | 384 |
| GSTM1.1 | NM_000561 | AAGCTATGAGGAAAAGAAGTACACGATGGGGACGCTCCTGATTATGACAGAAGCCAGTGGCTGAATGAAAAA TTCCCAAGCTGGGCC | 385 |
| GSTM1 var2.1 | NM_146421 | CCATGGTTTGCAGGAAACAAGGGCTTGGAGAAGATCTCTGCCTACATGAAGTCCAGCCGCTTCCTCCCAAGAC CTGTGTTCT | 386 |
| GSTM1 intron 1.1 | NM_000561 int1 | AACGGGTACGTGCAGTGTAAACTGGGGGCTTCCCTGGTGCAGACAAAGTCAGGGACCCTCCATCTCTGACGCG ACCTGC | 387 |

TABLE 7-continued

| Amplicon Name | Accession Number | Amplicon Sequence | SEQ ID No: |
|---|---|---|---|
| GSTM1 intron 3.1 | NM_000561 int3 | TCTGTGTCCACCTGCATTCGTTCATGTGACAGTATTCTTATTTCAGTCCTGCCATGAGCAG | 388 |
| GSTM1 intron 5.1 | NM_000561 int5 | CGACTCCAATGTCATGTCAACAAAAGCAGAGGCAATTCCCACCAACCTTAGGACACGATCCAGGCATCCCAGGGT | 389 |
| GSTM1 intron 5.2 | NM_000561 int5 | GGCAATTCCCACCAACCTTAGGACACGATCCAGGCATCCCAGGGTAGAAATTCAGTTCCTGTATGGTAAAGTTT | 390 |
| GSTM1 intron 5.3 | NM_000561 int5 | ATGGCACCCTCGAATTGCATCTTCTCCTCAACAGTTTTCTGAGTGCTGTCATTGACATGCA | 391 |
| GSTM1 intron 7.2 | NM_000561 int7 | GCCTCCCTGTGGAAAAGGAGACTGTTTGTGCAGTCAAGGAGTGACAGGGCCTGGTGTGA | 392 |
| GSTM2 gene.1 | NM_000848gene | GCAGGAACGAGAGGAGGAGATGGGGCTCCCCTTGTGCAGAGTCGTCACAAAGTCAGGGACCCTCCATCTCTGACCCGAGCTG | 393 |
| GSTM2 gene.4 | NM_000848gene | CTGGGCTGTGAGGCTGAGAGTGAATCTGCTTTACGAGGGTAGGCGGGGAATCAGAAAAGGAGCAGATTCGC | 394 |
| GSTM3.2 | NM_000849 | CAATGCCATCTTGCGCTACATCGCTCGCAAGCACAACATGTGTGGTGAGACTGAAGAAGAAAGATTCGAGTGGAC | 395 |
| GSTM3.5 | NM_000849 | CCAGAAGCCAAGGATCTCTCTAGTGATGGTCAGAGGGCCCAAATGGCAGGGATACCCAGTGATGTCAGGAGGAATA | 396 |
| GSTM3.6 | NM_003849 | TCACAGTTTCCCTAGTCCTCGAAGGCTCGGAAGCCCGTCACCATGTCGTGCGAGTCGTCTATGGTTCTCGGGTACTGGGATATTCG | 397 |
| GSTM4.1 | NM_000850 | CGGACCTTGCTCCCTGAACACTCGGAGGTGGCGGTGGATCTTACTCCTTCCAGCCAGTGAGGATCCAGCAACCTGCTCCG | 398 |
| GSTM5.1 | NM_000851 | TCCCTGAGGCTCCCTTGACTCAGGACTGTGCTCGAATTGTGGGTGGTTTTTTGTCTTCTGTTGTCCACAGCC | 399 |
| GSTM5.2 | NM_000851 | GAAAGGTGCTCTGTGCCAAGTTCCTCACTCATTCGCGCTCCTGTAGGCCGTCTAGAACTGGCATGGTTCAAAGAGGGGCTAGG | 400 |
| GSTp.3 | NM_000852 | GAGACCCTGCTGTCCCAGAACCAGGGAGGCAAGACCTTCATTGTGGGAGACCAGATCCTTCGCTGACTACAACC | 401 |
| GSTT1.3 | NM_000853 | CACCATCCCCACCCTGTCTTCCACAGCCGCCTGAAAGCCACAATGAGAATGATGCACACTGAGGCC | 402 |
| GUS.1 | NM_000181 | CCCACTCAGTAGCCAAGTCACAATGTTTGGAAAACAGCCCGTTTACTTGAGCAAGACTGATACCACCTGCGTG | 403 |
| HOXB13.1 | NM_006361 | CGTGCCTTATGGTTACTTTGGAGGCGGGTACTACTCCTGCCGAGTGTCCCGGAGCTCGCTGAAACCCTGTG | 404 |
| HSD17B1.1 | NM_000413 | CTGGACCGCACGGACATCCACACCTTCCACCGCTTCTACCAATACCTCGCCCACAGCAAGCAAGTCTTTCGCGAGGCG | 405 |
| HSD17B2.1 | 406 | GCTTTCCAAGTGGGGAATTAAAGTTGCTTCCATCCAACCTGGAGGCTTCCTAACAAATATCGCAGGCA | 395 |
| HSD17B4.1 | NM_000414 | TTGTCCTTTGGCTTTGTCACGAGAGTTGTGAGGAGAATGGTGGCTTGTTTGAGGTTGGAGCAGGATGGATTG | 407 |
| IL17RB.2 | NM_018725 | ACCCTCTGGTGGTAAATGGACATTTTCCTACATCGGCTTCCCTGTAGAGCTGAACACAGTCTATTTCATTGGGGCC | 408 |
| IMMT.1 | NM_006839 | CTGCCTATGCCAGACTCAGAGGAATCGAACAGGCTGTTCAGAGCCATGCAGTTGCTGAAGAGGAAGCCAGAAAAGC | 409 |
| Ki-67.2 | NM_002417 | CGGACTTTGGGTGCGACTTGACGAGCGGTGGTTCGACAAGTGGCCTTGCGGGCCGGATCGTCCCAGTGGAAGAGTTGTAA | 410 |
| LIPA.1 | NM_000235 | CCAGTTGTCTTCCTGCAACATGGCTTGCTGGCAGATTCTAGTAACTGGGTCACAAACCTTGCCAACAG | 411 |
| MDH2.1 | NM_005918 | CCAACACCTTTGTTGCAGAGCTGAAGGGTTTGGATCCAGCTCGAGTCAACGTCCCTGTCATTG | 412 |
| mGST1.2 | NM_020300 | ACGGATCTACCACACCATTGCATATTTGACACCCCTTCCCCAGCCAAATAGAGCTTTGAGTTTTTTGTTGGATATGGA | 413 |
| MGST3.1 | NM_004528 | AGCTGTTGGAGGTGTTTACCACCCGCGTATAGCTTCTGGCCTGGGCTTGGCCTGGATTGTTGGACGA | 414 |
| MMTV-like env.3 | AF346816 | CCATACGTGCTGCTACCTGTAGATATTGGTGATGAACCATGGTTTGATGATTCTGCCATTCAAACCTTTAGG | 415 |

TABLE 7-continued

| Amplicon Name | Accession Number | Amplicon Sequence | SEQ ID No: |
|---|---|---|---|
| MPV17.1 | NM_002437 | CCAATGTGTTGCTGTTATCTGGAACTCCTACCTGTCCTGGAAGGCACATCGGCTCTAAGCCTGCCTCACTCCAT | 416 |
| MVP.1 | NM_017458 | ACGAGAACGAGGGCATCTATGTGCAGGATGTCAAGACCGGAAAGGTGCGCGCTGTGATTGGAAGCACCTACATGC | 417 |
| NAT1.1 | NM_000662 | TGGTTTTGAGACCACGATGTTGGGAGGGTATGTTTACAGCACTCCAGCCAAAAAATACAGCACTGGCATGATTCA | 418 |
| NAT2.1 | NM_000015 | TAACTGACATTCTTGAGCACCAGATCCGGGCTGTTCCCTTTGAGAACCTTAACATGCATTGTGGGCAAGCCAT | 419 |
| NCOA2.1 | NM_006540 | AGTGACCTCCGTGCCTACGTCAGGGCTGTCCTCCATGGGTCCCGAGCAGGTTAATGATCCTGCTCTGAGGGGAG | 420 |
| NDUFA7.1 | NM_005001 | GCAGCTACGCTACCAGGAGATCTCCAAGCGAACTCAGCCTCCTCCCAAGCTCCCTGTGGGTCCTAGCCACAAGCTCTCC | 421 |
| NQO1.1 | NM_000903 | CAGCAGACGCCCGAATTCAAATCCTGGAAGGATGGAAGAAACGCCTGGAGAATATTTGGGATGAGACACCA | 422 |
| NQO2.1 | NM_000904 | AGCGCTCCTTTCCGTAACCACGGGAGGCACGGCCGAGATGTACACGAAGACAGGAGTCAATGGA | 423 |
| P53.2 | NM_000546 | CTTTGAACCCTTGCTTGCAATAGGTGTGCGTCAGAAGCACCCAGGACTTCCATTTGCTTTGTCCCGGG | 424 |
| PAI1.3 | NM_000602 | CCGCAACGTGGTTTTCTCACCCTATGGGGTGGCCTCGGTGTTGGCCATGCTCCAGCTGACAACAGGAGGAGAAACCCAGCA | 425 |
| PR.6 | NM_000926 | GCATCAGGCTGTCATTATGGTGTCCTTACCTGTGGGAGCTGTAAGGTCTTCTTTAAGAGGGCAATGGAAGGGCAGCACAACTACT | 426 |
| PR.12 | NM_000926 | GTTCCATCCCAAAGAACCTGCTATTGAGAGTAGCATTCAGAATAACGGGTGGAAATGCCAACTCCAGAGTTTC | 427 |
| PRAME.3 | NM_006115 | TCTCCATATCTGCCTTGCAGAGTCTCCTGCAGCACCTCATCGGGCTGAGCAATCTGACCCACGTGC | 428 |
| PRAME.4 | NM_006115 | CCACTGCTCCCAGCTTACAACCTTAAGCTTCTACGGGAATTCCATCTCCATATCTGCCTTGCAG | 429 |
| PRAME intron 5.1 | NM_006115 | ATCAGGCACAGAGATAGAGGTGACTGGGGCCCAGGCAGTGGCAGAAGGAAGCCCGAGTTGAAAGA | 430 |
| PRDX2.1 | NM_005809 | GGTGTCCTTCGCCAGATCACTGTTAATGATTTGCCTGTGGGACGCTCCGTGGATGAGGCTCTGCGGCTG | 431 |
| PRDX3.1 | NM_006793 | TGACCCCAATGGAGTCATCAAGCATTTGAGCGTCAACGATCTCCCAGTGGGCCGAAGCGTGGAAGAAACCCTCCGCTTGG | 432 |
| PRDX4.1 | NM_006406 | TTACCCATTTGGCCTGGATTAATACCCCTCGAAGACAAGGAGGACTTGGGCCAATAAGGATTCCACTTCTTTCAG | 433 |
| PRDX6.1 | NM_004905 | CTGTGAGCCAGAGGATGTCAGCTGCCAATTGTGTTTTCCTGCAGCAATTCCATAAACACATCCTGGTGTCATCACA | 434 |
| RPLPO.2 | NM_001002 | CCATTCTATCATCAACGGGTACAAACGAGTCCTGGCCTTGTCTGTGGAGACGGATTACACCTTCCCACTTGCTGA | 435 |
| SC5DL.1 | NM_006918 | CGCCTACATAAACCTCACCATATTTGGAAGATTCCTACTCCATTTGCAAGTCATGCTTTTCACCCTATTGATGG | 436 |
| SOD1.1 | NM_000454 | TGAAGAGAGGCATGTTGGAGACTTGGGCAATGTGACTGCTGACAAAGATGGTGTGGCCGATGTGTCTATT | 437 |
| SOD2.1 | NM_000636 | GCTTGTCCAAATCAGGATCCACTGCAAGGAACAACAGGCCTTATTCCACTGCTGGGGATTGATGTGTGGGAGCACGCT | 438 |
| SOD3.1 | NM_003102 | CCATAAGCCCTGAGACTCCCGCCTTTGACCTGACGATCTTCCCCCTTCCCGCCTTCAGGTTCCTCCTA | 439 |
| SRD5A2.1 | NM_000348 | GTAGGTCTCCTGGCGTTCTGCCAGCTGGCCTGGGGATTCTGAGTGGTGTCTGCTTAGAGTTTACTCCTACCCTTCCAGGGA | 440 |
| STK15.2 | NM_003600 | CATCTTCCAGGAGGACCACTCTCTGTGGCACCCTGGACTACCTGCCCCCTGAAATGATTGAAGGTCGGA | 441 |
| STK15.8 | NM_003600 | GCCCCCTGAAATGATTGAAGGTCGGATGCATGATGAGAAGGTGGATCTCTGGAGCCTTGGA | 442 |
| STK15 intron 2.1 | NM_003600int2 | CATTCACATTTATAAACCCACATGGAGGTTGGTCTTGTCGGGAATTCTTTCCGCCTTTACTTTGGATT | 443 |
| STK15 intron 4.1 | NM_003600int4 | GCGAGGAATGAACCCACAGACTCTTTTGCTTTTAGCGGTCTAACAGAGGCTAAGAGTCTAAATCCACTGGTTCTCATGC | 444 |

TABLE 7-continued

| Amplicon Name | Accession Number | Amplicon Sequence | SEQ ID No: |
|---|---|---|---|
| SULT1E1.1 | NM_005420 | ATGGTGGCTGGTCATCCAAATCCTGGATCCTTTCCAGAGTTTGTGGAGAAATTCATGCAAGGACAGGTTCCTTAT | 445 |
| 5ULT4A1.1 | NM_014351 | CACCTGCCCTACCGCTTTCTGCCCTCTGACCTCCACAATGGAGACTCCAAGGTCATCTATATGGCTCGCAACCC | 446 |
| SURV.2 | NM_001168 | TGTTTTGATTCCCGGGCTTACCAGGTGAGAAGTGAGGGAGGAAGAAGGCAGTGTCCCTTTTGCTAGAGCTGACAGCTTTG | 447 |
| TBP.1 | NM_003194 | GCCCGAAACGCCGAATATAATCCCAAGCGGTTTGCTGCGGTAATCATGAGGATAAGAGAGCCACG | 448 |
| TFRC.3 | NM_003234 | GCCAACTGCTTTCATTTGTGAGGGATCTGAACCAATACAGAGCAGACATAAAGGAAATGGGCCTGAGT | 449 |
| TST.1 | NM_003312 | GGAGCCGGATGCAGTAGGACTGGACTCGGGCCATATCCGTGGTGCCGTCAACATGCCTTTCATGGACTT | 450 |
| UGT1A3.1 | NM_019093 | GATGCCCTTGTTTGGTGATCAGATGGACAATGCAAAGCGCATGGAGACTAAGGGAGCTGGAGTGACCCT | 451 |
| UGT2B7.2 | NM_001074 | CAATGGCATCTACGAGGCAATCTACCATGGGATCCCTATGGTGGGGATTCCATTGTTTGCCGATCAACCTG | 452 |
| upa.3 | NM_002658 | GTGGATGTGCCCTGAAGGACAAGCCAGGCGTCTACACGAGAGTCTCACACTTCTTACCCTGGATCCGCAG | 453 |
| VDAC1.1 | NM_003374 | GCTGCGACATGGATTTCGACATTGCTGGGCCTTCCATCCGGGGTGCTCTGGTGCTAGGTTACGAGGGCTGG | 454 |
| VDAC2.1 | NM_003375 | ACCCACGGACAGACTTGCGCGCGTCCAATGTGTATTCCTCCATCATATGCTGACCTTGGCAAAGCT | 455 |
| XPC.1 | NM_004628 | GATACATCGTCTGCGAGGAATTCAAAGACGTGCTCCTGACTGCCTGGGAAAATGAGCAGGCAGTCATTGAAAG | 456 |

Study Methods
Gene Expression

For each patient sample included in the study, 50 ng of RNA extracted from a FPET sample was amplified using commercially available RNA amplification kits and protocols (Genisphere). Expression levels of test and reference genes listed in Table 5 were reported as ($C_T$) values from the qRT-PCR assay (TaqMan®). Based on the relative invariability of their measured expression in study samples and on the lack of observed correlation between their measured expression and clinical outcome, CDH1, TBP, EPHX1, SERPINE1 and CD68 were chosen as reference genes. Test gene expression values were normalized relative to the mean of these reference genes. Reference-normalized expression measurements typically range from 0 to 15, where a one unit increase generally reflects a 2-fold increase in RNA quantity.

Main effect Cox proportional hazard models (D. R. Cox (1972) Regression Models and Life-Tables (with discussion). 3 Royal Statistical Soc. B, 34:187-220) were utilized to compare the additional contribution of gene expression beyond standard clinical prognostics variables, including age, clinical tumor size, and tumor grade. A test for comparing the reduced model, excluding the gene expression variable, versus the competing full model including the gene variable of interest, called the likelihood ratio test (Ronald Fisher (1922) "On the Mathematical Foundations of Theoretical Statistics", Phil. Trans. Royal Soc., series A, 222:326, 1922; Leonard Savage (1962). The Foundations of Statistical Inference (1962)) was utilized to identify statistically significant prognostic genes.

Study Results

Using the methods described above, 34 genes were identified, for which the expression level was found to be significantly correlated with DRFS (p<0.1). The genes are shown in Table 8 together with Hazard Ratio and p-values. Results utilizing two distinct probe primer sets designed to measure distinct expression products of the PGR gene are shown. The PR.12 probe primer set is targeted specifically toward PGR-B mRNA, which gives rise to a longer translation product than does PGR-A mRNA. PR.6 recognizes both PGR-A and PGR-B. Measurement using PR.12 resulted in a lower Hazard Ratio than did PR.6, indicating that PGR-B may be the more powerful predictor of clinical outcome.

TABLE 8

| Gene Official Symbol | Amplicon Name (Results) | Hazard Ratio | HR 95% LCL | HR 95% UCL | LR P-Value |
|---|---|---|---|---|---|
| BCL2 | Bcl2 intron 1 50kb.1 | 0.64 | 0.52 | 0.80 | 0.0002 |
| GSTM2 | GSTM2 gene.4 | 0.64 | 0.49 | 0.83 | 0.0003 |
| GSTM3 | GSTM3.6 | 0.57 | 0.42 | 0.78 | 0.0003 |
| SCUBE2 | CEGP1.6 | 0.76 | 0.65 | 0.88 | 0.0003 |
| BCL2 | Bcl2-beta.1 | 0.62 | 0.47 | 0.81 | 0.0007 |
| GSTM1 | GSTM1.1 | 0.71 | 0.58 | 0.86 | 0.0009 |
| PGR | PR.6 | 0.81 | 0.71 | 0.92 | 0.0019 |
| MVP | MVP.1 | 0.44 | 0.26 | 0.74 | 0.0026 |
| GSTM4 | GSTM4.1 | 0.68 | 0.53 | 0.87 | 0.0044 |
| PGR | PR.12 | 0.64 | 0.46 | 0.90 | 0.0067 |
| BIRC5 | SURV.2 | 1.41 | 1.08 | 1.82 | 0.0091 |
| NAT1 | NAT1.1 | 0.85 | 0.74 | 0.97 | 0.0161 |
| CRYZ | CRYZ.1 | 0.60 | 0.38 | 0.93 | 0.0263 |
| GPX1 | GPX1.2 | 0.41 | 0.19 | 0.88 | 0.0263 |
| MKI67 | Ki-67.2 | 1.41 | 1.02 | 1.93 | 0.0270 |
| PRAME | PRAME.3 | 1.17 | 1.02 | 1.33 | 0.0270 |
| PPIH | CYP.1 | 0.58 | 0.36 | 0.92 | 0.0283 |
| CYP17A1 | CYP17A1.1 | 0.69 | 0.49 | 0.99 | 0.0323 |
| IL17RB | IL17RB.2 | 0.81 | 0.68 | 0.98 | 0.0334 |
| CAT | CAT.1 | 0.63 | 0.41 | 0.96 | 0.0400 |
| CYP4Z1 | CYP4Z1.1 | 0.86 | 0.75 | 1.00 | 0.0416 |
| ESR1 | EstR1.1 | 0.87 | 0.77 | 0.99 | 0.0418 |
| GPX2 | GPX2.2 | 0.68 | 0.48 | 0.98 | 0.0419 |
| PRDX3 | PRDX3.1 | 0.55 | 0.31 | 0.98 | 0.0454 |
| STK6 | STK15.2 | 1.63 | 0.99 | 2.69 | 0.0475 |
| GSTM5 | GSTM5.2 | 0.77 | 0.58 | 1.02 | 0.0493 |
| SC5DL | SC5DL.1 | 0.65 | 0.42 | 1.00 | 0.0520 |

TABLE 8-continued

| Gene Official Symbol | Amplicon Name (Results) | Hazard Ratio | HR 95% LCL | HR 95% UCL | LR P-Value |
|---|---|---|---|---|---|
| CTSL2 | CTSL2.10 | 1.22 | 1.00 | 1.49 | 0.0620 |
| VDAC1 | VDAC1.1 | 1.89 | 0.96 | 3.72 | 0.0689 |
| PLAU | upa.3 | 0.66 | 0.43 | 1.03 | 0.0716 |
| TFRC | TFRC.3 | 1.49 | 0.97 | 2.30 | 0.0759 |
| NQO1 | NQO1.1 | 1.42 | 0.95 | 2.13 | 0.0803 |
| GSTP1 | GSTp.3 | 0.72 | 0.49 | 1.05 | 0.0840 |
| ATP5A1 | ATP5A1.1 | 0.56 | 0.30 | 1.07 | 0.0850 |
| GUSB | GUS.1 | 0.67 | 0.42 | 1.08 | 0.0861 |

Two genes from the glutathione peroxidase family, GPX1 and GPX2, were positive prognosticators. GPX1 gave a very strong positive Cox value (H.R.=0.41, p=0.0263) and GPX2 was also strongly positive (H.R.=0.68, p=0.0419). GPX1 encodes a selenium-dependent glutathione peroxidase that functions in the detoxification of hydrogen peroxide, and is one of the most important antioxidant enzymes in humans. GPX1 overexpression delays cell growth and protects from GSH and $H_2O_2$ toxicity. Interestingly, these biological activities are similar to BCL2, another strong positive prognostic indicator in breast. GPX2 also encodes a selenium-dependent glutathione peroxidase and is one of two isoenzymes responsible for the majority of the glutathione-dependent hydrogen peroxide-reducing activity in the epithelium of the gastrointestinal tract. Studies in knockout mice indicate that mRNA expression levels respond to luminal microflora, suggesting a role of GPX2 in preventing inflammation in the GI tract, Another strong positive Cox value was found with peroxiredoxin 3, (PRDX3; H.R.=0.55, p=0.0454). This gene encodes a protein with antioxidant function and is localized in the mitochondrion. PRDX3 is a member of a gene family that is responsible for regulation of cellular proliferation, differentiation, and antioxidant functions.

The strong positive prognostic' effect of CRYZ (H.R.=0.60, p=0.0263) is also consistent with its function as an antioxidant. CRYZ encodes the major detoxifying enzyme quinone reductase (QR) [NAD(P)H:quinone oxidoreductase]. It is hypothesized that QR inhibits estrogen-induced DNA damage by detoxification of reactive catecholestrogens. CRYZ is transcriptionally activated by anti-estrogen liganded ERβ. Up-regulation of QR, either by overexpression or induction by tamoxifen, can protect breast cells against oxidative DNA damage caused by estrogen metabolites, representing a possible novel mechanism of tamoxifen prevention against breast cancer. (See Table 9 Univariate Cox PH regression analysis. Assays are ordered by p-value, with p-values≤0.05 considered significant. Specimens from 125 breast cancer patients were assayed.)

TABLE 9

| Univariate Analysis | Hazard Ratio | HR 95% LCL | HR 95% UCL | P-Value |
|---|---|---|---|---|
| CRYZ.1 | 0.60 | 0.38 | 0.93 | 0.0263 |
| CYP1B1.3 | 0.81 | 0.55 | 1.19 | 0.2852 |
| UGT2B7.2 | 1.07 | 0.94 | 1.22 | 0.3763 |
| SULT1E1.1 | 1.08 | 0.91 | 1.28 | 0.3862 |
| COMT.1 | 0.87 | 0.42 | 1.81 | 0.711 |
| SULT4A1.1 | 1.01 | 0.82 | 1.25 | 0.9427 |
| CYP1A1.2 | 1.01 | 0.82 | 1.23 | 0.949 |
| UGT1A3.1 | 1.00 | 0.78 | 1.27 | 0.974 |

The cytochrome P450 proteins are monooxygenases which catalyze many reactions involved in drug metabolism and synthesis of cholesterol, steroids and other lipids. Two of the five cytochrome P450 superfamily members tested were also significant indicators of positive prognosis. CYP17A1 (H.R.=0.69, p=0.0323) localizes to the endoplasmic reticulum. It has both 17alpha-hydroxylase and 17,20-lyase activities and is a key enzyme in the steroidogenic pathway that produces progestins, mineralocorticoids, glucocorticoids, androgens, and estrogens. The recently discovered CYP4Z1 (H.R.=0.86, p=0.0416), also an endoplasmic reticulum integral membrane protein, is restricted to expression in breast and showed a clear over-expression in 52% of breast cancer samples in one study.

The antioxidant protein catalase (CAT) is located at the peroxisome and scavenges $H_2O_2$. Consistent with its function was the finding that CAT expression correlated with positive prognosis (H.R.=0.63, p=0.040).

The sterol-C5-desaturase like gene (SC5DL) encodes an enzyme that is involved in cholesterol biosynthesis. Expression of SC5DL is downregulated in human ovarian carcinomas in vivo during Taxol(R) (paclitaxel) treatment. In our study, increased expression of SC5DL was a positive prognostic indicator (H.R.=0.65, p=0.052).

NAT1, a xenobiotic-metabolizing enzyme, is an ERα-responsive gene in human breast cancer and has been suggested as a candidate molecular predictor of antiestrogen responsiveness. In a 97 ERalpha-positive breast tumor study, relapse-free survival was longer among patients with NAT1-overexpressing tumors (P=0.000052), and retained prognostic significance in Cox multivariate regression analysis (P=0.0013). In our current study, we show that NAT1 maintains a positive prognostic significance in a univariate Cox model (H.R.=0.85, p=0.0161) NAT1 also shows a strong expression correlation with ER (R=0.67), consistent with it being an ERα responsive gene.

The glutathione S-transferase pi gene (GSTP1) is a polymorphic gene encoding active, functionally different GSTP1 variant proteins that are thought to function in xenobiotic metabolism and play a role in susceptibility to cancer. GSTp was a positive prognostic indicator in our study (H.R.=0.72, p=0.084).

One skilled in the art will recognize numerous methods and materials similar or equivalent to those described herein, which could be used in the practice of the present invention. Indeed, the present invention is in no way limited to the methods and materials described. While the present invention has been described with reference to what are considered to be the specific embodiments, it is to be understood that the invention is not limited to such embodiments. To the contrary, the invention is intended to cover various modifications and equivalents included within the spirit and scope of the appended claims. For example, while the disclosure is illustrated by identifying genes and groups of genes useful in determining prognosis for patients diagnosed with invasive breast cancer, similar methods in determining prognosis for patients diagnosed with cancer of other cell types, including prostate and ovarian cancer.

What is claimed:

1. A method of predicting the likelihood of distant recurrence-free survival for a human subject diagnosed with breast cancer, comprising:

assaying a level of an RNA transcript of N-acetyltransferase 1 (NAT1) in a tumor sample obtained from said subject using a primer comprising a nucleotide sequence selected from SEQ ID NO:226 and SEQ ID NO:227;

normalizing the RNA level of NAT1 against the level of one or more reference genes to obtain a normalized expression level of NAT1;

using the normalized expression level of NAT1 to generate information comprising a prediction of the likelihood of distant recurrence-free survival for said subject, wherein the normalized expression level of NAT1 is positively correlated with a longer distant recurrence-free survival, and wherein distant recurrence-free survival is the time from surgery until the first diagnosis of distant recurrence.

2. The method of claim 1, wherein said normalized expression level is obtained by a method of gene expression profiling.

3. The method of claim 1, wherein said level of an RNA transcript of NAT1 is assayed by a polymerase chain reaction-based method.

4. The method of claim 1, wherein the tumor sample is obtained by biopsy.

5. The method of claim 4, wherein the biopsy is a fine needle biopsy.

6. The method of claim 1, wherein the tumor sample comprises fragmented RNA.

7. The method of claim 1, further comprising generating a report based on the information.

8. The method of claim 7, wherein the report comprises information concerning a risk of cancer recurrence for said subject.

9. The method of claim 7, wherein the report further comprises information to guide a cancer treatment decision for said subject.

10. The method of claim 1, further comprising assaying a level of at least one additional RNA transcript, or an expression product thereof, selected from the group GSTM1, GSTM2, GSTM3, GSTM4, GSTM5, TFRC, MVP, PRAME, PPIH, VDAC1, and CYP4Z1.

11. The method of claim 1, wherein the tumor sample is a paraffin-embedded and fixed tissue sample.

12. The method of claim 1, wherein the tumor sample is frozen.

13. The method of claim 1, wherein the breast cancer is invasive breast cancer.

14. A method for determining the likelihood of distant recurrence-free survival from a fixed, wax-embedded tissue sample obtained from a human breast cancer patient, comprising:

extracting RNA from the fixed, wax-embedded tissue sample;

amplifying an RNA transcript of N-acetyltransferase 1 (NAT1) using a primer comprising a nucleotide sequence selected from SEQ ID NO:226 and SEQ ID NO:227;

producing an amplicon of the RNA transcript of NAT1;

assaying a level of the amplicon of the RNA transcript of NAT1;

normalizing the level of the amplicon of the RNA transcript of NAT1, against the level of an amplicon of one or more reference genes to obtain a normalized NAT1 amplicon level;

comparing the normalized NAT1 amplicon level to a normalized NAT1 amplicon level obtained from a breast cancer reference set; and determining that the patient has an increased likelihood of longer distant recurrence-free survival if the normalized NAT1 amplicon level is increased and that the patient has a decreased likelihood of longer distant recurrence-free survival if the normalized NAT1 amplicon level is decreased, wherein distant recurrence-free survival is the time from surgery until the first diagnosis of distant recurrence.

15. The method of claim 14, wherein the RNA transcript of NAT1 is amplified by a polymerase chain reaction-based method.

16. The method of claim 14, wherein the level of the amplicon of the RNA transcript of NAT1 is a threshold cycle ($C_t$) value and the normalized NAT1 amplicon level is a normalized $C_t$ value.

17. The method of claim 14, further comprising amplifying an RNA transcript of at least one additional RNA transcript selected from the group GSTM1, GSTM2, GSTM3, GSTM4, GSTM5, TFRC, MVP, PRAMS, PPIH, VDAC1, and CYP4Z1.

18. The method of claim 14, further comprising generating a report based on the increased or decreased likelihood of distant recurrence-free survival of the patient.

19. The method of claim 14, wherein the breast cancer is invasive breast cancer.

* * * * *

UNITED STATES PATENT AND TRADEMARK OFFICE
CERTIFICATE OF CORRECTION

| | | |
|---|---|---|
| PATENT NO. | : 8,906,625 B2 | Page 1 of 1 |
| APPLICATION NO. | : 12/971874 | |
| DATED | : December 9, 2014 | |
| INVENTOR(S) | : Michael C. Kiefer, Joffre B. Baker and James Hackett | |

It is certified that error appears in the above-identified patent and that said Letters Patent is hereby corrected as shown below:

In the Claims

Claim 17, column 214, line 35, delete "PRAMS" and insert --PRAME--

Signed and Sealed this
Fifth Day of May, 2015

Michelle K. Lee
*Director of the United States Patent and Trademark Office*